(12) United States Patent
Andrews et al.

(10) Patent No.: US 11,052,134 B2
(45) Date of Patent: *Jul. 6, 2021

(54) ENHANCING HEALTH IN MAMMALS USING TELOMERASE REVERSE TRANSCRIPTASE GENE THERAPY

(71) Applicant: Sierra Sciences, LLC, Reno, NV (US)

(72) Inventors: William H. Andrews, Reno, NV (US); Lancer K. Brown, Sparks, NV (US); Hamid Mohammadpour, Reno, NV (US); Laura A. Briggs, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/803,006

(22) Filed: Feb. 27, 2020

(65) Prior Publication Data

US 2020/0306348 A1 Oct. 1, 2020

Related U.S. Application Data

(63) Continuation of application No. 15/220,250, filed on Jul. 26, 2016, now Pat. No. 10,610,574, which is a continuation of application No. 14/655,140, filed as application No. PCT/US2013/077619 on Dec. 23, 2013, now Pat. No. 9,453,209.

(60) Provisional application No. 61/746,438, filed on Dec. 27, 2012.

(51) Int. Cl.
| | | |
|---|---|---|
| *C07H 21/04* | (2006.01) | |
| *A61K 38/45* | (2006.01) | |
| *C12N 9/12* | (2006.01) | |
| *C12N 7/00* | (2006.01) | |
| *A61K 48/00* | (2006.01) | |
| *A61K 38/00* | (2006.01) | |

(52) U.S. Cl.
CPC .............. *A61K 38/45* (2013.01); *A61K 48/00* (2013.01); *A61K 48/005* (2013.01); *A61K 48/0066* (2013.01); *C12N 7/00* (2013.01); *C12N 9/1276* (2013.01); *C12Y 207/07049* (2013.01); *A61K 38/00* (2013.01); *C12N 2710/10341* (2013.01); *C12N 2740/15041* (2013.01); *C12N 2750/14143* (2013.01)

(58) Field of Classification Search
None
See application file for complete search history.

(56) References Cited

U.S. PATENT DOCUMENTS

| 6,475,789 B1 | 11/2002 | Cech et al. |
|---|---|---|
| 2009/0175892 A1* | 7/2009 | Langlade-Demoyen .................... A61P 35/00 424/185.1 |

FOREIGN PATENT DOCUMENTS

| WO | WO0216555 A2 | 2/2002 |
|---|---|---|
| WO | WO0216657 A1 | 2/2002 |
| WO | WO0216658 A1 | 2/2002 |
| WO | WO02070668 A2 | 9/2002 |
| WO | WO02072787 A2 | 9/2002 |
| WO | WO02090570 A2 | 11/2002 |
| WO | WO02090571 A2 | 11/2002 |
| WO | WO02101010 A2 | 12/2002 |
| WO | WO03000916 A2 | 1/2003 |
| WO | WO03016474 A2 | 2/2003 |
| WO | WO03034985 A2 | 5/2003 |
| WO | WO2012001170 A1 | 1/2012 |

OTHER PUBLICATIONS

Armanios, M. (J. Clin. Invest. 2013; 123(3): 996-1002).*
Sinn et al. (Gene Therapy 2005, 1089-1098).*
Puntel, Mariana, et al. ("Safety profile, efficacy, and biodistribution of a bicistronic high-capacity adenovirus vector encoding a combined immunostimulation and cytotoxic gene therapy as a prelude to a phase I clinical trial for glioblastoma." Toxicology and applied pharmacology 268.3 (2013): 318-330).*
And Askou et al. (Molecular Therapy—Methods & Clinical Development (2015) 2, 14064).*
Cristofari et al., Telomere length homeostasis requires that telomerase levels are limiting, The EMBO Journal (2006) 25:565-574.
De Jesus et al., Telomerase gene therapy in adult and old mice delays aging and increases longevity without increasing cancer, EMBO Mol Med (2012) 4(8): 691-704.
Vidale et al., The catalytic and the RNA subunits of human telomerase are required to immortalize equid primary fibroblasts, Chromosoma (2012) 121:475-488.
Sinn et al., Gene therapy progress and prospects: development of improved lentiviral and retroviral vectors—design, biosafety, and production, Gene Ther. Jul. 2005;12(14):1089-98.
Yamaguchi et al., Mutations in TERT, the gene for telomerase reverse transcriptase, in aplastic anemia, N Engl J Med. Apr. 7, 2005;352(14):1413-24.
Bachand et al., Expression of hTERT and hTR in cis reconstitutes and active human telomerase ribonucleoprotein, RNA. May 2000;6(5):778-84.
Li et al., Expression and suppression of human telomerase RNA, Cold Spring Harb Symp Quant Biol. 2006;71:211-5.
Prel et al., Highly efficient in vitro and in vivo delivery of functional RNAs using new versatile MS2-chimeric retrovirus-like particle, Mol Ther Methods Clin Dev. Oct. 21, 2015;2:15039.
Shaw et al., Design and Potential of Non-Integrating Lentiviral Vectors, Biomedicines. Mar. 2014; 2(1): 14-35.
Chen et al., Episomal lentiviral vectors confer erythropoietin expression in dividing cells, Plasmid. Mar. 2017;90:15-19.
Delluc-Clavieres et al., Efficient gene transfer in skeletal muscle with AAV-derived bicistronic vector using the FGF-1 IRES, Gene Ther. Aug. 2008;15(15):1090-8.
Harley, Telomerase and cancer therapeutics, Nat Rev Cancer. Mar. 2008;8(3):167-79.
Asokan et al., The AAV Vector Toolkit: Poised at the Clinical Crossroads, Molecular Therapy vol. 20 No. 4, 699-708 Apr. 2012.

\* cited by examiner

*Primary Examiner* — Kimberly Chong
(74) *Attorney, Agent, or Firm* — Bret E. Field; Bozicevic, Field & Francis LLP

(57) ABSTRACT

Methods of treating an age-related disorder in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

19 Claims, 7 Drawing Sheets

Specification includes a Sequence Listing.

ENHANCING HEALTH IN MAMMALS USING TELOMERASE REVERSE TRANSCRIPTASE GENE THERAPY

The improvement of health during aging is of interest in aging research. Markers of aging include conditions such as epithelial barrier fitness, osteoporosis, glucose intolerance with insulin insensitivity, loss of memory, and neuromuscular degeneration associated with loss of neuromuscular coordination. For example, bone loss is a well-characterized sign of the aging progress both in mammals including humans which results from bone resorption due to osteoblast insufficiency. Therefore, methods that increase life span and ameliorate various age-related parameters are of interest.

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 3' end of DNA in the telomere region, where hTER serves as the template for nucleotide incorporation, and TERT as the catalyst. Both the catalytic protein component and the RNA template component of telomerase are activity-limiting components.

SUMMARY

Methods of treating an age-related disorder or condition in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
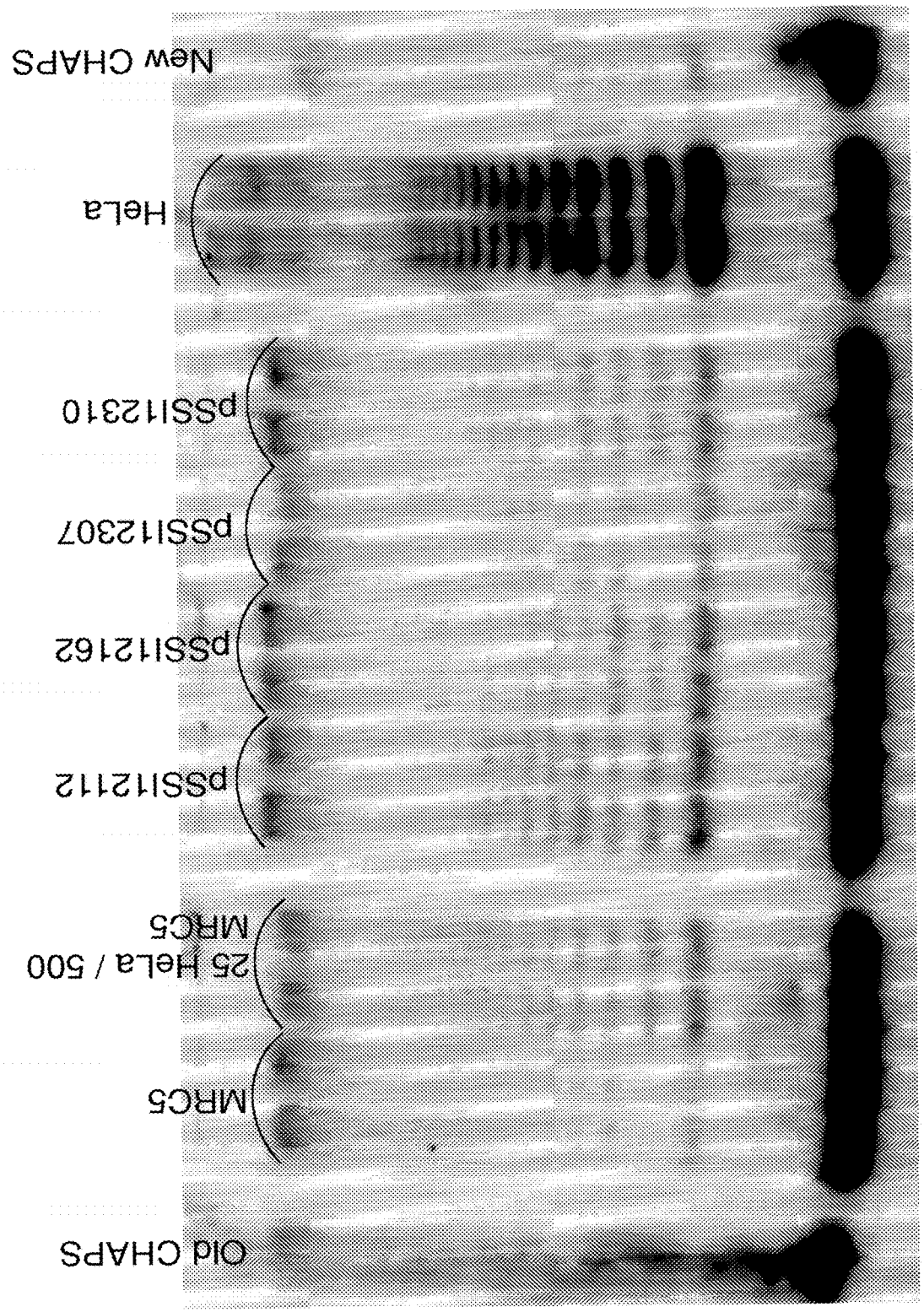
FIG. 1 depicts the results of a TRAP Assay using the vectors pSSI12112, pSSI12162, pSSI12307 and pSSI12310 where sample cells are collected at 7 days post BSD selection, 17 days post infection.

As summarized above, aspects of the invention include methods of treating an age-related disorder in a subject. Aspects of the methods include administering to the subject a nucleic acid vector including a coding sequence for telomerase reverse transcriptase (TERT). In some cases, the vector may include a coding sequence for telomerase RNA (TR). Gene therapy methods that utilize the subject vectors are also provided. Embodiments of the invention include compositions, e.g., nucleic acid vectors and kits, etc., that find use in the subject methods.

The subject methods may lead to increase the expression of telomerase reverse transcriptase and/or telomerase RNA when administered to adult mammals. Administration of the vectors to the subject may extend the lifespan of the subject (e.g., average or maximum lifespan), and may ameliorate one or more markers of ageing, including but not limited to epithelial barrier fitness, osteoporosis, glucose intolerance with insulin insensitivity, loss of memory, and neuromuscular degeneration associated with loss of neuromuscular coordination. The effect may be achieved without increasing the incidence of cancer (malignant neoplastic disease), as assessed by the number of spontaneous neoplasms evident among the population treated.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Vectors

As summarized above, one aspect of the invention is a nucleic acid vector. Application of the subject vector to a subject, e.g. using any convenient method such as a gene therapy method, may result in expression of one or more coding sequences of interest in cells of the subject, to produce a biologically active product that may modulate a biological activity of the cell. In some cases, the vector is a nucleic acid vector comprising a coding sequence for telomerase reverse transcriptase (TERT). In some cases, the nucleic acid vector comprises a coding sequence for one or more telomerase components, such as TERT and telomerase RNA (TR). In some embodiments, the vector does not include a cancer suppressing sequence.

In some instances, the vector comprises a coding sequence for telomerase reverse transcriptase (TERT) suitable for use in gene therapy. Gene therapy vectors of interest include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. In some cases, TERT is encoded by the nucleic acid sequence as set forth in SEQ ID NO:1 of WO2012001170 or SEQ ID NO:3 of WO2012001170, or is an active fragment or functional equivalent of TERT. In some instances, the vector include a regulatory sequence which is a constitutive promoter such as the cytomegalovirus (CMV) promoter.

The TERT and/or TR sequence used in the gene therapy vector may be derived from the same species as the subject. Any convenient TERT and/or TR sequences, or fragments or functional equivalents thereof, may be utilized in the subject vectors, including sequences from any convenient animal, such as a primate, ungulate, cat, dog, or other domestic pet or domesticated mammal, rabbit, pig, horse, sheep, cow, or a human. For example, gene therapy in humans may be carried out using the human TERT sequence. In some embodiments, the TERT and/or TR sequence is not a murine sequence.

As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to a parent TERT sequence. Functional equivalents may be artificial or naturally-occurring. For example, naturally-occurring variants of the TERT sequence in a population fall within the scope of functional equivalent. TERT sequences derived from other species also fall within the scope of the term "functional equivalent", e.g., a murine TERT sequence. In a particular embodiment, the functional equivalent is a nucleic acid with a nucleotide sequence having at least 75%, 80%, 85%, 90%, 95%, 96%, 97%, 98%, 99%, 99.5%, 99.9% identity to the parent sequence. In a further embodiment, the functional equivalent is a polypeptide with an amino acid sequence having at least 75%, 80%, 85%, 90%, 95%, 96%, 97%, 98%, 99%, 99.5%, 99.9% identity to a parent sequence. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to a parent sequence.

The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the parent amino acid sequence, but that show little homology to the parent nucleic acid sequence because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in the parent polynucleotide sequence or the amino acid sequence as set forth in parent polypeptide sequence. An active fragment may be of any size provided that TERT activity is retained. A fragment will have at least 75%, 80%, 85%, 90%, 95%, 96%, 97%, 98%, 99%, 99.5%, 100% identity to the parent sequence along the length of the alignment between the shorter fragment and longer parent sequence.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity. Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and PASTA (Lipman, D J; Pearson, W R (1985). "Rapid and sensitive protein similarity searches". Science 227 (4693): 1435-41; http://fasta.bioch.virginia.edu/fasta www2/fasta list2.shtml) and variations on these alignment programs.

The vector may further include one or more regulatory sequences. Any convenient regulatory sequences or promoter sequences may be utilized in the subject vectors, e.g., as described herein. In some embodiments, the regulatory sequence that is operatively linked to the coding sequence (e.g., the TERT and/or TR sequence) is the cytomegalovirus promoter (CMV), although any other convenient regulatory sequences may be utilized.

Viral Vectors

Any convenient viruses may be utilized in delivering the vector of interest to the subject. Viruses of interest include, but are not limited to a retrovirus, an adenovirus, an adeno-associated virus (AAV), a herpes simplex virus and a lentivirus. Viral gene therapy vectors are well known in the art, see e.g., Heilbronn & Weger (2010) Handb Exp Pharmacol. 197:143-70. Vectors of interest include integrative and non-integrative vectors such as those based on retroviruses, adenoviruses (AdV), adeno-associated viruses (AAV), lentiviruses, pox viruses, alphaviruses, and herpes viruses.

In some cases, non-integrative viral vectors, such as AAV, may be utilized. In one aspect, non-integrative vectors do not cause any permanent genetic modification. The vectors may be targeted to adult tissues to avoid having the subjects under the effect of constitutive telomerase expression from early stages of development. In some instances, non-integrative vectors effectively incorporate a safety mechanism to avoid over-proliferation of TERT expressing cells. The cells may lose the vector (and, as a consequence, the telomerase expression) if they start proliferating quickly.

Non-integrative vectors of interest include those based on adenoviruses (AdV) such as gutless adenoviruses, adeno-associated viruses (AAV), integrase deficient lentiviruses, pox viruses, alphaviruses, and herpes viruses. In certain embodiments, the non-integrative vector used in the invention is an adeno-associated virus-based non-integrative vector, similar to natural adeno-associated virus particles. Examples of adena-associated virus-based non integrative vectors include vectors based on any AAV serotype, i.e. AAVI, AAV2, AAV3, AAV4, AAV5, AAV6, AAV7, AAV8, AAV9, AAVIO, AAVII and pseudotyped AAV. Vectors of interest include those capable of transducing a broad range of tissues at high efficiency, with poor immunogenicity and an excellent safety profile. In some cases, the vectors transduce post-mitotic cells and can sustain long-term gene expression (up to several years) both in small and large animal models of age-related disorders.

Methods

As summarized above, aspects of the invention include methods of administering a nucleic acid vector to a subject. As such, aspects of the invention include contacting the subject with a viral vector, e.g., as described above, under conditions by which expression of one or more telomerase components (such as TERT and/or TR) in the subject results in a beneficial effect on one or more aspects of the subject's health, including increased longevity, delayed osteoporosis, improved epithelial barrier fitness, improved glucose tolerance, improved memory function, and improved neuromuscular coordination. In some cases, the subject did not develop increased incidence of cancer, illustrating the safety of this type of strategy.

In gene therapy methods, genes are directly inserted into cells affected by an age-related condition so that the function of the cells is normalized by expressing the inserted genes. The gene therapy methods may be used to prevent various diseases or age-related conditions or to reinforce treatment by inserting a specific gene into a body cell and granting a new function to the body cell. One aspect in the treatment of such conditions using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency. A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting the subject (e.g., a human) with the recombinant virus, which can be mass produced in vitro. In some cases, an adenovirus can be effectively used for the gene therapy by using a mechanism of transporting the gene into the nucleus of the target cell with a high efficiency. In addition, retroviruses are being used in many internationally permissible clinical trials (Wiley—The Journal of Gene Medicine Website: http://www.wiley.co.uk/genetherapy). Retroviruses are effective for gene therapy when inserted into cell chromosomal DNA to allow long term expression of the desired protein.

In certain instances, the expression of the TERT and/or TR following gene therapy according to the invention persists for a time of one or more weeks, such as one or more months, e.g., several months to several years.

When treating specific age related disorders, it is advantageous to target the treatment to the effected tissues. The serotype of the capsid protein of the gene therapy vector may thus be selected based on the desired site of gene therapy, e.g., skeletal muscle tissue for treating neuromuscular coordination.

Any convenient methods may be employed. Methods and vectors of interest that may be adapted for use in the subject invention include, but are not limited to the methods and vectors of WO 2012/001170 and Vidale et al. "The catalytic and the IRNA subunits of human telomerase are required to immortalize equid primary fibroblasts." Chromosoma. 2012 Jul. 14. Epub, the disclosures of which are herein incorporated by reference.

In some embodiments, the method of treatment is a gene therapy method and/or the nucleic acid vector used is a gene therapy vector. Gene therapy methods and vectors are well known in the art and generally include delivering a nucleic acid encoding a therapeutically active protein to a subject. The nucleic acid may be delivered in a number of ways including delivering naked DNA such as plasmid or minicircles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. In certain embodiments, this aspect of the invention does not extend to human subjects. Expression of TERT or TR can be induced at a later date following transformation, for example, once the subject is an adult or an aged adult, or begins to show signs of age-related disorders. Suitable inducible expression systems are known in the art and include the CRE-LOX recombinase based system and the tetracycline-regulated system.

In some embodiments, the present invention is limited to the expression of TERT an/or TR in adult or aged subjects. In certain embodiments, the methods and vectors are utilized with post-mitotic cells within the subjects, and avoid any increased incidence of cancer.

Any convenient subjects may be treated according to the subject methods. The subject may be an adult animal, such as an adult mammal. The mammal may be a primate, ungulate, cat, dog, domestic pet or domesticated mammal. In some cases, the mammal may be a rabbit, pig, horse, sheep, cow, cat or dog, or a human. In certain embodiments the subject is not a murine mammal. An adult subject treated according to the invention may be aged. The term "aged" is applied to an individual who is older than the period of life during which the individuals of its species are generally healthy and free of chronic illness. According to the present application, an "adult" should be a fully developed individual who has attained reproductive ability, is fertile, or who evidences secondary sex characteristics. As used herein, the term adult when applied to humans, for example, describes early adulthood commencing at around 20 years of age and extending to 39; middle adulthood (40 to 59) and late adulthood (60+). As a comparison, a one year old mouse can be considered to be approximately equivalent in age to a 45 year old human. A 2 year old mouse can be considered to be approximately equivalent to an 80 year old human.

The particular protocol that is employed may vary. Administration of the vectors may be achieved using any convenient protocol. Vectors as described above (e.g., retroviral vectors and lentiviral vectors) may be administered in vivo to subjects by any convenient route. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein. Alternatively, vectors of the invention can be administered ex vivo or in vitro to cells or tissues using any convenient transfection techniques.

The vectors of the invention can also be transduced into host cells, including but not limited to, embryonic stem cells, somatic stem cells, or progenitor cells. Examples of progenitor host cells which can be transduced by the vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

In some embodiments, the method does not include concomitant use of a cancer suppressor.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the vectors of the invention. In one embodiment, the composition includes a vector in a therapeutically effective amount sufficient to treat or prevent (e.g. ameliorate one or more age-related conditions), and a pharmaceutically acceptable carrier. A "therapeutically effective amount" refers to an amount effective, at dosages and for periods of time necessary, to achieve the desired therapeutic result, such as treatment or amelioration of an age-related condition. A therapeutically effective amount of vector may vary according to factors such as the disease state, age, sex, and weight of the individual, and the ability of the viral vector to elicit a desired response in the individual. Dosage regimens may be adjusted to provide the optimum therapeutic response. A therapeutically effective amount is also one in which any toxic or detrimental effects of the viral vector are outweighed by the therapeutically beneficial effects. The potential toxicity of the viral vectors of the invention can be assayed using cell-based assays or art recognized animal models and a therapeutically effective modulator can be selected which does not exhibit significant toxicity. In a preferred embodiment, a therapeutically effective amount of a viral vector is sufficient to treat or ameliorate one or more age-related conditions in as subject.

Sterile injectable solutions can be prepared by incorporating viral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

It is to be noted that dosage values may vary with the severity of the condition to be ameliorated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In Vitro Methods

Also included are in vitro methods, where the subject vectors, e.g., as described above are contacted with a sample. The particular protocol that is employed may vary, e.g., depending on the sample. For in vitro protocols, contact of the vector with the sample may be achieved using any convenient protocol. In some instances, the sample includes cells that are maintained in a suitable culture medium, and the vector is introduced into the culture medium. Depending upon the nature of the vector (e.g., a viral vector), the response desired, the manner of contacting or administration, the number of cells present, various protocols may be employed. The term "sample" as used herein relates to a material or mixture of materials, typically, although not necessarily, in fluid form, containing one or more components of interest.

Utility

The vectors and methods of the invention, e.g., as described above, find use in a variety of applications. Applications of interest include, but are not limited to: research applications and therapeutic applications. Methods of the invention find use in a variety of different applications including any convenient application where the subject is experiencing one or more age-related conditions. In some cases, age-related disorders or conditions that may be modulated or ameliorated using the subject vectors and methods include, but are not limited to, osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

The subject vectors and methods find use in a variety of research applications. The subject vectors and methods may be used to analyze the role of telomerase various biological processes including age-related disorders and conditions.

The subject vectors and methods find use in a variety of therapeutic applications. Therapeutic applications of interest include those applications in which the subject is suffering from one or more age-related disorders or conditions. As such, the subject vectors find use in the treatment of a variety of different age-related conditions in various subjects, and may lead to an extended lifespan. For example, the subject vectors and methods may find use in regulated gene therapy.

Extended lifespan may be an increase in the maximum lifespan possible for any particular species of subject. Extended lifespan may be an increase in the average lifespan of an individual of that species who reaches adulthood. Thus, extended lifespan may be a 5%, 10%, 15%, 20% or more increase in maximum lifespan and/or a 5%, 10%, 15%, 20% or more increase in average lifespan.

The application of the invention extends the period of time for which an individual is generally healthy and free of chronic illness and/or the invention ameliorates disorders that appear often in aged and ageing adult population, including reduced epithelial barrier fitness, osteoporosis, glucose intolerance and neuromuscular degeneration associated with loss of neuromuscular coordination. These are well established indicators of ageing progression.

Accordingly, the invention has beneficial effects in at least one of the following group: reducing the incidence of cancer, on delaying and/or ameliorating osteoporosis, improving epithelial barrier fitness, improving glucose tolerance, improving memory function, and improving neuromuscular coordination. The amelioration of age-related disorders provided by the invention can be as a result of reduction of symptoms in an affected subject or a reduction of incidence of the disease or disorder in a population as compared to an untreated population. The application of gene therapy according to the invention has the effect of treating and/or preventing various age-related conditions and diseases, as assessed by particular markers and disorders of ageing. In a further aspect, therefore, the invention refers to a gene therapy method or the used of a nucleic acid vector as described above, for use in the treatment or prevention in a subject of at least a disorder or marker of ageing that is selected from the group of reduced epithelial barrier fitness, osteoporosis, arthrosis, glucose intolerance, insulin resistance, loss of memory, loss of neuromuscular coordination, increase in cardiovascular disease, decrease in heart, circulatory or lung function and decrease in longevity, or combinations thereof. The gene therapy ameliorates at least one marker of ageing, selected for example, from the group of reduced epithelial barrier fitness, osteoporosis, arthrosis, glucose intolerance, insulin resistance, cardiovascular disease, reduced heart and circulatory function, reduced lung function, loss of memory, loss of neuromuscular coordination or decrease of longevity or combinations thereof.

Kits

Aspects of the invention further include kits, where the kits include one or more components employed in methods of the invention, e.g., vectors, as described herein. In some embodiments, the subject kit includes a vector (as described herein), and one or more components selected from a promoter, a virus, a cell, and a buffer. Any of the components described herein may be provided in the kits, e.g., cells, constructs (e.g., vectors) encoding for TERT and/or TR, components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a virus particle that includes a nucleic acid vector, e.g., as described above. Any convenient virus particles may be utilized, and include viral vector particles described above.

Aspects of the invention include providing a cell that includes a nucleic acid vector. The cell that is provided with the vector of interest may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non-human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Construction of Vectors
pSSI14342:
Adeno vector containing hTR and hTERT was constructed.
LITR-U1-hTR-CMV-hTERT-SV40 pA-RITR
Region base locations:
Adeno RITR: 2928-3030
U1 promoter: 6459-6668
hTR: 6850-7300
U1-3'box: 7458-7472
CMV promoter: 7485-8073
Kozak: 8082-8098
hTERT: 8087-11482
SV40 pA: 11558-11679
Adeno LITR: 5973-6075
pSSI10902:
Lentiviral vector pSSI10902 was constructed and contains hTERT, Puro gene (for selection of infected cells) and AmCyan gene (a fluorescent protein for color). In pSSI10902, hTERT is expressed using the CMV promoter, Puro gene is expressed using the SV40 promoter, and AmCyan gene is expressed using the CMV promoter. Below is shown the schematic for the pSSI10902 expression cassette. The sequence of this entire vector is also provided (SEQ ID NO: 2).
pSSI10902:   5'-LTR-CMV-hTERT-SV40-Puro-CMV-AmCyan-LTR-3'
Region base locations:
5' LTR: 230-410
CMV promoter: 1883-2374
Kozak: 2627-2643
hTERT: 2632-6027
SV40 promoter: 6053-6286
CMV promoter: 7242-7830
AmCyan: 7891-8577
3' LTR: 9315-9495
pSSI12112:
The lentiviral vector pSSI12112 was constructed as a dual vector containing both hTR and hTERT in the same vector. hTR is expressed using the U1 promoter and hTERT is expressed using the CMV promoter. Note: this plasmid also contains the BSD gene being expressed by the PGK promoter which allows selection for cells infected with the lentivirus created using this plasmid. Below is shown a schematic of the expression cassette for pSSI12112. The sequence of this entire vector is also attached (SEQ ID NO:3).
pSSI12112:   5'-LTR-U1-hTR-PGK-BSD-CMV-hTERT-LTR-3'

Region base locations:
5' LTR: 230-410
U1 promoter: 1876-2085
hTR: 2267-2717
U1-3'box: 2875-2889
PGK promoter: 2916-3421
BSD: 3499-3894
CMV promoter: 4023-4611
Kozak: 4620-4636
hTERT: 4625-8020
3' LTR: 8200-8380

Further vectors were constructed and tested as described herein.

pSSI12112=LTR-U1-hTR-PGK-BSD-CMV-TSS-hTERT-LTR
pSSI12162=LTR-U1-hTR-PGK-BSD-CMV-TSS-nonhTERT-LTR
pSSI12307=LTR-PGK-BSD-CMV-TSS-hTERT-LTR
pSSI12310=LTR-PGK-BSD-CMV-TSS-nonhTERT-LTR The viral vectors are tested in vitro or in vivo using any convenient methods. Methods of interest that are adapted for use in testing the viral vectors described herein include those methods described by WO 2012/001170 and Vidale et al. "The catalytic and the RNA subunits of human telomerase are required to immortalize equid primary fibroblasts." Chromosoma. 2012 Jul. 14. Epub.
Project 2273 pSSI12112 (hTR+hTERT) was tested in MRC5 cells. At 7 days post BSD selection, the TRAP activity from pSSI12112 is slightly stronger than the other 3 test samples (pSSI12162 (hTR+non-functional hTERT), pSSI12307 (hTERT), and pSSI12310 (non-functional hTERT)). At 14 days post selection, the pSSI12112 TRAP activity is less than the other 3 samples and eventually diminishes to no TRAP signal at 21 days post BSD selection.

FIG. 1 depicts the results of a TRAP Assay using the vectors pSSI12112, pSSI12162, pSSI12307 and pSSI12310 where sample cells are collected at 7 days post BSD selection, 17 days post infection.

Figure 2:
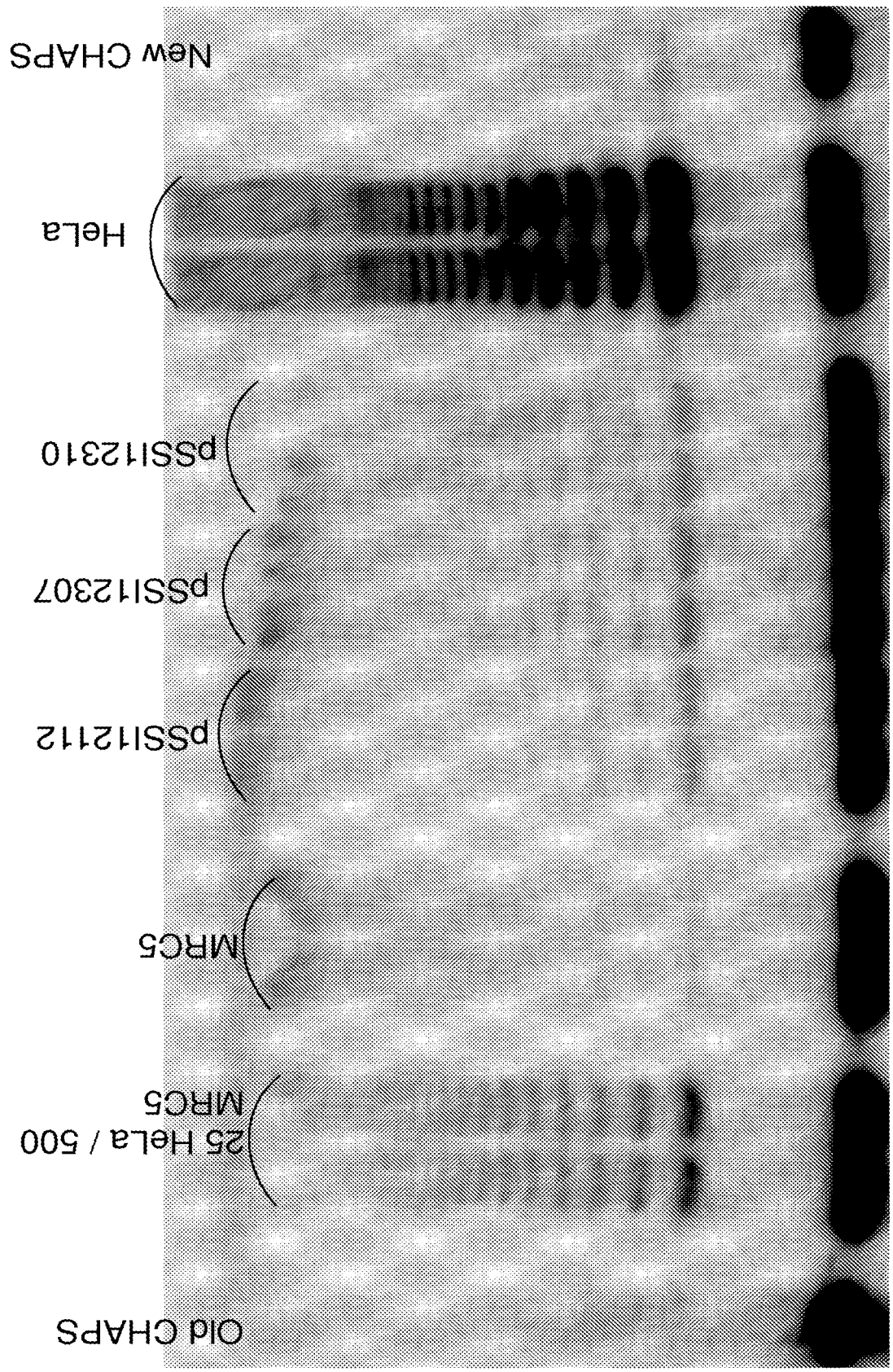
FIG. 2 depicts the results of a TRAP Assay using the vectors pSSI12112, pSSI12307 and pSSI12310 where sample cells are collected at 14 days post BSD selection, 24 days post infection.

FIG. 2 depicts the results of a TRAP Assay using the vectors pSSI12112, pSSI12307 and pSSI12310 where sample cells are collected at 14 days post BSD selection, 24 days post infection.

Figure 3:
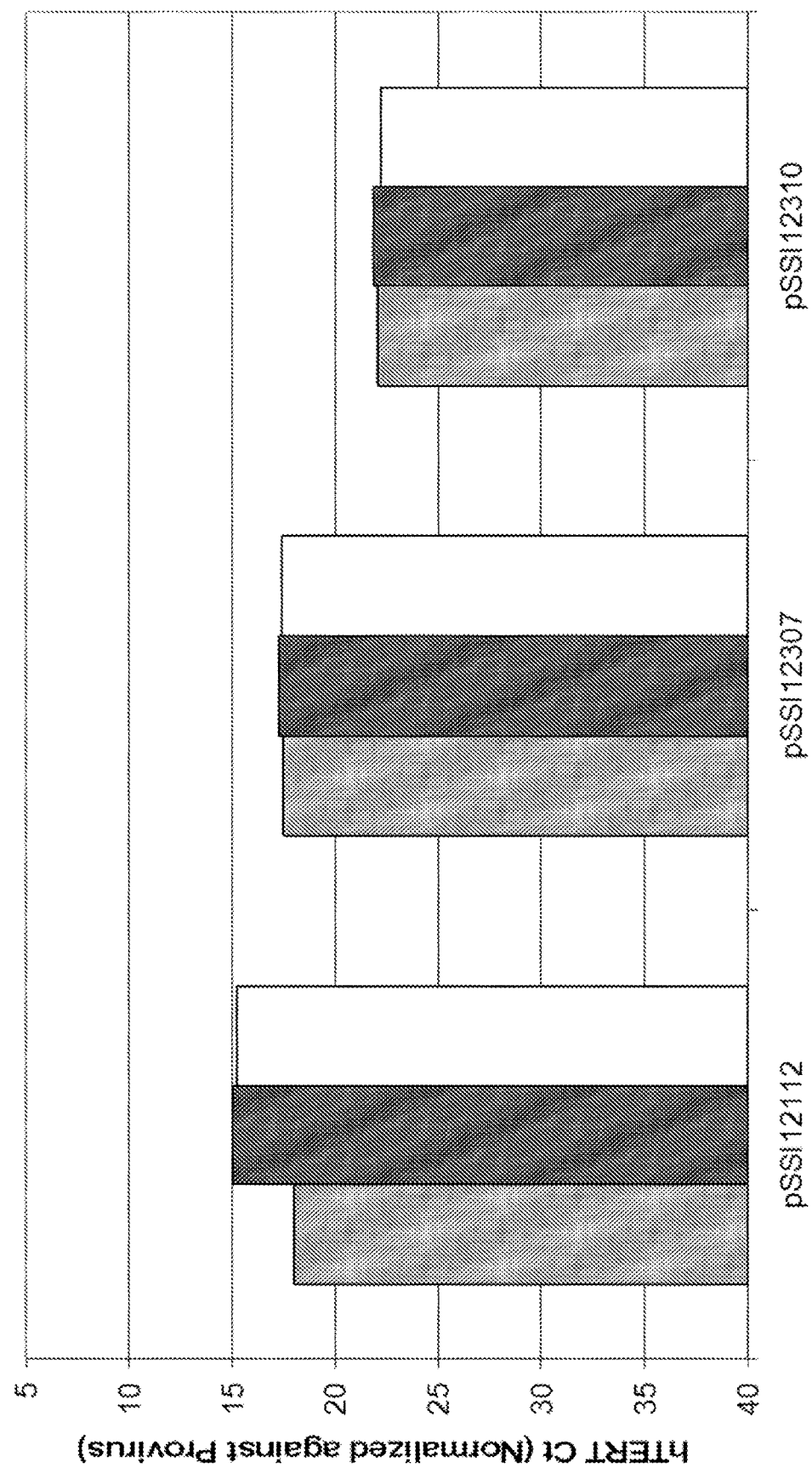
FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

Figure 4:
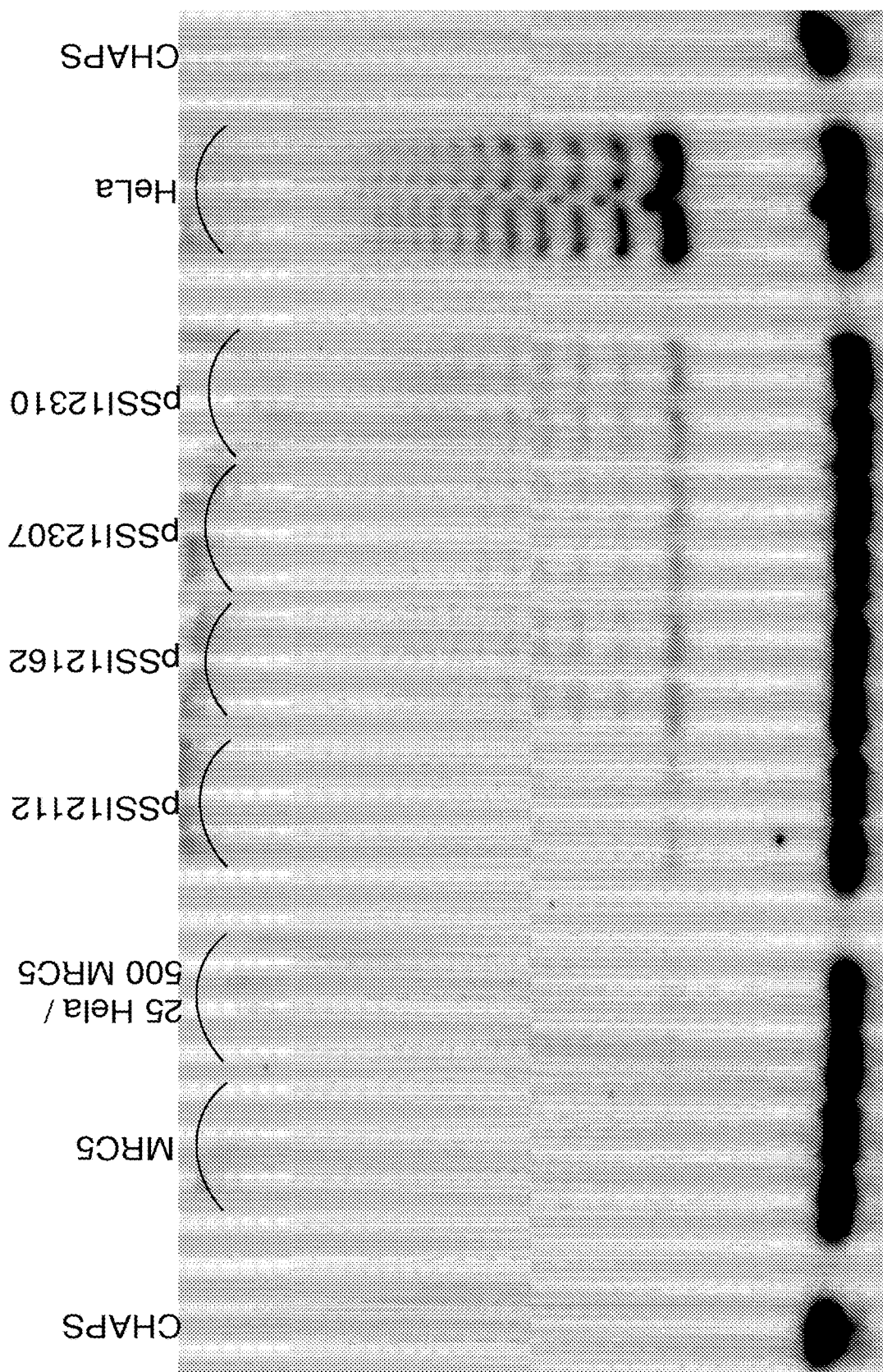
FIG. 4 depicts the results of a TRAP Assay using the vectors pSSI12112, pSSI12162, pSSI12307 and pSSI12310 where sample cells are collected at 21 days post BSD selection, 31 days post infection.

FIG. 4 depicts the results of a TRAP Assay using the vectors pSSI12112, pSSI12162, pSSI12307 and pSSI12310 where sample cells are collected at 21 days post BSD selection, 31 days post infection.

Figure 5:
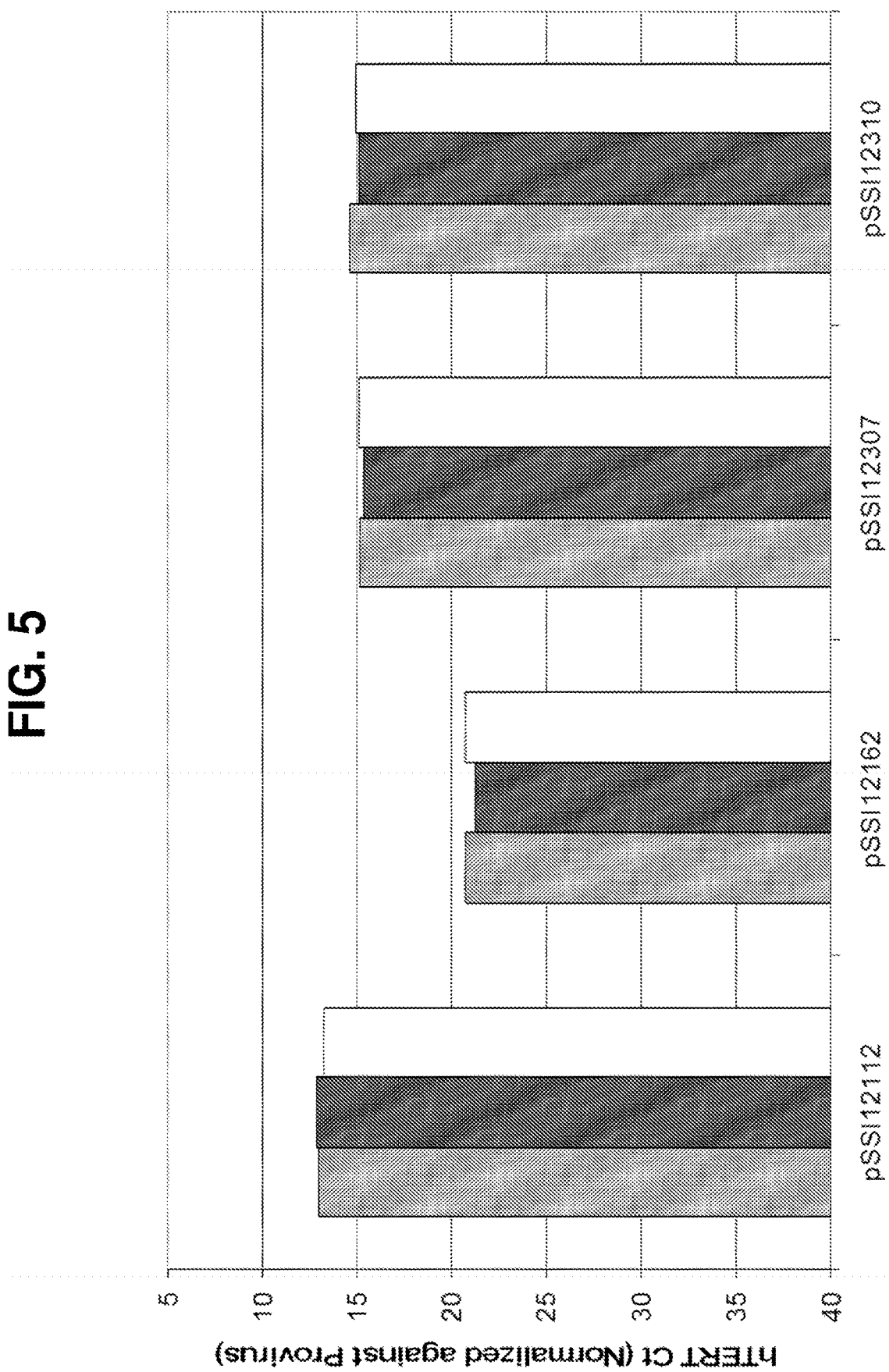
FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

Figure 6:
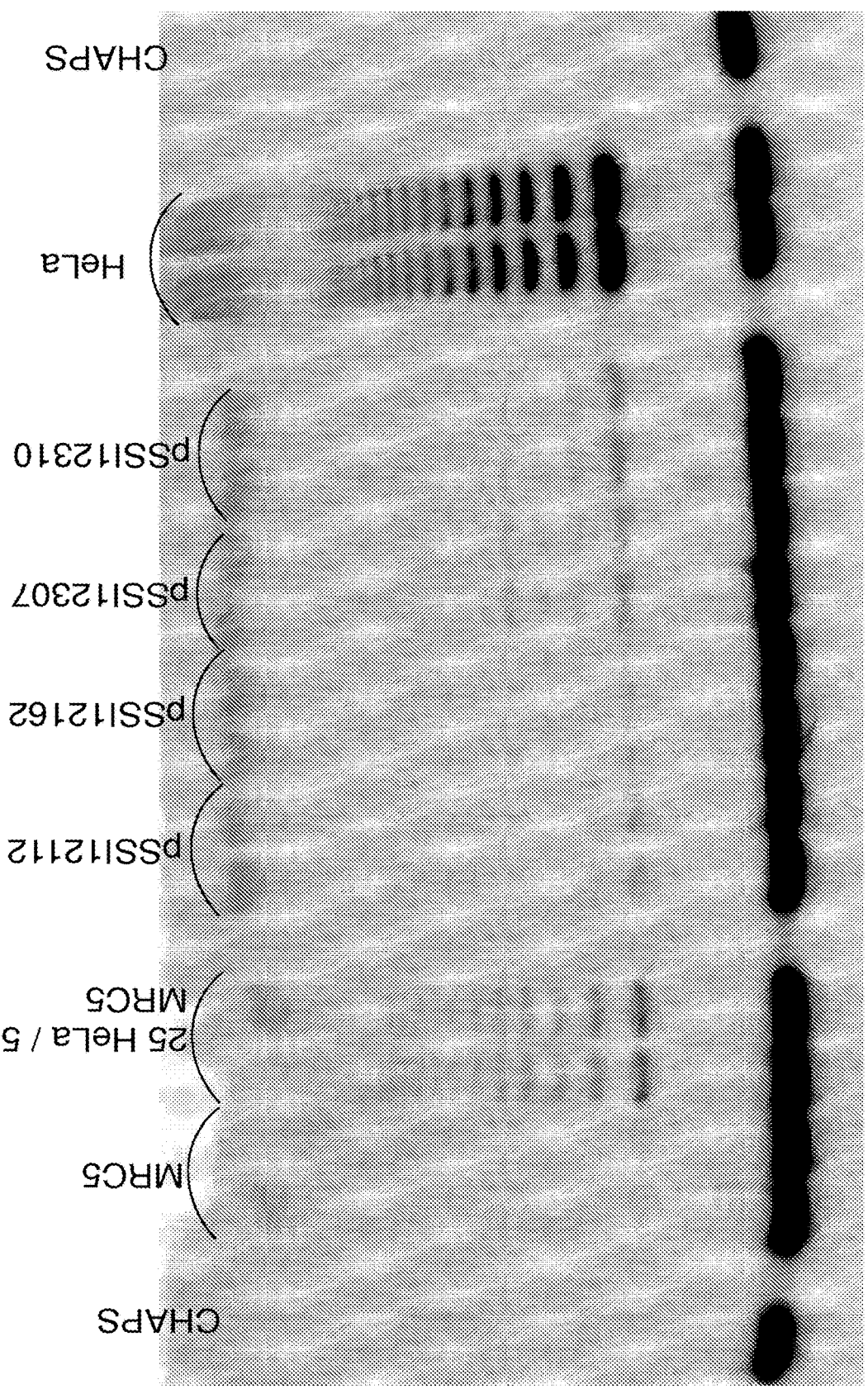
FIG. 6 depicts the results of a TRAP Assay using the vectors pSSI12112, pSSI12162, pSSI12307 and pSSI12310 where sample cells are collected at 49 days post BSD selection, 59 days post infection.

FIG. 6 depicts the results of a TRAP Assay using the vectors pSSI12112, pSSI12162, pSSI12307 and pSSI12310 where sample cells are collected at 49 days post BSD selection, 59 days post infection.

Figure 7:
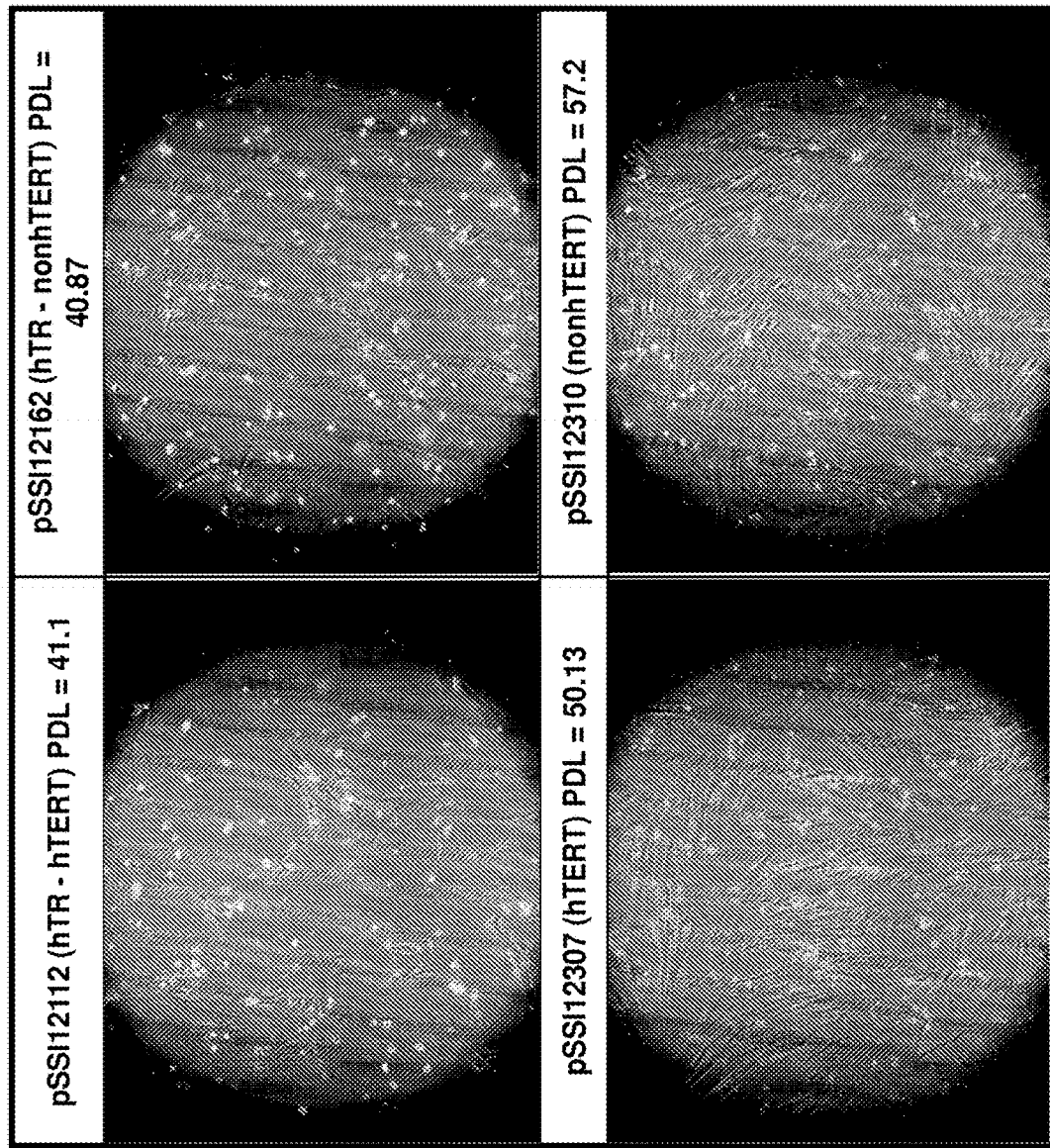
FIG. 7 depicts images comparing cell growth of cells that were maintained in 1.5 ug/ml BSD for 55 days post selection using the vectors pSSI12112, pSSI12162, pSSI12307 and pSSI12310.

FIG. 7 depicts images comparing cell growth of cells that were maintained in 1.5 ug/ml BSD for 55 days post selection using the vectors pSSI12112, pSSI12162, pSSI12307 and pSSI12310.

```
pSSI14342 (SEQ ID NO: 1)
TCACAGAACCCTAGTATTCAACCTGCCACCTCCCTCCCAACACACAGAGTACACAGTCCTTTCTC

CCCGGCTGGCCTTAAAAAGCATCATATCATGGGTAACAGACATATTCTTAGGTGTTATATTCCACA

CGGTTTCCTGTCGAGCCAAACGCTCATCAAGTGATATTAATAAACTCCCCGGGCAGCTCACTTAA

GTTCATGTCGCTGTCCAGCTGCTGAGCCACAGGCTGCTGTCCAACTTGCGGTTGCTTAACGGGC

GGCGAAGGAGAAGTCCACGCCTACATGGGGGGAGAGTCATAATCGTGCATCAGGATAGGGCGG

TGGTGCTGCAGCAGCGCGCGAATAAACTGCTGCCGCCGCCGCTCCGTCCTGCAGGAATACAACA

TGGCAGTGGTCTCCTCAGCGATGATTCGCACCGCCCGCAGCATAAGGCGCTTGTCCTCCGGGCA

CAGCAGCGCACCCTGATCTCACTTAAATCAGCACAGTAACTGCAGCACAGCACCACAATATTGTT

CAAAATCCCACAGTGCAAGGCGCTGTATCCAAAGCTCATGGCGGGGACCACAGAACCCACGTGG

CCATCATACCACAAGCGCAGGTAGATTAAGTGGCGACCCCTCATAAACACGCTGGACATAAACAT

TACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCCGCCGGGNTATACACTGCAGGG

AACCGGGACTTGGACAATGACAAGTGGGAGAGCCCAGGACTCGTAACCATGGATCATCATGCTC

GTCATGATATCAATGTTGGCACAACACAGGCACACGTGCATACACTTCCTCAGGATTACAAGCTC

CTCCCGCGTTAGAACCATATCCCAGGGAACAACCCATTCCTGAATCAGCGTAAATCCCACACTGC

AGGGAAGACCTCGCACGTAACTCACGTTGTGCATTGTCAAAGTGTTACATTCGGGCAGCAGCGG

ATGATCCTCCAGTATGGTAGCGCGGGTTTCTGTCTCAAAAGGAGGTAGACGATCCCTACTGTACG

GAGTGCGCCGAGACAACCGAGATCGTGTTGGTCGTAGTGTCATGCCAAATGGAACGCCGGACGT

AGTCATATTTCCTGAAGCAAAACCAGGTGCGGGCGTGACAAACAGATCTGCGTCTCCGGTCTCG

CCGCTTAGATCGCTCTGTGTAGTAGTTGTAGTATATCCACTCTCTCAAAGCATCCAGGCGCCCCC
```

-continued

```
TGGCTTCGGGTTCTATGTAAACTCCTTCATGCGCCGCTGCCCTGATAACATCCACCACCGCAGAA

TAAGCCACACCCAGCCAACCTACACATTCGTTCTGCGAGTCACACACGGGAGGAGCGGGAAGAG

CTGGAAGAACCATGTTTTTTTTTTATTCCAAAAGATTATCCAAAACCTCAAAATGAAGATCTATTA

AGTGAACGCGCTCCCCTCCGGTGGCGTGGTCAAACTCTACAGCCAAAGAACAGATAATGGCATT

TGTAAGATGTTGCACAATGGCTTCCAAAAGGCAAACGGCCCTCACGTCCAAGTGGACGTAAAGG

CTAAACCCTTCAGGGTGAATCTCCTCTATAAACATTCCAGCACCTTCAACCATGCCCAATAATTC

TCATCTCGCCACCTTCTCAATATATCTCTAAGCAAATCCCGAATATTTAAGTCCGGGCCATTGTAA

AAAATTTGGCTCCAGAGCGCCCTCCACCTTCAGCCTCAAGCAGCGAATCATGATTGCAAAAATTC

AGGTTCCTCACAGACCTGTATAAGATTCAAAAGCGGAACATTAACAAAAATACCGCGATCCCGTA

GGTCCCTTCGCAGGGCCAGCTGAACATAATCGTGCAGGTCTGCACGGACCAGCGCGGCCACTT

CCCCGCCAGGAACCATGACAAAAGAACCCACACTGATTATGACACGCATACTCGGAGCTATGCTA

ACCAGCGTAGCCCCGATGTAAGCTTGTTGCATGGGCGGCGATATAAAATGCAAGGTGCTGCTCA

AAAAATCAGGCAAAGCCTCGCGCAAAAAGAAAGCACATCGTAGTCATGCTCATGCAGATAAAGG

CAGGTAAGCTCCGGAACCACCACAGAAAAAGACACCATTTTTCTCTCAAACATGTCTGCGGGTTT

CTGCATAAACACAAAATAAAATAACAAAAAAACATTTAAACATTAGAAGCCTGTCTTACAACAGGAA

AAACAACCCTTATAAGCATAAGACGGACTACGGCCATGCCGGCGTGACCGTAAAAAAACTGGTCA

CCGTGATTAAAAAGCACCACCGACAGCTCCTCGGTCAGTCCGGAGTCATAATGTAAGACTCGGTA

AACACATCAGGTTGATTCACATCGGTCAGTGTTAAAAAGCGACCGAAATAGCCNGGGGGAATACA

ATACCCGCAGGCGTAGAGACAACATTACAGCCCCCATAGGAGGTATAACAAAATTAATAGGAGAG

AAAAACACATAAACACCTGAAAAACCCTCCTGCCTAGGCAAAATAGCACCCTCCCGCTCCAGAAC

AACATACAGCGCTTCCACAGCGGCAGCCATAACAGTCAGCCTTACCAGTAAAAAAGAAAACCTAT

TAAAAAAACACCACTCGACACGGCACCAGCTCAATCAGTCACAGTGTAAAAAAGGGCCAAGTGCA

GAGCGAGTATATATAGGACTAAAAAATGACGGTAACGGTTAAAGTCCACAAAAAACACCCAGAAA

ACCGCACGCGAACCTACGCCCAGAAACGAAAGCCAAAAAACCCACAACTTCCTCAAATCGTCACT

TCCGTTTTCCCACGTTACGTCACTTCCCATTTTAAGAAAACTACAATTCCCAACACATACAAGTTAC

TCCGCCCTAAAACCTACGTCACCCGCCCCGTTCCCACGCCCCGCGCCACGTCACAAACTCCACC

CCCTCATTATCATATTGGCTTCAATCCAAAATAAGGTATATTATTGATGATGTTAATTAACATGCAT

GGATCCATATGCGGTGTGAAATACCGCACAGATGCGTAAGGAGAAAATACCGCATCAGGCGCTC

TTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGGCT

CCGCCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCGT

TCAGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCTGCGCT

CTGCTGAAGCCAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCACGTTAAGGGATTTTG
```

-continued
```
GTCATGAGATTATCAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAATA

GTTTGCGCAACGTTGTTGCCATTGCTGCAGCCATGAGATTATCAAAAGGATCTTCACCTAGATC

CTTTTCACGTAGAAAGCCAGTCCGCAGAAACGGTGCTGACCCCGGATGAATGTCAGCTACTGGG

CTATCTGGACAAGGGAAAACGCAAGCGCAAAGAGAAAGCAGGTAGCTTGCAGTGGGCTTACATG

GCGATAGCTAGACTGGGCGGTTTTATGGACAGCAAGCGAACCGGAATTGCCAGCTGGGGCGCC

CTCTGGTAAGGTTGGGAAGCCCTGCAAAGTAAACTGGATGGCTTTCTTGCCGCCAAGGATCTGAT

GGCGCAGGGGATCAAGCTCTGATCAAGAGACAGGATGAGGATCGTTTCGCATGATTGAACAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTT

TTGTCAAGACCGACCTGTCCGGTGCCCTGAATGAACTGCAAGACGAGGCAGCGCGGCTATCGTG

GCTGGCCACGACGGGCGTTCCTTGCGCAGCTGTGCTCGACGTTGTCACTGAAGCGGGAAGGGA

CTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCTTGA

CGAGTTCTTCTGAATTTTGTTAAAATTTTGTTAAATCAGCTCATTTTTTAACCAATAGGCCGAAAT

CGGCAACATCCCTTATAAATCAAAAGAATAGACCGCGATAGGGTTGAGTGTTGTTCCAGTTTGGA

ACAAGAGTCCACTATTAAAGAACGTGGACTCCAACGTCAAAGGGCGAAAAACCGTCTATCAGGGC

GATGGCCCACTACGTGAACCATCACCCAAATCAAGTTTTTTGCGGTCGAGGTGCCGTAAAGCTCT

AAATCGGAACCCTAAAGGGAGCCCCCGATTTAGAGCTTGACGGGGAAAGCCGGCGAACGTGGC

GAGAAAGGAAGGGAAGAAAGCGAAAGGAGCGGGCGCTAGGGCGCTGGCAAGTGTAGCGGTCA

CGCTGCGCGTAACCACCACACCCGCGCGCTTAATGCGCCGCTACAGGGCGCGTCCATTCGCCA

TTCAGGATCGAATTAATTCTTAATTAACATCATCAATAATATACCTTATTTTGGATTGAAGCCAATAT

GATAATGAGGGGGTGGAGTTTGTGACGTGGCGCGGGGCGTGGGAACGGGGCGGGTGACGTAG

TAGTGTGGCGGAAGTGTGATGTTGCAAGTGTGGCGGAACACATGTAAGCGACGGATGTGGCAAA

AGTGACGTTTTTGGTGTGCGCCGGTGTACACAGGAAGTGACAATTTTCGCGCGGTTTTAGGCGG

ATGTTGTAGTAAATTTGGGCGTAACCGAGTAAGATTTGGCCATTTTCGCGGGAAAACTGAATAAG

AGGAAGTGAAATCTGAATAATTTTGTGTTACTCATAGCGCGTAATACTGGTACCGCGGCCGCCTC

GAGTCTAGAGATATCGAATTCAAGCTTAAGGTGCACGGCCCACGTGGCCACTAGTAATTTTTCTG

CAGAAAACGTACCCGGGGATCCTCTAGGATCCCACCGAAAGGTTGCTCCTTAACACAGGCTAAG

GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGGAC
```

```
TGGGCAAGGCACTGTCGGTGACATCACGGACAGGGCGACTTCTATGTAGATGAGGCAGCGCAG
AGGCTGCTGCTTCGCCACTTGCTGCTTCGCCACGAAGGAGTTCCCGTGCCCTGGGAGCGGGTTC
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG
GGCTCTGTCAGCCGCGGGTCTCTCGGGGGCGAGGGCGAGGTTCAGGCCTTTCAGGCCGCAGG
AAGAGGAACGGAGCGAGTCCCCGCGCGCGGCGCGATTCCCTGAGCTGTGGGACGTGCACCCA
GGACTCGGCTCACACATGCAGTTCGCTTTCCTGTTGGTGGGGGAACGCCGATCGTGCGCATCC
GTCACCCCTCGCCGGCAATGGGGGCTTGTGAACCCCCAAACCTGACTGACTGGGCCAGTGTGCT
GCAAATTGGCAGGAGACGTGAAGGCACCTCCAAAGTCGACTTTCTGGAGTTTCAAAAACAGACC
GTACGATGCATTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTGGTTTA
GTGAACCGTCAGATCCGCTAGCCCCACCATGCCGCGCGCTCCCCGCTGCCGAGCCGTGCGCTC
CCTGCTGCGCAGCCACTACCGCGAGGTGCTGCCGCTGGCCACGTTCGTGCGGCGCCTGGGGC
CCCAGGGCTGGCGGCTGGTGCAGCGCGGGGACCCGGCGGCTTTCCGCGCGCTGGTGGCCCAG
TGCCTGGTGTGCGTGCCCTGGGACGCACGGCCGCCCCCCGCCGCCCCCTCCTTCCGCCAGGTG
TCCTGCCTGAAGGAGCTGGTGGCCCGAGTGCTGCAGAGGCTGTGCGAGCGCGGCGCGAAGAAC
GTGCTGGCCTTCGGCTTCGCGCTGCTGGACGGGGCCCGCGGGGGCGCCCCCGAGGCCTTCAC
CACCAGCGTGCGCAGCTACCTGCCCAACACGGTGACCGACGCACTGCGGGGGAGCGGGGCGT
GGGGGCTGCTGTTGCGCCGCGTGGGCGACGACGTGCTGGTTCACCTGCTGGCACGCTGCGCG
CTCTTTGTGCTGGTGGCTCCCAGCTGCGCCTACCAGGTGTGCGGGCCGCCGCTGTACCAGCTC
GGCGCTGCCACTCAGGCCCGGCCCCCGCCACACGCTAGTGGACCCCGAAGGCGTCTGGGATG
CGAACGGGCCTGGAACCATAGCGTCAGGGAGGCCGGGGTCCCCCTGGGCCTGCCAGCCCCGG
GTGCGAGGAGGCGCGGGGGCAGTGCCAGCCGAAGTCTGCCGTTGCCCAAGAGGCCCAGGCGT
GGCGCTGCGCCTGAGCCGGAGCGGACGCCCGTTGGGCAGGGGTCCTGGGCCCACCCGGGCAG
GACGCGTGGACCGAGTGACCGTGGTTTCTGTGTGGTGTCACCTGCCAGACCCGCCGAAGAAGC
CACCTCTTTGGAGGGTGCGCTCTCTGGCACGCGCCACTCCCACCCATCCGTGGGCCGCCAGCA
CCACGCGGGCCCCCCATCCACATCGCGGCCACCACGTCCCTGGGACACGCCTTGTCCCCCGGT
GTACGCCGAGACCAAGCACTTCCTCTACTCCTCAGGCGACAAGGAGCAGCTGCGGCCCTCCTTC
CTACTCAGCTCTCTGAGGCCCAGCCTGACTGGCGCTCGGAGGCTCGTGGAGACCATCTTTCTGG
```

-continued

```
GTTCCAGGCCCTGGATGCCAGGGACTCCCCGCAGGTTGCCCCGCCTGCCCCAGCGCTACTGGC
AAATGCGGCCCCTGTTTCTGGAGCTGCTTGGGAACCACGCGCAGTGCCCCTACGGGGTGCTCCT
CAAGACGCACTGCCCGCTGCGAGCTGCGGTCACCCCAGCAGCCGGTGTCTGTGCCCGGGAGAA
GCCCCAGGGCTCTGTGGCGGCCCCCGAGGAGGAGGACACAGACCCCCGTCGCCTGGTGCAGC
TGCTCCGCCAGCACAGCAGCCCCTGGCAGGTGTACGGCTTCGTGCGGGCCTGCCTGCGCCGGC
TGGTGCCCCAGGCCTCTGGGGCTCCAGGCACAACGAACGCCGCTTCCTCAGGAACACCAAGA
AGTTCATCTCCCTGGGGAAGCATGCCAAGCTCTCGCTGCAGGAGCTGACGTGGAAGATGAGCGT
GCGGGGCTGCGCTTGGCTGCGCAGGAGCCCAGGGGTTGGCTGTGTTCCGGCCGCAGAGCACC
GTCTGCGTGAGGAGATCCTGGCCAAGTTCCTGCACTGGCTGATGAGTGTGTACGTCGTCGAGCT
GCTCAGGTCTTTCTTTTATGTCACGGAGACCACGTTTCAAAAGAACAGGCTCTTTTTCTACCGGAA
GAGTGTCTGGAGCAAGTTGCAAAGCATTGGAATCAGACAGCACTTGAAGAGGGTGCAGCTGCGG
GAGCTGTCGGAAGCAGAGGTCAGGCAGCATCGGGAAGCCAGGCCCGCCCTGCTGACGTCCAGA
CTCCGCTTCATCCCCAAGCCTGACGGGCTGCGGCCGATTGTGAACATGGACTACGTCGTGGGAG
CCAGAACGTTCCGCAGAGAAAAGAGGGCCGAGCGTCTCACCTCCAGGGTGAAGGCACTGTTCA
GCGTGCTCAACTACGAGCGGGCGCGGCGCCCCGGCCTCCTGGGCGCCTCTGTGCTGGGCCTG
GACGATATCCACAGGGCCTGGCGCACCTTCGTGCTGCGTGTGCGGGCCCAGGACCCGCCGCCT
GAGCTGTACTTTGTCAAGGTGGATGTGACGGGCGCGTACGACACCATCCCCCAGGACAGGCTCA
CGGAGGTCATCGCCAGCATCATCAAACCCCAGAACACGTACTGCGTGCGTCGGTATGCCGTGGT
CCAGAAGGCCGCCCATGGGCACGTCCGCAAGGCCTTCAAGAGCCACGTCTCTACCTTGACAGAC
CTCCAGCCGTACATGCGACAGTTCGTGGCTCACCTGCAGGAGACCAGCCCGCTGAGGGATGCC
GTCGTCATCGAGCAGAGCTCCTCCCTGAATGAGGCCAGCAGTGGCCTCTTCGACGTCTTCCTAC
GCTTCATGTGCCACCACGCCGTGCGCATCAGGGGCAAGTCCTACGTCCAGTGCCAGGGGATCC
CGCAGGGCTCCATCCTCTCCACGCTGCTCTGCAGCCTGTGCTACGGCGACATGGAGAACAAGCT
GTTTGCGGGGATTCGGCGGGACGGGCTGCTCCTGCGTTTGGTGGATGATTTCTTGTTGGTGAGA
CCTCACCTCACCCACGCGAAAACCTTCCTCAGGACCCTGGTCCGAGGTGTCCCTGAGTATGGCT
GCGTGGTGAACTTGCGGAAGACAGTGGTGAACTTCCCTGTAGAAGACGAGGCCCTGGGTGGCA
CGGCTTTTGTTCAGATGCCGGCCCACGGCCTATTCCCCTGGTGCGGCCTGCTGCTGGATACCCG
GACCCTGGAGGTGCAGAGCGACTACTCCAGCTATGCCCGGACCTCCATCAGAGCCAGTCTCACC
TTCAACCGCGGCTTCAAGGCTGGGAGGAACATGCGTCGCAAACTCTTTGGGGTCTTGCGGCTGA
AGTGTCACAGCCTGTTTCTGGATTTGCAGGTGAACAGCCTCCAGACGGTGTGCACCAACATCTAC
AAGATCCTCCTGCTGCAGGCGTACAGGTTTCACGCATGTGTGCTGCAGCTCCCATTTCATCAGCA
AGTTTGGAAGAACCCCACATTTTTCCTGCGCGTCATCTCTGACACGGCCTCCCTCTGCTACTCCA
TCCTGAAAGCCAAGAACGCAGGGATGTCGCTGGGGGCCAAGGGCGCCGCCGGCCCTCTGCCCT
CCGAGGCCGTGCAGTGGCTGTGCCACCAAGCATTCCTGCTCAAGCTGACTCGACACCGTGTCAC
CTACGTGCCACTCCTGGGGTCACTCAGGACAGCCCAGACGCAGCTGAGTCGGAAGCTCCCGGG
GACGACGCTGACTGCCCTGGAGGCCGCAGCCAACCCGGCACTGCCCTCAGACTTCAAGACCAT
CCTGGACTGAGTCGAAACTCGCGGCCGCCATATGCATCCTAGGCCTATTAATATTCCGGAGTATA
CGTAGCCGGCTAACGTTAACTTGTTTATTGCAGCTTATAATGGTTACAAATAAAGCAATAGCATCA
CAAATTTCACAAATAAAGCATTTTTTTCACTGCATTCTAGTTGTGGTTTGTCCAAACTCATCAATGT
ATCTTAACGCGGATCTGGGCGTGGTTAAGGGTGGGAAAGAATATATAAGGTGGGGGTCTTATGTA
GTTTTGTATCTGTTTTGCAGCAGCCGCCGCCGCCATGAGCACCAACTCGTTTGATGGAAGCATTG
```

-continued

```
TGAGCTCATATTTGACAACGCGCATGCCCCATGGGCCGGGGTGCGTCAGAATGTGATGGGCTC
CAGCATTGATGGTCGCCCCGTCCTGCCCGCAAACTCTACTACCTTGACCTACGAGACCGTGTCT
GGAACGCCGTTGGAGACTGCAGCCTCCGCCGCCGCTTCAGCCGCTGCAGCCACCGCCCGCGG
GATTGTGACTGACTTTGCTTTCCTGAGCCCGCTTGCAAGCAGTGCAGCTTCCCGTTCATCCGCCC
GCGATGACAAGTTGACGGCTCTTTTGGCACAATTGGATTCTTTGACCCGGGAACTTAATGTCGTT
TCTCAGCAGCTGTTGGATCTGCGCCAGCAGGTTTCTGCCCTGAAGGCTTCCTCCCCTCCCAATG
CGGTTTAAAACATAAATAAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGGTCGTTGAGGGTCCT
GTGTATTTTTTCCAGGACGTGGTAAAGGTGACTCTGGATGTTCAGATACATGGGCATAAGCCCGT
CTCTGGGGTGGAGGTAGCACCACTGCAGAGCTTCATGCTGCGGGGTGGTGTTGTAGATGATCCA
GTCGTAGCAGGAGCGCTGGGCGTGGTGCCTAAAAATGTCTTTCAGTAGCAAGCTGATTGCCAGG
GGCAGGCCCTTGGTGTAAGTGTTTACAAAGCGGTTAAGCTGGGATGGGTGCATACGTGGGGATA
TGAGATGCATCTTGGACTGTATTTTTAGGTTGGCTATGTTCCCAGCCATATCCCTCCGGGGATTCA
TGTTGTGCAGAACCACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCCATGCATTCGTCCAT
AATGATGGCAATGGGCCCACGGGCGGCGGCCTGGGCGAAGATATTTCTGGGATCACTAACGTCA
TAGTTGTGTTCCAGGATGAGATCGTCATAGGCCATTTTTACAAAGCGCGGGCGGAGGGTGCCAG
ACTGCGGTATAATGGTTCCATCCGGCCCAGGGGCGTAGTTACCCTCACAGATTTGCATTTCCCAC
GCTTTGAGTTCAGATGGGGGGATCATGTCTACCTGCGGGGCGATGAAGAAAACGGTTTCCGGGG
TAGGGGAGATCAGCTGGGAAGAAAGCAGGTTCCTGAGCAGCTGCGACTTACCGCAGCCGGTGG
GCCCGTAAATCACACCTATTACCGGGTGCAACTGGTAGTTAAGAGAGCTGCAGCTGCCGTCATC
CCTGAGCAGGGGGGCCACTTCGTTAAGCATGTCCCTGACTCGCATGTTTTCCCTGACCAAATCC
GCCAGAAGGCGCTCGCCGCCCAGCGATAGCAGTTCTTGCAAGGAAGCAAAGTTTTTCAACGGTT
TGAGACCGTCCGCCGTAGGCATGCTTTTGAGCGTTTGACCAAGCAGTTCCAGGCGGTCCCACAG
CTCGGTCACCTGCTCTACGGCATCTCGATCCAGCATATCTCCTCGTTTCGCGGGTTGGGCGGC
TTTCGCTGTACGGCAGTAGTCGGTGCTCGTCCAGACGGGCCAGGGTCATGTCTTTCCACGGGCG
CAGGGTCCTCGTCAGCGTAGTCTGGGTCACGGTGAAGGGGTGCGCTCCGGGCTGCGCGCTGGC
CAGGGTGCGCTTGAGGCTGGTCCTGCTGGTGCTGAAGCGCTGCCGGTCTTCGCCCTGCGCGTC
GGCCAGGTAGCATTTGACCATGGTGTCATAGTCCAGCCCCTCCGCGCGTGGCCCTTGGCGCG
CAGCTTGCCCTTGGAGGAGGCGCCGCACGAGGGGCAGTGCAGACTTTTGAGGGCGTAGAGCTT
GGGCGCGAGAAATACCGATTCCGGGGAGTAGGCATCCGCGCCGCAGGCCCCGCAGACGGTCTC
GCATTCCACGAGCCAGGTGAGCTCTGGCCGTTCGGGGTCAAAAACCAGGTTTCCCCCATGCTTT
TTGATGCGTTTCTTACCTCTGGTTTCCATGAGCCGGTGTCCACGCTCGGTGACGAAAAGGCTGTC
CGTGTCGCCGTATACAGACTTGAGAGGCCTGTCCTCGAGCGGTGTTCCGCGGTCCTCCTCGTAT
AGAAACTCGGACCACTCTGAGACAAAGGCTCGCGTCCAGGCCAGCACGAAGGAGGCTAAGTGG
GAGGGGTAGCGGTCGTTGTCCACTAGGGGTCCACTCGCTCCAGGGTGTGAAGACACATGTCG
CCCTCTTCGGCATCAAGGAAGGTGATTGGTTTGTAGGTGTAGGCCACGTGACCGGGTGTTCCTG
AAGGGGGGCTATAAAAGGGGGTGGGGGCGCGTTCGTCCTCACTCTCTTCCGCATCGCTGTCTGC
GAGGGCCAGCTGTTGGGGTGAGTACTCCCTCTGAAAAGCGGGCATGACTTCTGCGCTAAGATTG
TCAGTTTCCAAAAACGAGGAGGATTTGATATTCACCTGGCCCGCGGTGATGCCTTTGAGGGTGG
CCGCATCCATCTGGTCAGAAAAGACAATCTTTTTGTTGTCAAGCTTGGTGGCAAACGACCCGTAG
```

-continued
```
AGGGCGTTGGACAGCAACTTGGCGATGGAGCGCAGGGTTTGGTTTTTGTCGCGATCGGCGCG
TCCTTGGCCGCGATGTTTAGCTGCACGTATTCGCGCGCAACGCACCGCCATTCGGGAAAGACGG
TGGTGCGCTCGTCGGGCACCAGGTGCACGCGCCAACCGCGGTTGTGCAGGGTGACAAGGTCAA
CGCTGGTGGCTACCTCTCCGCGTAGGCGCTCGTTGGTCCAGCAGAGGCGGCCGCCCTTGCGCG
AGCAGAATGGCGGTAGGGGGTCTAGCTGCGTCTCGTCCGGGGGTCTGCGTCCACGGTAAAGA
CCCCGGGCAGCAGGCGCGCGTCGAAGTAGTCTATCTTGCATCCTTGCAAGTCTAGCGCCTGCTG
CCATGCGCGGGCGGCAAGCGCGCTCGTATGGGTTGAGTGGGGGACCCCATGGCATGGGT
GGGTGAGCGCGGAGGCGTACATGCCGCAAATGTCGTAAACGTAGAGGGGCTCTCTGAGTATTCC
AAGATATGTAGGGTAGCATCTTCCACCGCGGATGCTGGCGCGCACGTAATCGTATAGTTCGTGC
GAGGGAGCGAGGAGGTCGGGACCGAGGTTGCTACGGGCGGGCTGCTCTGCTCGGAAGACTATC
TGCCTGAAGATGGCATGTGAGTTGGATGATATGGTTGGACGCTGGAAGACGTTGAAGCTGGCGT
CTGTGAGACCTACCGCGTCACGCACGAAGGAGGCGTAGGAGTCGCGCAGCTTGTTGACCAGCT
CGGCGGTGACCTGCACGTCTAGGGCGCAGTAGTCCAGGGTTTCCTTGATGATGTCATACTTATC
CTGTCCCTTTTTTTTCCACAGCTCGCGGTTGAGGACAAACTCTTCGCGGTCTTTCCAGTACTCTTG
GATCGGAAACCCGTCGGCCTCCGAACGGTAAGAGCCTAGCATGTAGAACTGGTTGACGGCCTGG
TAGGCGCAGCATCCCTTTTCTACGGGTAGCGCGTATGCCTGCGCGGCCTTCCGGAGCGAGGTGT
GGGTGAGCGCAAAGGTGTCCCTGACCATGACTTTGAGGTACTGGTATTTGAAGTCAGTGTCGTC
GCATCCGCCCTGCTCCCAGAGCAAAAAGTCCGTGCGCTTTTTGGAACGCGGATTTGGCAGGGCG
AAGGTGACATCGTTGAAGAGTATCTTTCCCGCGCGAGGCATAAAGTTGCGTGTGATGCGGAAGG
GTCCCGGCACCTCGGAACGGTTGTTAATTACCTGGGCGGCGAGCACGATCTCGTCAAAGCCGTT
GATGTTGTGGCCCACAATGTAAAGTTCCAAGAAGCGCGGGATGCCGTTGATGGAAGGCAATTTTT
TAAGTTCCTCGTAGGTGAGCTCTTCAGGGGAGCTGAGCCCGTGCTCTGAAAGGGCCCAGTCTGC
AAGATGAGGGTTGGAAGCGACGAATGAGCTCCACAGGTCACGGGCCATTAGCATTTGCAGGTGG
TCGCGAAAGGTCCTAAACTGGCGACCTATGGCCATTTTTTCTGGGGTGATGCAGTAGAAGGTAAG
CGGGTCTTGTTCCGAGGGGTCCCATCCAAGGTTCGCGGCTAGGTCTCGCGCGGCAGTCACTAGA
GGCTCATCTCCGCCGAACTTCATGACCAGCATGAAGGGCACGAGCTGCTTCCCAAAGGCCCCCA
TCCAAGTATAGGTCTCTACATCGTAGGTGACAAAGAGACGCTCGGTGCGAGGATGCGAGCCGAT
CGGGAAGAACTGGATCTCCCGCCACCAATTGGAGGAGTGGCTATTGATGTGGTGAAAGTAGAAG
TCGCTGCGAGGGGCCGAACACTCGTGCTGGCTTTTGTAAAAACGTGCGCAGTACTGGCAGGGGT
GCACGGGCTGTACATCCTGCACGAGGTTGACCTGACGACCGCGCACAAGGAAGCAGAGTGGGA
ATTTGAGCCCCTCGCCTGGCGGGTTTGGCTGGTGGTCTTCTACTTCGGCTGCTTGTCCTTGACC
GTCTGGCTGCTCGAGGGGAGTTACGGTGGATCGGACCACCACGCCGCGCGAGCCCAAAGTCCA
GATGTCCGCGCGCGGCGGTCGGAGCTTGATGACAACATCGCGCAGATGGGAGCTGTCCATGGT
CTGGAGCTCCCGCGGCGTCAGGTCAGGCGGGAGCTCCTGCAGGTTTACCTCGCATAGACGGGT
CAGGGCGCGGGCTAGATCCAGGTGATACCTAATTTCCAGGGGCTGGTTGGTGGCGGCGTCGAT
GGCTTGCAAGAGGCCGCATCCCCGCGGCGCGACTACGGTACCGCGCGGCGGGCGTGGGCCG
CGGGGGTGTCCTTGGATGATGCATCTAAAAGCGGTGACGCGGGCGAGCCCCCGGAGGTAGGGG
GGGCTCCGGACCCGCCGGGAGAGGGGGCAGGGGCACGTCGGCGCCGCGCGCGGGCAGGAGC
TGGTGCTGCGCGCGTAGGTTGCTGGCGAACGCGACGACGCGGCGGTTGATCTCCTGAATCTGG
CGCCTCTGCGTGAAGACGACGGGCCCGGTGAGCTTGAGCCTGAAAGAGAGTTCGACAGAATCAA
TTTCGGTGTCGTTGACGGCGGCCTGGCGCAAAATCTCCTGCACGTCTCCTGAGTTGTCTTGATAG
```

-continued
```
GCGATCTCGGCCATGAACTGCTCGATCTCTTCCTCCTGGAGATCTCCGCGTCCGGCTCGCTCCA
CGGTGGCGGCGAGGTCGTTGGAAATGCGGGCCATGAGCTGCGAGAAGGCGTTGAGGCCTCCCT
CGTTCCAGACGCGGCTGTAGACCACGCCCCCTTCGGCATCGCGGGCGCGCATGACCACCTGCG
CGAGATTGAGCTCCACGTGCCGGGCGAAGACGGCGTAGTTTCGCAGGCGCTGAAAGAGGTAGT
TGAGGGTGGTGGCGGTGTGTTCTGCCACGAAGAAGTACATAACCCAGCGTCGCAACGTGGATTC
GTTGATATCCCCCAAGGCCTCAAGGCGCTCCATGGCCTCGTAGAAGTCCACGGCGAAGTTGAAA
AACTGGGAGTTGCGCGCCGACACGGTTAACTCCTCCTCCAGAAGACGGATGAGCTCGGCGACA
GTGTCGCGCACCTCGCGCTCAAAGGCTACAGGGGCCTCTTCTTCTTCTTCAATCTCCTCTTCCAT
AAGGGCCTCGCCTTCTTCTTCTTCTGGCGGCGGTGGGGGAGGGGGACAGGGCGGCGAGGAC
GGCGCACCGGGAGGCGGTCGACAAAGCGCTCGATCATCTCCCCGCGGCGACGGCGCATGGTCT
CGGTGACGGCGCGGCCGTTCTCGCGGGGCGCAGTTGGAAGACGCCGCCCGTCATGTCCCGG
TTATGGGTTGGCGGGGGGCTGCCATGCGGCAGGGATACGGCGCTAACGATGCATCTCAACAATT
GTTGTGTAGGTACTCCGCCGCCGAGGGACCTGAGCGAGTCCGCATCGACCGGATCGGAAAACC
TCTCGAGAAAGGCGTCTAACCAGTCACAGTCGCAAGGTAGGCTGAGCACCGTGGCGGGCGGCA
GCGGGCGGCGGTCGGGGTTGTTTCTGGCGGAGGTGCTGCTGATGATGTAATTAAAGTAGGCGG
TCTTGAGACGGCGGATGGTCGACAGAAGCACCATGTCCTTGGGTCCGGCCTGCTGAATGCGCAG
GCGGTCGGCCATGCCCCAGGCTTCGTTTTGACATCGGCGCAGGTCTTTGTAGTAGTCTTGCATG
AGCCTTTCTACCGGCACTTCTTCTTCTCCTTCCTCTTGTCCTGCATCTCTTGCATCTATCGCTGCG
GCGGCGGCGGAGTTTGGCCGTAGGTGGCGCCCTCTTCCTCCCATGCGTGTGACCCCGAAGCCC
CTCATCGGCTGAAGCAGGGCTAGGTCGGCGACAACGCGCTCGGCTAATATGGCCTGCTGCACCT
GCGTGAGGGTAGACTGGAAGTCATCCATGTCCACAAAGCGGTGGTATGCGCCCGTGTTGATGGT
GTAAGTGCAGTTGGCCATAACGGACCAGTTAACGGTCTGGTGACCCGGCTGCGAGAGCTCGGTG
TACCTGAGACGCGAGTAAGCCCTCGAGTCAAATACGTAGTCGTTGCAAGTCCGCACCAGGTACT
GGTATCCCACCAAAAAGTGCGGCGGCGGCTGGCGGTAGAGGGGCCAGCGTAGGGTGGCCGGG
GCTCCGGGGGCGAGATCTTCCAACATAAGGCGATGATATCCGTAGATGTACCTGGACATCCAGG
TGATGCCGGCGGCGGTGGTGGAGGCGCGCGGAAAGTCGCGGACGCGGTTCCAGATGTTGCGC
AGCGGCAAAAAGTGCTCCATGGTCGGGACGCTCTGGCCGGTCAGGCGCGCGCAATCGTTGACG
CTCTACCGTGCAAAAGGAGAGCCTGTAAGCGGGCACTCTTCCGTGGTCTGGTGGATAAATTCGC
AAGGGTATCATGGCGGACGACCGGGGTTCGAGCCCCGTATCCGGCCGTCCGCCGTGATCCATG
CGGTTACCGCCCGCGTGTCGAACCCAGGTGTGCGACGTCAGACAACGGGGAGTGCTCCTTTT
GGCTTCCTTCCAGGCGCGGCGGCTGCTGCGCTAGCTTTTTTGGCCACTGGCCGCGCGCAGCGT
AAGCGGTTAGGCTGGAAAGCGAAAGCATTAAGTGGCTCGCTCCCTGTAGCCGGAGGGTTATTTT
CCAAGGGTTGAGTCGCGGGACCCCCGGTTCGAGTCTCGGACCGGCCGGACTGCGGCGAACGG
GGGTTTGCCTCCCCGTCATGCAAGACCCCGCTTGCAAATTCCTCCGGAAACAGGGACGAGCCCC
TTTTTTGCTTTTCCCAGATGCATCCGGTGCTGCGGCAGATGCGCCCCCCTCCTCAGCAGCGGCA
AGAGCAAGAGCAGCGGCAGACATGCAGGGCACCCTCCCCTCCTCCTACCGCGTCAGGAGGGGC
GACATCCGCGGTTGACGCGGCAGCAGATGGTGATTACGAACCCCCGCGGCGCCGGGCCCGGC
ACTACCTGGACTTGGAGGAGGGCGAGGGCCTGGCGCGGCTAGGAGCGCCCTCTCCTGAGCGGT
ACCCAAGGGTGCAGCTGAAGCGTGATACGCGTGAGGCGTACGTGCCGCGGCAGAACCTGTTTC
GCGACCGCGAGGGAGAGGAGCCCGAGGAGATGCGGGATCGAAAGTTCCACGCAGGGCGCGAG
CTGCGGCATGGCCTGAATCGCGAGCGGTTGCTGCGCGAGGAGGACTTTGAGCCCGACGCGCGA
```

-continued

```
ACCGGGATTAGTCCCGCGCGCACACGTGGCGGCCGCCGACCTGGTAACCGCATACGAGCAG

ACGGTGAACCAGGAGATTAACTTTCAAAAAAGCTTTAACAACCACGTGCGTACGCTTGTGGCGCG

CGAGGAGGTGGCTATAGGACTGATGCATCTGTGGGACTTTGTAAGCGCGCTGGAGCAAAACCCA

AATAGGAAGCCGCTCATGGCGCAGCTGTTCCTTATAGTGCAGCACAGCAGGGACAACGAGGCAT

TCAGGGATGCGCTGCTAAACATAGTAGAGCCCGAGGGCCGCTGGCTGCTCGATTTGATAAACAT

CCTGCAGAGCATAGTGGTGCAGGAGCGCAGCTTGAGCCTGGCTGACAAGGTGGCCGCCATCAA

CTATTCCATGCTTAGCCTGGGCAAGTTTTACGCCCGCAAGATATACCATACCCCTTACGTTCCCAT

AGACAAGGAGGTAAAGATCGAGGGGTTCTACATGCGCATGGCGCTGAAGGTGCTTACCTTGAGC

GACGACCTGGGCGTTTATCGCAACGAGCGCATCCACAAGGCCGTGAGCGTGAGCCGGCGGCGC

GAGCTCAGCGACCGCGAGCTGATGCACAGCCTGCAAAGGGCCCTGGCTGGCACGGGCAGCGG

CGATAGAGAGGCCGAGTCCTACTTTGACGCGGGCGCTGACCTGCGCTGGGCCCCAAGCCGAGG

CGCCCTGGAGGCAGCTGGGGCCGGACCTGGGCTGGCGGTGGCACCCGCGCGCGCTGGCAACG

TCGGCGGCGTGGAGGAATATGACGAGGACGATGAGTACGAGCCAGAGGACGGCGAGTACTAAG

CGGTGATGTTTCTGATCAGATGATGCAAGACGCAACGGACCCGGCGGTGCGGGCGGCGCTGCA

GAGCCAGCCGTCCGGCCTTAACTCCACGGACGACTGGCGCCAGGTCATGGACCGCATCATGTC

GCTGACTGCGCGCAATCCTGACGCGTTCCGGCAGCAGCCGCAGGCCAACCGGCTCTCCGCAAT

TCTGGAAGCGGTGGTCCCGGCGCGCGCAAACCCCACGCACGAGAAGGTGCTGGCGATCGTAAA

CGCGCTGGCCGAAAACAGGGCCATCCGGCCCGACGAGGCCGGCCTGGTCTACGACGCGCTGC

TTCAGGGCGTGGCTCGTTACAACAGCGGCAAGGTGCAGACCAACCTGGACCGGCTGGTGGGGG

ATGTGCGCGAGGCCGTGGCGCAGCGTGAGCGCGCGCAGCAGCAGGGCAACCTGGGCTCCATG

GTTGCACTAAACGCCTTCCTGAGTACACAGCCCGCCAACGTGCCGCGGGGACAGGAGGACTACA

CCAACTTTGTGAGCGCACTGCGGCTAATGGTGACTGAGACACCGCAAAGTGAGGTGTACCAGTC

TGGGCCAGACTATTTTTTCCAGACCAGTAGACAAGGCCTGCAGACCGTAAACCTGAGCCAGGCTT

TCAAAAACTTGCAGGGGCTGTGGGGGGTGCGGGCTCCCACAGGCGACCGCGCGACCGTGTCTA

GCTTGCTGACGCCCAACTCGCGCCTGTTGCTGCTGCTAATAGCGCCCTTCACGGACAGTGGCAG

CGTGTCCCGGGACACATACCTAGGTCACTTGCTGACACTGTACCGCGAGGCCATAGGTCAGGCG

CATGTGGACGAGCATACTTTCCAGGAGATTACAAGTGTCAGCCGCGCGCTGGGGCAGGAGGACA

CGGGCAGCCTGGAGGCAACCCTAAACTACCTGCTGACCAACCGGCGGCAGAAGATCCCCTCGTT

GCACAGTTTAAACAGCGAGGAGGAGCGCATTTTGCGCTACGTGCAGCAGAGCGTGAGCCTTAAC

CTGATGCGCGACGGGGTAACGCCCAGCGTGGCGCTGGACATGACCGCGCGCAACATGGAACCG

GGCATGTATGCCTCAAACCGGCCGTTTATCAACCGCCTAATGGACTACTTGCATCGCGCGGCCG

CCGTGAACCCCGAGTATTTCACCAATGCCATCTTGAACCCGCACTGGCTACCGCCCCCTGGTTTC

TACACCGGGGGATTCGAGGTGCCCGAGGGTAACGATGGATTCCTCTGGGACGACATAGACGACA

GCGTGTTTTCCCCGCAACCGCAGACCCTGCTAGAGTTGCAACAGCGCGAGCAGGCAGAGGCGG

CGCTGCGAAAGGAAAGCTTCCGCAGGCCAAGCAGCTTGTCCGATCTAGGCGCTGCGGCCCCGC

GGTCAGATGCTAGTAGCCCATTTCCAAGCTTGATAGGGTCTCTTACCAGCACTCGCACCACCCGC

CCGCGCCTGCTGGGCGAGGAGGAGTACCTAAACAACTCGCTGCTGCAGCCGCAGCGCGAAAAA

AACCTGCCTCCGGCATTTCCCAACAACGGGATAGAGAGCCTAGTGGACAAGATGAGTAGATGGA

AGACGTACGCGCAGGAGCACAGGGACGTGCCAGGCCCGCGCCCGCCCACCCGTCGTCAAAGG

CACGACCGTCAGCGGGGTCTGGTGTGGGAGGACGATGACTCGGCAGACGACAGCAGCGTCCTG

GATTTGGGAGGGAGTGGCAACCCGTTTGCGCACCTTCGCCCCAGGCTGGGGAGAATGTTTTAAA
```

-continued

```
AAAAAAAAAGCATGATGCAAAATAAAAAACTCACCAAGGCCATGGCACCGAGCGTTGGTTTTCTT
GTATTCCCCTTAGTATGCGGCGCGCGGCGATGTATGAGGAAGGTCCTCCTCCCTCCTACGAGAG
TGTGGTGAGCGCGGCGCCAGTGGCGGCGGCGCTGGGTTCTCCCTTCGATGCTCCCCTGGACCC
GCCGTTTGTGCCTCCGCGGTACCTGCGGCCTACCGGGGGAGAAACAGCATCCGTTACTCTGA
GTTGGCACCCCTATTCGACACCACCCGTGTGTACCTGGTGGACAACAAGTCAACGGATGTGGCA
TCGCTGAACTACCAGAACGACCACAGGAACTTTCTGACCAGGGTCATTGAAAACAATGACTACAG
CCCGGGGGAGGCAAGCACACAGACCATCAATCTTGACGACCGGTCGCACTGGGGCGGCGACCT
GAAAACCATCCTGCATACCAACATGCCAAATGTGAACGAGTTCATGTTTACCAATAAGTTTAAGGC
GCGGGTGATGGTGTCGCGCTTGCCTACTAAGGACAATCAGGTGGAGCTGAAATACGAGTGGGTG
GAGTTGAGGCTGCCCGAGGGCAACTACTCCGAGACCATGACCATAGACCTTATGAACAACGCGA
TCGTGGAGCACTACTTGAAAGTGGGCAGACAGAACGGGGTTCTGGAAAGCGACATCGGGGTAAA
GTTTGACACCCGCAACTTCAGACTGGGGTTTGACCCCGTCACTGGTCTTGTCATGCCTGGGGTAT
ATACAAACGAAGCCTTCCATCCAGACATCATTTTGCTGCCAGGATGCGGGGTGGACTTCACCCAC
AGCCGCCTGAGGAACTTGTTGGGCATCCGCAAGGGGCAACCCTTCCAGGAGGGCTTTAGGATCA
CCTACGATGATCTGGAGGGTGGTAACATTCCCGCACTGTTGGATGTGGACGCCTACCAGGCGAG
CTTGAAAGATGACACCGAACAGGGCGGGGGTGGCGCAGGCGGCAGCAACAGCAGTGGCAGCG
GCGCGGAAGAGAACTCCAACGCGGCAGCCGCGGCAATGCAGCCGGTGGAGGACATGAACGATC
ATGCCATTCGCGGCGAGACCTTTGCCAGAGGGGCTGAGGAGAAGCGCGCTGAGGCCGAAGGAG
CGGCCGAAGCTGCCGCCCCGCTGCGCAACCCGAGGTCGAGAAGCCTCAGAAGAAACCGGTGA
TCAAACCCCTGACAGAGGACAGCAAGAAACGCAGTTACAACCTAATAAGCAATGACAGCACCTTC
ACCCAGTACCGCAGCTGGTACCTTGCATACAACTACGGCGACCCTCAGACCGGAATCCGCTCAT
GGACCCTGCTTTGCACTCCTGACGTAACCTGCGGCTCGGAGCAGGTCTACTGGTCGTTGCCAGA
CATGATGCAAGACCCCGTGACCTTCCGCTCCACGCGCCAGATCAGCAACTTTCCGGTGGTGGGC
GCCGAGCTGTTGCCCGTGCACTCCAAGAGCTTCTACAACGACCAGGCCGTCTACTCCCAACTCA
TCCGCCAGTTTACCTCTCTGACCCACGTGTTCAATCGCTTTCCCGAGAACCAGATTTTGGCGCGC
CCGCCAGCCCCCACCATCACCACCGTCAGTGAAAACGTTCCTGCTCTCACAGATCACGGGACGC
TACCGCTGCGCAACAGCATCGGAGGAGTCCAGCGAGTGACCATTACTGACGCCAGACGCCGCA
CCTGCCCCTACGTTTACAAGGCCCTGGGCATAGTCTCGCCGCGCGTCCTATCGAGCCGCACTTT
TTGAGCAAGCATGTCCATCCTTATATCGCCCAGCAATAACACAGGCTGGGGCCTGCGCTTCCCAA
GCAAGATGTTTGGCGGGGCCAAGAAGCGCTCCGACCAACACCCAGTGCGCGTGCGCGGGCACT
ACCGCGCGCCCTGGGGCGCGCACAAACGCGGCCGCACTGGGCGCACCACCGTCGATGACGCC
ATCGACGCGGTGGTGGAGGAGGCGCGCAACTACACGCCCACGCCGCCACCAGTGTCCACAGTG
GACGCGGCCATTCAGACCGTGGTGCGCGGAGCCCGGCGCTATGCTAAAATGAAGAGACGGCGG
AGGCGCGTAGCACGTCGCCACCGCCGCCGACCCGGCACTGCCGCCCAACGCGCGGCGGCGGC
CCTGCTTAACCGCGCACGTCGCACCGGCCGAGGGGCGGCCATGCGGGCCGCTCGAAGGCTGG
CCGCGGGTATTGTCACTGTGCCCCCCAGGTCCAGGCGACGAGCGGCCGCCGCAGCAGCCGCG
GCCATTAGTGCTATGACTCAGGGTCGCAGGGGCAACGTGTATTGGGTGCGCGACTCGGTTAGCG
GCCTGCGCGTGCCCGTGCGCACCCGCCCGCCGCGCAACTAGATTGCAAGAAAAAACTACTTAGA
CTCGTACTGTTGTATGTATCCAGCGGCGGCGGCGCGCAACGAAGCTATGTCCAAGCGCAAAATC
AAAGAAGAGATGCTCCAGGTCATCGCGCCGGAGATCTATGGCCCCCCGAAGAAGGAAGAGCAG
GATTACAAGCCCCGAAAGCTAAAGCGGGTCAAAAAGAAAAAGAAAGATGATGATGATGAACTTGA
```

-continued

```
CGAGGAGGTGGAACTGCTGCAGGCTACCGCGCCCAGGCGAGGGGTAGAGTGGAAAGGTCGAGG
CGTAAAACGTGTTTTGCGACCCGGCACCACCGTAGTCTTTACGCCCGGTGAGCGCTCCACCCGC
ACCTACAAGCGCGTGTATGATGAGGTGTACGGCGACGAGGACCTGCTTGAGCAGGCCAACGAG
CGCCTCGGGGAGTTTGCCTACGGAAAGCGGCATAAGGACATGCTGGCGTTGCCGCTGGACGAG
GGCAACCCAACACCTAGGCTAAAGCCCGTAACACTGCAGGAGGTGCTGCCCGCGCTTGCACCGT
CCGAAGAAAAGCGCGGCCTAAAGCGCGAGTCTGGTGACTTGGCACCCACCGTGCAGCTGATGG
TACCCAAGCGCCAGCGACTGGAAGATGTCTTGGAAAAAATGACCGTGGAACCTGGGCTGGAGCC
CGAGGTCCGCGTGCGGCCAATCAAGCAGGTGGCGCCGGGACTGGGCGTGCAGACCGTGGACG
TTCAGATACCCACTACCAGTAGGACCAGTATTGCCACCGCCACAGAGGGCATGGAGACACAAAC
GTCCCCGGTTGCCTCAGCGGTGGCGGATGCCGCGGTGCAGGCGGTCGCTGCGGCCGCGTCCA
AGACCTCTACGGAGGTGCAAACGGACCCGTGGATGTTTCGCGTTTCAGCCCCCCGGCGCCCGC
GCGGTTCGAGGAAGTACGGCGCCGCCAGCGCGCTACTGCCCGAATATGCCCTACATCCTTCCAT
TGCGCCTACCCGCGGCTATCGTGGCTACACCTACCGCCCCAGAAGAGGAGGAACTACCCGACGC
CGAACCACCACTGGAACCCGCCGCCGCCGTCGCCGTCGCCAGCCCGTGCTGGCCCCGATTTCC
GTGCGCAGGGTGGCTCGCGAAGGAGGCAGGACCCTGGTGCTGCCAACAGCGCGCTACCACCC
CAGCATCGTTTAAAAGCCGGTCTTTGTGGTTCTTGCAGATATGGCCCTCACCTGCCGCCTCCGTT
TCCCGGTGCCGGGATTCCGAGGAAGAATGCACCGTAGGAGGGGCATGGCCGGCCACGGCCTGA
CGGGCGGCATGCGTCGTGCGCACCACCGGCGGCGGCGCGCGTCGCACCGTCGCATGCGCGGC
GGTATCCTGCCCCTCCTTATTCCACTGATCGCCGCGGCGATTGGCGCCGTGCCCGGAATTGCAT
CCGTGGCCTTGCAGGCGCAGAGACACTGATTAAAAACAAGTTGCATGTGGAAAAATCAAATAAA
AAGTCTGGACTCTCACGCTCGCTTGGTCCTGTAACTATTTTGTAGAATGGAAGACATCAACTTTGC
GTCTCTGGCCCCGCGACACGGCTCGCGCCCGTTCATGGGAAACTGGCAAGATATCGGCACCAG
CAATATGAGCGGTGGCGCCTTCAGCTGGGGCTCGCTGTGGAGCGGCATTAAAAATTTCGGTTCC
ACCGTTAAGAACTATGGCAGCAAGGCCTGGAACAGCAGCACAGGCCAGATGCTGAGGGATAAGT
TGAAAGAGCAAAATTTCCAACAAAAGGTGGTAGATGGCCTGGCCTCTGGCATTAGCGGGGTGGT
GGACCTGGCCAACCAGGCAGTGCAAAATAAGATTAACAGTAAGCTTGATCCCCGCCCTCCCGTA
GAGGAGCCTCCACCGGCCGTGGAGACAGTGTCTCCAGAGGGGCGTGGCGAAAAGCGTCCGCG
CCCCGACAGGGAAGAAACTCTGGTGACGCAAATAGACGAGCCTCCCTCGTACGAGGAGGCACTA
AAGCAAGGCCTGCCCACCACCCGTCCCATCGCGCCCATGGCTACCGGAGTGCTGGGCCAGCAC
ACACCCGTAACGCTGGACCTGCCTCCGCCCGCCGAGACCCAGGAGAAACCTGTGCTGCCAGGC
CCGACCGCCGTTGTTGTAACCCGTCCTAGCCGCGCGTCCCTGCCGCGCGCCGCCAGCGGTCCG
CGATCGTTGCGGCCCGTAGCCAGTGGCAACTGGCAAAGCACACTGAACAGCATCGTGGGTCTG
GGGGTGCAATCCCTGAAGCGCCGACGATGCTTCTGAATAGCTAACGTGTCGTATGTGTGTCATGT
ATGCGTCCATGTCGCCGCCAGAGGAGCTGCTGAGCCGCCGCGCGCCCGCTTTCCAAGATGGCT
ACCCCTTCGATGATGCCGCAGTGGTCTTACATGCACATCTCGGGCCAGGACGCCTCGGAGTACC
TGAGCCCCGGGCTGGTGCAGTTTGCCCGCGCCACCGAGACGTACTTCAGCCTGAATAACAAGTT
TAGAAACCCCACGGTGGCGCCTACGCACGACGTGACCACAGACCGGTCCGAGGGTTTGAGGCT
GCGGTTCATCCCTGTGGACCGTGAGGATACTGCGTACTCGTACAAGGCGCGGTTCACCCTAGCT
GTGGGTGATAACCGTGTGCTGGACATGGCTTCCACGTACTTTGACATCCGCGGCGTGCTGGACA
GGGGCCCTACTTTTAAGCCCTACTCTGGCACTGCCTACAACGCCCTGGCTCCCAAGGGTGCCCC
AAATCCTTGCGAATGGGATGAAGCTGCTACTGCTCTTGAAATAAACCTAGAAGAAGAGGAGGATG
```

-continued

```
ACAACGAAGACGAAGTAGACGAGCAAGCTGAGCAGCAAAAAACTCACGTATTTGGGCAGGCGCC
TTATTCTGGTATAAATATTACAAAGGAGGGTATTCAAATAGGTGTCGAAGGTCAAACACCTAAATA
TGCCGATAAAACATTTCAACCTGAACCTCAAATAGGAGAATCTCAGTGGTACGAAACTGAAATTAA
TCATGCAGCTGGGAGAGTCCTTAAAAAGACTACCCCAATGAAACCATGTTAGGGTTCATATGCAA
AACCCACAAATGAAATGGAGGGCAAGGCATTCTTGTAAAGCAACAAAATGGAAAGCTAGAAAGT
CAAGTGGAAATGCAATTTTTCTCAACTACTGAGGCGACCGCAGGCAATGGTGATAACTTGACTCC
TAAAGTGGTATTGTACAGTGAAGATGTAGATATAGAAACCCCAGACACTCATATTTCTTACATGCC
CACTATTAAGGAAGGTAACTGAGGAGAACTAATGGGCCAACAATCTATGCCCAACAGGCCTAATT
ACATTGCTTTTAGGGACAATTTTATTGGTCTAATGTATTACAACAGCACGGGTAATATGGGTGTTC
TGGCGGGCCAAGCATCGCAGTTGAATGCTGTTGTAGATTTGCAAGACAGAAACACAGAGCTTTCA
TACCAGCTTTTGCTTGATTCCATTGGTGATAGAACCAGGTACTTTTCTATGTGGAATCAGGCTGTT
GACAGCTATGATCCAGATGTTAGAATTATTGAAAATCATGGAACTGAAGATGAACTTCCAAATTAC
TGCTTTCCACTGGGAGGTGTGATTAATACAGAGACTCTTACCAAGGTAAAACCTAAAACAGGTCA
GGAAAATGGATGGGAAAAAGATGCTACAGAATTTTCAGATAAAAATGAAATAAGAGTTGGAAATAA
TTTTGCCATGGAAATCAATCTAAATGCCAACCTGTGGAGAAATTTCCTGTACTCCAACATAGCGCT
GTATTTGCCCGACAAGCTAAAGTACAGTCCTTCCAACGTAAAAATTTCTGATAACCCAAACACCTA
CGACTACATGAACAAGCGAGTGGTGGCTCCCGGGTTAGTGGACTGCTACATTAACCTTGGAGCA
CGCTGGTCCCTTGACTATATGGACAACGTCAACCCATTTAACCACCACCGCAATGCTGGCCTGCG
CTACCGCTCAATGTTGCTGGGCAATGGTCGCTATGTGCCCTTCCACATCCAGGTGCCTCAGAAGT
TCTTTGCCATTAAAAACCTCCTTCTCCTGCCGGGCTCATACACCTACGAGTGGAACTTCAGGAAG
GATGTTAACATGGTTCTGCAGAGCTCCCTAGGAAATGACCTAAGGGTTGAGGGAGCCAGGATTAA
GTTTGATAGCATTTGCCTTTACGCCACCTTCTTCCCCATGGCCCACAACACCGCCTCCACGCTTG
AGGCCATGCTTAGAAACGACACCAACGACCAGTCCTTTAACGACTATCTCTCCGCCGCCAACATG
CTCTACCCTATACCCGCCAACGCTACCAACGTGCCCATATCCATCCCCTCCCGCAACTGGGCGG
CTTTCCGCGGCTGGGCCTTGAGGCGCCTTAAGACTAAGGAAACCCCATCACTGGGCTCGGGCTA
CGACCCTTATTACACCTACTCTGGCTCTATACCCTACCTAGATGGAACCTTTTACCTCAACCACAC
CTTTAAGAAGGTGGCCATTACCTTTGACTCTTCTGTCAGCTGGCCTGGCAATGACCGCCTGCTTA
CCCCCAACGAGTTTGAAATTAAGCGCTCAGTTGACGGGGAGGGTTACAACGTTGCCCAGTGTAA
CATGACCAAAGACTGGTTCCTGGTACAAATGCTAGCTAACTACAACATTGGCTACCAGGGCTTCT
ATATCCCAGAGAGCTACAAGGACCGCATGTACTCCTTCTTTAGAAACTTCCAGCCCATGAGCCGT
CAGGTGGTGGATGATACTAAATACAAGGACTACCAACAGGTGGGCATCCTACACCAACACAACAA
CTCTGGATTTGTTGGCTACCTTGCCCCCACCATGCGCGAAGGACAGGCCTACCCTGCTAACTTCC
CCTATCCGCTTATAGGCAAGACCGCAGTTGACAGCATTACCCAGAAAAAGTTTCTTTGCGATCGC
ACCCTTTGGCGCATCCCATTCTCCAGTAACTTTATGTCCATGGGCGCACTCACAGACCTGGGCCA
AAACCTTCTCTACGCCAACTCCGCCCACGCGCTAGACATGACTTTTGAGGTGGATCCCATGGACG
AGCCCACCCTTCTTTATGTTTTGTTTGAAGTCTTTGACGTGGTCCGTGTGCACCGGCCGCACCGC
GGCGTCATCGAAACCGTGTACCTGCGCACGCCCTTCTCGGCCGGCAACGCCACAACATAAAGAA
GCAAGCAACATCAACAACAGCTGCCGCCATGGGCTCCAGTGAGCAGGAACTGAAAGCCATTGTC
AAAGATCTTGGTTGTGGGCCATATTTTTTGGGCACCTATGACAAGCGCTTTCCAGGCTTTGTTTCT
CCACACAAGCTCGCCTGCGCCATAGTCAATACGGCCGGTCGCGAGACTGGGGGCGTACACTGG
ATGGCCTTTGCCTGGAACCCGCACTCAAAAACATGCTACCTCTTTGAGCCCTTTGGCTTTTCTGA
```

-continued

CCAGCGACTCAAGCAGGTTTACCAGTTTGAGTACGAGTCACTCCTGCGCCGTAGCGCCATTGCTT

CTTCCCCCGACCGCTGTATAACGCTGGAAAAGTCCACCCAAAGCGTACAGGGGCCCAACTCGGC

CGCCTGTGGACTATTCTGCTGCATGTTTCTCCAGGCCTTTGCCAACTGGCCCCAAACTCCCATGG

ATCACAACCCCACCATGAACCTTATTACCGGGGTACCCAACTCCATGCTCAACAGTCCCCAGGTA

CAGCCCACCCTGCGTCGCAACCAGGAACAGCTCTACAGCTTCCTGGAGCGCCACTCGCCCTACT

TCCGCAGCCACAGTGCGCAGATTAGGAGCGCCACTTCTTTTTGTCACTTGAAAAACATGTAAAAA

TAATGTACTAGAGACACTTTCAATAAAGGCAAATGCTTTTATTTGTACACTCTCGGGTGATTATTTA

CCCCCACCCTTGCCGTCTGCGCCGTTTAAAAATCAAAGGGGTTCTGCCGCGCATCGCTATGCGC

CACTGGCAGGGACACGTTGCGATACTGGTGTTTAGTGCTCCACTTAAACTCAGGCACAACCATCC

GCGGCAGCTCGGTGAAGTTTTCACTCCACAGGCTGCGCACCATCACCAACGCGTTTAGCAGGTC

GGGCGCCGATATCTTGAAGTCGCAGTTGGGGCCTCCGCCCTGCGCGCGCGAGTTGCGATACAC

AGGGTTGCAGCACTGGAACACTATCAGCGCCGGGTGGTGCACGCTGGCCAGCACGCTCTTGTC

GGAGATCAGATCCGCGTCCAGGTCCTCCGCGTTGCTCAGGGCGAACGGAGTCAACTTTGGTAGC

TGCCTTCCCAAAAAGGGCGCGTGCCCAGGCTTTGAGTTGCACTCGCACCGTAGTGGCATCAAAA

GGTGACCGTGCCCGGTCTGGGCGTTAGGATACAGCGCCTGCATAAAAGCCTTGATCTGCTTAAA

AGCCACCTGAGCCTTTGCGCCTTCAGAGAAGAACATGCCGCAAGACTTGCCGGAAAACTGATTG

GCCGGACAGGCCGCGTCGTGCACGCAGCACCTTGCGTCGGTGTTGGAGATCTGCACCACATTTC

GGCCCCACCGGTTCTTCACGATCTTGGCCTTGCTAGACTGCTCCTTCAGCGCGCGCTGCCCGTT

TTCGCTCGTCACATCCATTTCAATCACGTGCTCCTTATTTATCATAATGCTTCCGTGTAGACACTTA

AGCTCGCCTTCGATCTCAGCGCAGGGGTGCAGCCACAAGGCGCAGCCCGTGGGCTCGTGATGC

TTGTAGGTCACCTCTGCAAACGACTGCAGGTACGCCTGCAGGAATCGCCCCATCATCGTCACAAA

GGTCTTGTTGCTGGTGAAGGTCAGCTGCAACCCGCGGTGCTCCTCGTTCAGCCAGGTCTTGCAT

ACGGCCGCCAGAGCTTCCACTTGGTCAGGCAGTAGTTTGAAGTTCGCCTTTAGATCGTTATCCAC

GTGGTACTTGTCCATCAGCGCGCGCAGCCTCCATGCCCTTCTCCCACGCAGACACGATCGGC

ACACTCAGCGGGTTCATCACCGTAATTTCACTTTCCGCTTCGCTGGGCTCTTCCTCTTCCTCTTGC

GTCCGCATACCACGCGCCACTGGGTCGTCTTCATTCAGCCGCCGCACTGTGCGCTTACCTCCTT

TGCCATGCTTGATTAGCACCGGTGGGTTGCTGAAACCCACCATTTGTAGCGCCACATCTTCTCTT

TCTTCCTCGCTGTCCACGATTACCTCTGGTGATGGCGGGCGCTCGGGCTTGGGAGAAGGGCGCT

TCTTTTTCTTCTTGGGCGCAATGGCCAAATCCGCCGCCGAGGTCGATGGCCGCGGGCTGGGTGT

GCGCGGCACCAGCGCGTCTTGTGATGAGTCTTCCTCGTCCTCGGACTCGATACGCCGCCTCATC

CGCTTTTTTGGGGGCGCCCGGGGAGGCGGCGGCGACGGGGACGGGGACGACACGTCCTCCAT

GGTTGGGGGACGTCGCGCCGCACCGCGTCCGCGCTCGGGGGTGGTTTCGCGCTGCTCCTCTTC

CCGACTGGCCATTTCCTTCTCCTATAGGCAGAAAAAGATCATGGAGTCAGTCGAGAAGAAGGACA

GCCTAACCGCCCCCTCTGAGTTCGCCACCACCGCCTCCACCGATGCCGCCAACGCGCCTACCAC

CTTCCGCGTCGAGGCACCCCCGCTTGAGGAGGAGGAAGTGATTATCGAGCAGGACCCAGGTTTT

GTAAGCGAAGACGACGAGGACCGCTCAGTACCAACAGAGGATAAAAAGCAAGACCAGGACAACG

CAGAGGCAAACGAGGAACAAGTCGGGCGGGGGACGAAAGGCATGGCGACTACCTAGATGTGG

GAGACGACGTGCTGTTGAAGCATCTGCAGCGCCAGTGCGCCATTATCTGCGACGCGTTGCAAGA

GCGCAGCGATGTGCCCCTCGCCATAGCGGATGTGAGCCTTGCCTACGAACGCCACCTATTCTCA

CCGCGCGTACCCCCCAAACGCCAAGAAAACGGCACATGCGAGCCCAACCCGCGCCTCAACTTCT

ACCCCGTATTTGCCGTGCCAGAGGTGCTTGCCACCTATCACATCTTTTTCCAAAACTGCAAGATA

-continued

```
CCCCTATCCTGCCGTGCCAACCGCAGCCGAGCGGACAAGCAGCTGGCCTTGCGGCAGGGCGCT
GTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTG
GTGGAACTCGAGGGTGACAACGCGCGCCTAGCCGTACTAAAACGCAGCATCGAGGTCACCCACT
TTGCCTACCCGGCACTTAACCTACCCCCCAAGGTCATGAGCACAGTCATGAGTGAGCTGATCGT
GCGCCGTGCGCAGCCCCTGGAGAGGGATGCAAATTTGCAAGAACAAACAGAGGAGGGCCTACC
CGCAGTTGGCGACGAGCAGCTAGCGCGCTGGCTTCAAACGCGCGAGCCTGCCGACTTGGAGGA
GCGACGCAAACTAATGATGGCCGCAGTGCTCGTTACCGTGGAGCTTGAGTGCATGCAGCGGTTC
TTTGCTGACCCGGAGATGCAGCGCAAGCTAGAGGAAACATTGCACTACACCTTTCGACAGGGCT
ACGTACGCCAGGCCTGCAAGATCTCCAACGTGGAGCTCTGCAACCTGGTCTCCTACCTTGGAATT
TTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTG
GCAGCAGTGCTTGGAGGAGTGCAACCTCAAGGAGCTGCAGAAACTGCTAAAGCAAAACTTGAAG
GACCTATGGACGGCCTTCAACGAGCGCTCCGTGGCCGCGCACCTGGCGGACATCATTTTCCCCG
AACGCCTGCTTAAAACCCTGCAACAGGGTCTGCCAGACTTCACCAGTCAAAGCATGTTGCAGAAC
TTTAGGAACTTTATCCTAGAGCGCTCAGGAATCTTGCCCGCCACCTGCTGTGCACTTCCTAGCGA
CTTTGTGCCCATTAAGTACCGCGAATGCCCTCCGCCGCTTTGGGGCCACTGCTACCTTCTGCAG
CTAGCCAACTACCTTGCCTACCACTCTGACATAATGGAAGACGTGAGCGGTGACGGTCTACTGGA
GTGTCACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAAGTCCGCGGC
TCCGGGGTTGAAACTCACTCCGGGGCTGTGGACGTCGGCTTACCTTCGCAAATTTGTACCTGAG
GACTACCACGCCCACGAGATTAGGTTCTACGAAGACCAATCCCGCCCGCCAAATGCGGAGCTTA
CCGCCTGCGTCATTACCCAGGGCCACATTCTTGGCCAATTGCAAGCCATCAACAAAGCCCGCCA
AGAGTTTCTGCTACGAAAGGGACGGGGGGTTTACTTGGACCCCCAGTCCGGCGAGGAGCTCAAC
CCAATCCCCCGCCGCCGCAGCCCTATCAGCAGCAGCCGCGGGCCCTTGCTTCCCAGGATGGC
ACCCAAAAAGAAGCTGCAGCTGCCGCCGCCACCCACGGAGGAGGAGGAATACTGGGACAGTCA
GGCAGAGGAGGTTTTGGACGAGGAGGAGGAGGACATGATGGAAGACTGGGAGAGCCTAGACGA
GGAAGCTTCCGAGGTCGAAGAGGTGTCAGACGAAACACCGTCACCCTCGGTCGCATTCCCCTCG
CCGGCGCCCCAGAAATCGGCAACCGGTTCCAGCATGGCTACAACCTCCGCTCCTCAGGCGCCG
CCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGC
GGGCACAAGAACGCCATAGTTGCTTGCTTGCAAGACTGTGGGGGCAACATCTCCTTCGCCCGCC
GCTTTCTTCTCTACCATCACGGCGTGGCCTTCCCCCGTAACATCCTGCATTACTACCGTCATCTCT
ACAGCCCATACTGCACCGGCGGCAGCGGCAGCGGCAGCAACAGCAGCGGCCACACAGAAGCAA
AGGCGACCGGATAGCAAGACTCTGACAAAGCCCAAGAAATCCACAGCGGCGGCAGCAGCAGGA
GGAGGAGCGCTGCGTCTGGCGCCCAACGAACCCGTATCGACCCGCGAGCTTAGAAACAGGATT
TTTCCCACTCTGTATGCTATATTTCAACAGAGCAGGGGCCAAGAACAAGAGCTGAAAATAAAAAAC
AGGTCTCTGCGATCCCTCACCCGCAGCTGCCTGTATCACAAAAGCGAAGATCAGCTTCGGCGCA
CGCTGGAAGACGCGGAGGCTCTCTTCAGTAAATACTGCGCGCTGACTCTTAAGGACTAGTTTCG
CGCCCTTTCTCAAATTTAAGCGCGAAAACTACGTCATCTCCAGCGGCCACACCCGGCGCCAGCA
CCTGTCGTCAGCGCCATTATGAGCAAGGAAATTCCCACGCCCTACATGTGGAGTTACCAGCCACA
```

-continued

```
AATGGGACTTGCGGCTGGAGCTGCCCAAGACTACTCAACCCGAATAAACTACATGAGCGCGGGA
CCCCACATGATATCCCGGGTCAACGGAATCCGCGCCCACCGAAACCGAATTCTCTTGGAACAGG
CGGCTATTACCACCACACCTCGTAATAACCTTAATCCCCGTAGTTGGCCCGCTGCCCTGGTGTAC
CAGGAAAGTCCCGCTCCCACCACTGTGGTACTTCCCAGAGACGCCCAGGCCGAAGTTCAGATGA
CTAACTCAGGGGCGCAGCTTGCGGGCGGCTTTCGTCACAGGGTGCGGTCGCCCGGGCAGGGTA
TAACTCACCTGACAATCAGAGGGCGAGGTATTCAGCTCAACGACGAGTCGGTGAGCTCCTCGCT
TGGTCTCCGTCCGGACGGGACATTTCAGATCGGCGGCGCCGGCCGTCCTTCATTCACGCCTCGT
CAGGCAATCCTAACTCTGCAGACCTCGTCCTCTGAGCCGCGCTCTGGAGGCATTGGAACTCTGC
AATTTATTGAGGAGTTTGTGCCATCGGTCTACTTTAACCCCTTCTCGGGACCTCCCGGCCACTAT
CCGGATCAATTTATTCCTAACTTTGACGCGGTAAAGGACTCGGCGGACGGCTACGACTGAATGTT
AAGTGGAGAGGCAGAGCAACTGCGCCTGAAACACCTGGTCCACTGTCGCCGCCACAAGTGCTTT
GCCCGCGACTCCGGTGAGTTTTGCTACTTTGAATTGCCCGAGGATCATATCGAGGGCCCGGCGC
ACGGCGTCCGGCTTACCGCCCAGGGAGAGCTTGCCCGTAGGCTGATTCGGGAGTTTACCCAGG
GCCCCCTGCTAGTTGAGCGGGACAGGGGACCCTGTGTTCTCACTGTGATTTGCAACTGTCCTAA
CCTTGGATTACATCAAGATCCTCTAGTTATAACTAGAGTACCCGGGGATCTTATTCCCTTTAACTA
ATAAAAAAAAATAATAAAGCATCACTTACTTAAAATCAGTTAGCAAATTTCTGTCCAGTTTATTCAG
GAGCACCTCCTTGCGCTCCTCCCAGCTCTGGTATTGGAGCTTCCTCCTGGCTGCAAACTTTCTCC
ACAATCTAAATGGAATGTCAGTTTCCTCCTGTTCCTGTCCATCCGCACCCACTATCTTCATGTTGT
TGCAGATGAAGCGCGCAAGACCGTCTGAAGATACCTTCAACCCCGTGTATCCATATGACACGGAA
ACCGGTCCTCCAACTGTGCCTTTTCTTACTCCTCCCTTTGTATCCCCCAATGGGTTTCAAGAGAGT
CCGCCTGGGGTACTCTCTTTGCGCCTATCCGAACCTCTAGTTACCTCCAATGGCATGCTTGCGCT
CAAAATGGGCAACGGCCTCTCTCTGGACGAGGCCGGCAACCTTACCTCCCAAAATGTAACCACT
GTGAGCCCACCTCTCAAAAAAACCAAGTCAAACATAAACCTGGAAATATCTGCACCCCTCACAGT
TACCTCAGAAGCCCTAACTGTGGCTGCCGCCGCACCTCTAATGGTCGCGGGCAACACACTCACC
ATGCAATCAGAGGCCGCGCTAACCGTGCAGGACTCCAAACTTAGGATTGCCACCCAAGGACCCC
TCACAGTGTCAGAAGGAAAGCTAGCCCTGCAAACATCAGGCCCCCTCACCACCACCGATAGCAG
TACCCTTACTATCACTGCCTCACCCCCTCTAACTACTGCCACTGGTAGCTTGGGCATTGACTTGAA
AGAGCCCATTTATACACAAAATGGAAAACTAGGACTAAAGTACGGGGCTCCTTTGCATGTAACAG
ACGAGCTAAACACTTTGACCGTAGCAACTGGTCCAGGTGTGACTATTAATAATACTTCCTTGCAAA
CTAAAGTTACTGGAGCCTTGGGTTTTGATTCACAAGGCAATATGCAACTTAATGTAGCAGGAGGA
CTAAGGATTGATTCTCAAAACAGACGCCTTATACTTGATGTTAGTTATCCGTTTGATGCTCAAAAC
CAACTAAATCTAAGACTAGGACAGGGCCCTCTTTTTATAAACTCAGCCCACAACTTGGATATTAAC
TACAACAAAGGCCTTTACTTGTTTACAGCTTCAAACAATTCCAAAAAGCTTGAGGTTAACCTAAGC
ACTGCCAAGGGGTTGATGTTTGACGCTACAGCCATAGCCATTAATGCAGGAGATGGGCTTGAATT
TGGTTCACCTAATGCACCAAACACAAATCCCCTCAAAACAAAAATTGGCCATGGCCTAGAATTTGA
TTCAAACAAGGCTATGGTTCCTAAACTAGGAACTGGCCTTAGTTTTGACAGCACAGGTGCCATTA
CAGTAGGAAACAAAATAATGATAAGCTAACTTTGTGGACCACACCAGCTCCATCTCCTAACTGTA
GACTAAATGCAGAGAAAGATGCTAAACTCACTTTGGTCTTAACAAAATGTGGCAGTCAAATACTTG
CTACAGTTTCAGTTTTGGCTGTTAAAGGCAGTTTGGCTCCAATATCTGGAACAGTTCAAAGTGCTC
ATCTTATTATAAGATTTGACGAAAATGGAGTGCTACTAAACAATTCCTTCCTGGACCCAGAATATT
GGAACTTTAGAAATGGAGATCTTACTGAAGGCACAGCCTATACAAACGCTGTTGGATTTATGCCTA
```

-continued

ACCTATCAGCTTATCCAAAATCTCACGGTAAAACTGCCAAAAGTAACATTGTCAGTCAAGTTTACT

TAAACGGAGACAAAACTAAACCTGTAACACTAACCATTACACTAAACGGTACACAGGAAACAGGA

GACACAACTCCAAGTGCATACTCTATGTCATTTTCATGGGACTGGTCTGGCCACAACTACATTAAT

GAAATATTTGCCACATCCTCTTACACTTTTTCATACATTGCCCAAGAATAAAGAATCGTTTGTGTTA

TGTTTGAACGTGTTTATTTTTCAATTGCAGAAAATTTCAAGTCATTTTTGATTGAGTAGTATAGGCC

CACCACCACATAGCTTATACAGATCACCGTACCTTAATCAAAC pSSI10902 (SEQ ID NO: 2):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGGAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGGAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGACAGGCCCGAAGGAATAGAAGAAGAAGGTGGAGAGAG

AGACAGAGACAGATCCATTCGATTAGTGAACGGATCTCGACGGTATCGATTGGGCCCGAGATCT

CGCGCGCGAGGCCTGCCATGGGCATGCCTGCAGGTCGATGCGTGGCCGGCCTAGGATCCATAT

GGTACCGGTAAATGGCCCGCCTGGCTGACCGCCCAACGACCCCCGCCCATTGACGTCAATAATG

ACGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGG

GTGGATAGCGGTTTGACTCACGGGGATTTCCAAGTCTCCACCCCATTGACGTCAATGGGAGTTTG

-continued

```
TTTTGGCACCAAAATCAACGGGACTTTCCAAAATGTCGTAACAACTCCGCCCCATTGACGCAAAT
GGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCC
GCGGCCGGGAACGGTGCATTGGAACGCGGATTCCCCGTGCCAAGAGTGACGTAAGTACCGCCT
ATAGACTCTATAGGCACACCCCTTTGGCTCTTATGCATGAATTAATAGGACTCACTATAGGGAGAC
AGACTGTTCCTTTCCTGGGTCTTTTCTGCAGGCTAGCCCCACCATGCCGCGCGCTCCCCGCTGC
CGAGCCGTGCGCTCCCTGCTGCGCAGCCACTACCGCGAGGTGCTGCCGCTGGCCACGTTCGTG
CGGCGCCTGGGGCCCCAGGGCTGGCGGCTGGTGCAGCGCGGGGACCCGGCGGCTTTCCGCG
CGCTGGTGGCCCAGTGCCTGGTGTGCGTGCCCTGGGACGCACGGCCGCCCCCGCCGCCGCC
TCCTTCCGCCAGGTGTCCTGCCTGAAGGAGCTGGTGGCCCGAGTGCTGCAGAGGCTGTGCGAG
CGCGGCGCGAAGAACGTGCTGGCCTTCGGCTTCGCGCTGCTGGACGGGGCCCGCGGGGGCCC
CCCCGAGGCCTTCACCACCAGCGTGCGCAGCTACCTGCCCAACACGGTGACCGACGCACTGCG
GGGGAGCGGGGCGTGGGGGCTGCTGTTGCGCCGCGTGGGCGACGACGTGCTGGTTCACCTGC
TGGCACGCTGCGCGCTCTTTGTGCTGGTGGCTCCCAGCTGCGCCTACCAGGTGTGCGGGCCGC
CGCTGTACCAGCTCGGCGCTGCCACTCAGGCCCGGCCCCCGCCACACGCTAGTGGACCCCGAA
GGCGTCTGGGATGCGAACGGGCCTGGAACCATAGCGTCAGGGAGGCCGGGGTCCCCCTGGGC
CTGCCAGCCCCGGGTGCGAGGAGGCGCGGGGGCAGTGCCAGCCGAAGTCTGCCGTTGCCCAA
GAGGCCCAGGCGTGGCGCTGCCCCTGAGCCGGAGCGGACGCCCGTTGGGCAGGGGTCCTGGG
CCCACCCGGGCAGGACGCGTGGACCGAGTGACCGTGGTTTCTGTGTGGTGTCACCTGCCAGAC
CCGCCGAAGAAGCCACCTCTTTGGAGGGTGCGCTCTCTGGCACGCGCCACTCCCACCCATCCGT
GGGCCGCCAGCACCACGCGGGCCCCCCATCCACATCGCGGCCACCACGTCCCTGGGACACGC
CTTGTCCCCCGGTGTACGCCGAGACCAAGCACTTCCTCTACTCCTCAGGCGACAAGGAGCAGCT
GCGGCCCTCCTTCCTACTCAGCTCTCTGAGGCCCAGCCTGACTGGCGCTCGGAGGCTCGTGGA
GACCATCTTTCTGGGTTCCAGGCCCTGGATGCCAGGGACTCCCCGCAGGTTGCCCCGCCTGCC
CCAGCGCTACTGGCAAATGCGGCCCCTGTTTCTGGAGCTGCTTGGGAACCACGCGCAGTGCCC
CTACGGGGTGCTCCTCAAGACGCACTGCCCGCTGCGAGCTGCGGTCACCCCAGCAGCCGGTGT
CTGTGCCCGGGAGAAGCCCCAGGGCTCTGTGGCGGCCCCGAGGAGGAGGACACAGACCCCC
GTCGCCTGGTGCAGCTGCTCCGCCAGCACAGCAGCCCTGGCAGGTGTACGGCTTCGTGCGGG
CCTGCCTGCGCCGGCTGGTGCCCCAGGCCTCTGGGGCTCCAGGCACAACGAACGCCGCTTCC
TCAGGAACACCAAGAAGTTCATCTCCCTGGGGAAGCATGCCAAGCTCTCGCTGCAGGAGCTGAC
GTGGAAGATGAGCGTGCGGGGCTGCGCTTGGCTGCGCAGGAGCCCAGGGGTTGGCTGTGTTCC
GGCCGCAGAGCACCGTCTGCGTGAGGAGATCCTGGCCAAGTTCCTGCACTGGCTGATGAGTGT
GTACGTCGTCGAGCTGCTCAGGTCTTTCTTTTATGTCACGGAGACCACGTTTCAAAAGAACAGGC
TCTTTTTCTACCGGAAGAGTGTCTGGAGCAAGTTGCAAAGCATTGGAATCAGACAGCACTTGAAG
AGGGTGCAGCTGCGGGAGCTGTCGGAAGCAGAGGTCAGGCAGCATCGGGAAGCCAGGCCCGC
CCTGCTGACGTCCAGACTCCGCTTCATCCCCAAGCCTGACGGGCTGCGGCCGATTGTGAACATG
GACTACGTCGTGGGAGCCAGAACGTTCCGCAGAGAAAAGAGGGCCGAGCGTCTCACCTCCAGG
GTGAAGGCACTGTTCAGCGTGCTCAACTACGAGCGGGCGCGGCGCCCGGCCTCCTGGGCGCC
TCTGTGCTGGGCCTGGACGATATCCACAGGGCCTGGCGCACCTTCGTGCTGCGTGTGCGGGCC
CAGGACCCGCCGCCTGAGCTGTACTTTGTCAAGGTGGATGTGACGGGCGCGTACGACACCATCC
CCCAGGACAGGCTCACGGAGGTCATCGCCAGCATCATCAAACCCCAGAACACGTACTGCGTGCG
```

-continued

```
TCGGTATGCCGTGGTCCAGAAGGCCGCCCATGGGCACGTCCGCAAGGCCTTCAAGAGCCACGT
CTCTACCTTGACAGACCTCCAGCCGTACATGCGACAGTTCGTGGCTCACCTGCAGGAGACCAGC
CCGCTGAGGGATGCCGTCGTCATCGAGCAGAGCTCCTCCCTGAATGAGGCCAGCAGTGGCCTC
TTCGAGGTCTTCCTACGCTTCATGTGCCACCACGCCGTGCGCATCAGGGGCAAGTCCTACGTCC
AGTGCCAGGGGATCCCGCAGGGCTCCATCCTCTCCACGCTGCTCTGCAGCCTGTGCTACGGCG
ACATGGAGAACAAGCTGTTTGCGGGGATTCGGCGGGACGGGCTGCTCCTGCGTTTGGTGGATG
ATTTCTTGTTGGTGACACCTCACCTCACCCACGCGAAAACCTTCCTCAGGACCCTGGTCCGAGGT
GTCCCTGAGTATGGCTGCGTGGTGAACTTGCGGAAGAGAGTGGTGAACTTCCCTGTAGAAGACG
AGGCCCTGGGTGGCACGGCTTTTGTTCAGATGCCGGCCCACGGCCTATTCCCCTGGTGCGGCC
TGCTGCTGGATACCCGGACCCTGGAGGTGCAGAGCGACTACTCCAGCTATGCCCGGACCTCCAT
CAGAGCCAGTCTCACCTTCAACCGCGGCTTCAAGGCTGGGAGGAACATGCGTCGCAAACTCTTT
GGGGTCTTGCGGCTGAAGTGTCACAGCCTGTTTCTGGATTTGCAGGTGAACAGCCTCCAGAGGG
TGTGCACCAACATCTACAAGATCCTCCTGCTGCAGGCGTACAGGTTTCACGCATGTGTGCTGCAG
CTCCCATTTCATCAGCAAGTTTGGAAGAACCCCACATTTTTCCTGCGCGTCATCTCTGACACGGC
CTCCCTCTGCTACTCCATCCTGAAAGCCAAGAACGCAGGGATGTCGCTGGGGGCCAAGGGCGC
CGCCGGCCCTCTGCCCTCCGAGGCCGTGCAGTGGCTGTGCCACCAAGCATTCCTGCTCAAGCT
GACTCGACACCGTGTCACCTACGTGCCACTCCTGGGGTCACTCAGGACAGCCCAGACGCAGCTG
AGTCGGAAGCTCCCGGGGACGACGCTGACTGCCCTGGAGGCCGCAGCCAACCCGGCACTGCC
CTCAGACTTCAAGACCATCCTGGACTGAGTCGAAACTCGAGGATCCGGCTGTGGAATGTGTGTC
AGTTAGGGTGTGGAAAGTCCCCAGGCTCCCCAGCAGGCAGAAGTATGCAAAGCATGCATCTCAA
TTAGTCAGCAACCAGGTGTGGAAAGTCCCCAGGCTCCCCAGCAGGCAGAAGTATGCAAAGCATG
CATCTCAATTAGTCAGCAACCATAGTCCCGCCCCTAACTCCGCCCATCCCGCCCCTAACTCCGCC
CAGTTCCGCCCATTCTCCGCCCCATGGCTGACTAATTTTTTTATTTATGCAGAGGCCGAGGCCG
CCTCGGCCTCTGAGCTATTCCAGAAGTAGTGAGGAGGCTTTTTGGAGGCCGTCGGCCGCCACG
ACCGGTGCCGCCACCATCCCCTGACCCACGCCCCTGACCCCTCACAAGGAGACGACCTTCCATG
ACCGAGTACAAGCCCACGGTGCGCCTCGCCACCCGCGACGACGTCCCCGGGCCGTACGCACC
CTCGCCGCCGCGTTCGCCGACTACCCTGCAACACGCCATACAGTGGACCCTGACCGCCACATCG
AGCGGGTCACCGAGCTGCAAGAACTCTTCCTCACGCGCGTCGGGCTCGACATCGGCAAGGTGT
GGGTCGCGGACGACGGCGCCGGTGGCGGTCTGGACCACGCCGGAGAGCGTCGAAGCGGG
GGCGGTGTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTCCTGGCCA
CCGTCGGCGTCTCGCCCGACCACCAGGGCAAGGGTCTGGGCAGCGCCGTCGTGCTCCCCGGA
GTGGAGGCGGCCGAGCGCGCCGGGGTGCCCGCCTTCCTGGAGACCTCCGCGCCCCGCAACCT
CCCCTTCTACGAGCGGCTCGGCTTCACCGTCACCGCCGACGTCGAGGTGCCCGAAGGACCGCG
CACCTGGTGCATGACCCGCAAGCCCGGTGCCTGACGCCCGCCCCACGACCCGCAGCGCCCGAC
CGAAAGGAGGGCACGACCCCATGCATCGATAAAATAAAAGATTTTATTTAGTCTCCAGAAAAAGG
GGGGAATGAAAGACCCCACCTGTAGGTTTGGCAAGCTAGGCCTATTAATATTCCGGAGTATACGT
AGCCGGCTAACGTTAACAACCGGTACGATGCATTAGTTATTAATAGTAATCAATTACGGGGTCATT
AGTTCATAGCCCATATATGGAGTTCCGCGTTACATAACTTACGGTAAATGGCCCGCCTGGCTGAC
CGCCCAACGACCGCCGCCCATTGACGTCAATAATGACGTATGTTCCCATAGTAAGGCCAATAGGG
ACTTTCCATTGACGTCAATGGGTGGAGTATTTACGGTAAACTGCCCACTTGGCAGTACATCAAGT
```

-continued

```
GTATCATATGCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCATCGCTATTA

CCATGGTGATGCGGTTTTGGCAGTACATCAATGGGCGTGGATAGGGGTTTGACTGAGGGGGATT

TCCAAGTCTCCACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTACGGTGGGAGGT

CTATATAAGCAGAGCTGGTTTAGTGAACCGTCAGATCCGCTAGCGCTACCGGACTCAGATCTCGA

GCTCAAGGTTCGAATTCTGCAGTCGACCCACCATGGCTCTTTCAAACAAGTTTATCGGAGATGAC

ATGAAAATGACCTACCATATGGATGGCTGTGTCAATGGGCATTACTTTACCGTCAAAGGTGAAGG

CAGCGGGAAGCCATACGAAGGGACGCAGACCTCGACTTTTAAAGTCACCATGGCCAACGGTGGG

CCCCTTGCATTCTCCTTTGACATACTATCTACAGTGTTCATGTATGGAAATCGATGCTTTACTGCG

TATCCTACCAGTATGCCCGACTATTTCAAACAAGCATTTCCTGACGGAATGTCATATGAAAGGACT

TTTACCTATGAAGATGGAGGAGTTGCTACAGCCAGTTGGGAAATAAGCCTTAAAGGCAACTGCTT

TGAGCACAAATCCACGTTTCATGGAGTGAACTTTCCTGCTGATGGACCTGTGATGGCGAAGATGA

CAACTGGTTGGGACCCATCTTTTGAGAAAATGACTGTCTGCGATGGAATATTGAAGGGTGATGTC

ACCGCGTTCCTCATGCTGCAAGGAGGTGGCAATTACAGATGCCAATTCCACACTTCTTACAAGAC

AAAAAAACCGGTGACGATGCCACCAAACCATGCGGTGGAACATCGCATTGCGAGGACCGACCTT

GACAAAGGTGGCAACAGTGTTCAGCTGACGGAGCACGCTGTTGCACATATAACCTCTGTTGTCCC

TTTCTAGCGGCCGCGATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGCTATTGCTTC

CCGTATGGCTTTCATTTTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAACCCCCACTGGTTGG

GGCATTGCCACCACCTGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGTTGGGCACTGACAA

TTCCGTGGTGTTGTCGGGGAAGCTGAGGTCCTTTCCATGGCTGCTCGCCTGTGTTGCCACCTGG

ATTCTGCGCGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGACGAGTCGGA

TCTCCCTTTGGGCCGCCTCCCCGCATCGGACGCGTGGTACCTTTAAGACCAATGACTTACAAGG

CAGCTGTAGATCTTAGCCACTTTTTAAAAGAAAAGGGGGGACTGGAAGGGCTAATTCACTCCCAA

CGAAGACAAGATCTGCTTTTTGCTTGTACTGGGTCTCTCTGGTTAGACCAGATCTGAGCCTGGGA

GCTCTCTGGCTAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTTTAGTCAGTG

TGGAAAATCTCTAGCAGTAGTAGTTCATGTCATCTTATTATTCAGTATTTATAACTTGCAAAGAAAT

GAATATCAGAGAGTGAGAGGAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAAACTCATCAA

TGTATCTTATCATGTCTGGCTCTAGCTATCCCGCCCCTAACTCCGCCCATCCCGCCCCTAACTCC

GCCCAGTTCCGCCCATTCTCCGCCCCATGGCTGACTAATTTTTTTATTTATGCAGAGGCCGAGG

CCGCCTCGGCCTCTGAGCTATTCCAGAAGTAGTGAGGAGGCTTTTTTGGAGGCCTAGGGACGTA

CCCAATTCGCCCTATAGTGAGTCGTATTACGCGCGCTCACTGGCCGTCGTTTTACAACGTCGTGA

CTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC
```

-continued

```
GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT
```

-continued pSSI12112 (SEQ ID NO: 3):
AATGTAGTCTTATGCAATACTCTTGTAGTCTTGCAACATGGTAACGATGAGTTAGCAACATGCCTT
ACAAGGAGAGAAAAAGCACCGTGCATGCCGATTGGTGGAAGTAAGGTGGTACGATCGTGCCTTA
TTAGGAAGGCAACAGACGGGTCTGACATGGATTGGACGAACCACTGAATTGCCGCATTGCAGAG
ATATTGTATTTAAGTGCCTAGCTCGATACATAAACGGGTCTCTCTGGTTAGACCAGATCTGAGCCT
GGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTC
AGTGTGGAAAATCTCTAGCAGTGGCGCCCGAACAGGGACTTGAAAGCGAAAGGGAAACCAGAGG
AGCTCTCTCGACGCAGGACTCGGCTTGCTGAAGCGCGCACGGCAAGAGGCGAGGGGCGGCGA
CTGGTGAGTACGCCAAAAATTTTGACTAGCGGAGGCTAGAAGGAGAGAGATGGGTGCGAGAGCG
TCAGTATTAAGCGGGGGAGAATTAGATCGCGATGGGAAAAAATTCGGTTAAGGCCAGGGGGAAA
GAAAAAATATAAATTAAAACATATAGTATGGGCAAGCAGGGAGCTAGAACGATTCGCAGTTAATCC
TGGCCTGTTAGAAACATCAGAAGGCTGTAGACAAATACTGGGACAGCTACAACCATCCCTTCAGA
CAGGATCAGAAGAACTTAGATCATTATATAATACAGTAGCAACCCTCTATTGTGTGCATCAAAGGA
TAGAGATAAAAGACACCAAGGAAGCTTTAGCAAGATAGAGGAAGAGCAAAACAAAAGTAAGACC
ACCGCACAGCAAGCGGCCGCTGATCTTCAGACCTGGAGGAGGAGATATGAGGGACAATTGGAG
AAGTGAATTATATAAATATAAAGTAGTAAAAATTGAACCATTAGGAGTAGCACCCACCAAGGCAAA
GAGAAGAGTGGTGCAGAGAGAAAAAGAGCAGTGGGAATAGGAGCTTTGTTCCTTGGGTTCTTG
GGAGCAGCAGGAAGCACTATGGGCGCAGCGTCAATGACGCTGACGGTACAGGCCAGACAATTAT
TGTCTGGTATAGTGCAGCAGCAGAACAATTTGCTGAGGGCTATTGAGGCGCAACAGCATCTGTTG
CAACTCACAGTCTGGGGCATCAAGCAGCTCCAGGCAAGAATCCTGGCTGTGGAAAGATACCTAA
AGGATCAACAGCTCCTGGGGATTTGGGGTTGCTCTGGAAAACTCATTTGCACCACTGCTGTGCCT
TGGAATGCTAGTTGGAGTAATAAATCTCTGGAACAGATTTGGAATCACACGACCTGGATGGAGTG
GGACAGAGAAATTAACAATTACACAAGCTTAATACACTCCTTAATTGAAGAATCGCAAAACCAGCA
AGAAAAGAATGAACAAGAATTATTGGAATTAGATAAATGGGCAAGTTTGTGGAATTGGTTTAACAT
AACAAATTGGCTGTGGTATATAAAATTATTCATAATGATAGTAGGAGGCTTGGTAGGTTTAAGAAT
AGTTTTTGCTGTACTTTCTATAGTGAATAGAGTTAGGCAGGGATATTCACCATTATCGTTTCAGAC
CCACCTCCCAACCCCGAGGGGACCCGAGAGGCCCGAAGGAATAGAAGAAGAAGGTGGAGAGAG
AGACAGAGACAGATCCATTCGATTAGTGAACGGATCTCGACGGTATCGATACTAGTAATTTTTCTG
CAGAAAACGTACCCGGGGATCCTCTAGGATCCCACCGAAAGGTTGCTCCTTAACACAGGCTAAG
GACCAGCTTCTTTGGGAGAGAACAGACGCAGGGGCGGGAGGGAAAAAGGGAGAGGCAGACGTC
ACTTCCCCTTGGCGGCTCTGGCAGCAGATTGGTCGGTTGAGTGGCAGAAAGGCAGACGGGGAC
TGGGCAAGGCACTGTCGGTGACATCACGGACAGGGCGACTTCTATGTAGATGAGGCAGCGCAG
AGGCTGCTGCTTCGCCACTTGCTGCTTCGCCACGAAGGAGTTCCCGTGCCCTGGGAGCGGGTTC
AGGACCGCGGATCGGAAGTGAGAATCCCAGCTGTGTGTCAGGGCTGGAAAGGGCTCGGGAGTG
CGCGGGGCAAGTGACCGTGTGTGTAAAGAGTGAGGCGTATGAGGCTGTGTCGGGGCAGAGCCC
GAAGATCCGGGTTGCGGAGGGTGGGCCTGGGAGGGGTGGTGGCCATTTTTTGTCTAACCCTAAC
TGAGAAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTCAGCT
GCTGGCCCGTTCGCCCCTCCCGGGGACCTGCGGCGGGTCGCCTGCCCAGCCCCCGAACCCCG
CCTGGAGGCCGCGGTCGGCCCGGGGCTTCTCCGGAGGCACCCACTGCCACCGCGAAGAGTTG -continued
GGCTCTGTCAGCCGCGGGTCTCTCGGGGGCGAGGGCGAGGTTCAGGCCTTTCAGGCCGCAGG

AAGAGGAACGGAGCGAGTCCCCGCGCGCGGCGCGATTCCCTGAGCTGTGGGACGTGCACCCA

GGACTCGGCTCACACATGCAGTTCGCTTTCCTGTTGGTGGGGGAACGCCGATCGTGCGCATCC

GTCACCCCTCGCCGGCAATGGGGGCTTGTGAACCCCCAAACCTGACTGACTGGGCCAGTGTGCT

GCAAATTGGCAGGAGACGTGAAGGCACCTCCAAAGTCGACTTTCTGGAGTTTCAAAAACAGACC

GTACATGTCCGCGGTCGCGACGTACCTACCGGGTAGGGGAGGCGCTTTTCCCAAGGCAGTCTG

GAGCATGCGCTTTAGCAGCCCCGCTGGGCACTTGGCGCTACACAAGTGGCCTCTGGCCTCGCA

CACATTCCACATCCACCGGTAGGCGCCAACCGGCTCCGTTCTTTGGTGGCCCCTTCGCGCCACC

TTCTACTCCTCCCCTAGTCAGGAAGTTCCCCCCCGCCCCGCAGCTCGCGTCGTGCAGGACGTGA

CAAATGGAAGTAGCACGTCTCACTAGTCTCGTGCAGATGGACAGCACCGCTGAGCAATGGAAGC

GGGTAGGCCTTTGGGGCAGCGGCCAATAGCAGCTTTGCTCCTTCGCTTTCTGGGCTCAGAGGCT

GGGAAGGGGTGGGTCCGGGGGCGGGCTCAGGGGCGGGCTCAGGGGCGGGGCGGGCGCCCG

AAGTCCTCCGGAGGCCCGGCATTCTGCACGCTTCAAAAGCGCACGTCTGCCGCGCTGTTCTCCT

CTTCCTCATCTCCGGGCCTTTCGACTCTAGACACGTGTTGACAATTAATCATCGGCATAGTATATC

GGCATAGTATAATACGAGAAGGTGAGGAACTAAACCATGGCCAAGCCTTTGTCTCAAGAAGAATC

CACCCTCATTGAAAGAGCAACGGCTACAATCAACAGCATCCCCATCTCTGAAGACTACAGCGTCG

CCAGCGCAGCTCTCTCTAGCGACGGCCGCATCTTCACTGGTGTCAATGTATATCATTTTACTGGG

GGACCTTGTGCAGAACTCGTGGTGCTGGGCACTGCTGCTGCGGCAGCTGGCAACCTGACTT

GTATCGTCGCGATCGGAAATGAGAAGAGGGGCATCTTGAGGCCCTGCGGAGGGTGCCGAGAGG

TGCTTCTCGATCTGCATCCTGGGATCAAAGCCATAGTGAAGGACAGTGATGGACAGCCGACGGC

AGTTGGGATTCGTGAATTGCTGCCCTCTGGTTATGTGTGGGAGGGCTAAGCACAATTCGAGCTC

GGTACGCGTATCGATGGCGCCAGCTGCAGGCGGCCGCCATATGCATCCTAGGCCTATTAATATT

CCGGAGTATACGTAGGCGGCTAACGTTAACAACCGGTACGATGCATTAGTTATTAATAGTAATCAA

TTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGCCCACTTGG

CAGTACATCAAGTGTATCATATGCCAAGTACGCCGCCTATTGAGGTCAATGAGGGTAAATGGCCC

GCCTGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGCACCAAAATC

AACGGGACTTTCCAAAATGTCGTAACAACTCCGCCCCATTGACGCAAATGGGCGGTAGGCGTGT

ACGGTGGGAGGTCTATATAAGCAGAGCTGGTTTAGTGAACCGTCAGATCCGCTAGCCCCACCAT

GCCGCGCGCTCCCCGCTGCCGAGCCGTGCGCTCCCTGCTGCGCAGCCACTACCGCGAGGTGCT

GCCGCTGGCCACGTTCGTGCGGCGCCTGGGGCCCCAGGGCTGGCGGCTGGTGCAGCGCGGG

GACCCGGCGGCTTTCCGCGCGCTGGTGGCCCAGTGCCTGGTGTGCGTGCCCTGGGACGCACG

GCCGCCCCCGCCGCCCCCTCCTTCCGCCAGGTGTCCTGCCTGAAGGAGCTGGTGGCCCGAGT

GCTGCAGAGGCTGTGCGAGCGCGGCGCGAAGAACGTGCTGGCCTTCGGCTTCGCGCTGCTGGA

CGGGGCCCGCGGGGGCCCCCCGAGGCCTTCACCACCAGCGTGCGCAGCTACCTGCCCAACA

CGGTGACCGACGCACTGCGGGGGAGCGGGGCGTGGGGCTGCTGTTGCGCCGCGTGGGCGA

CGACGTGCTGGTTCACCTGCTGGCACGCTGCGCGCTCTTTGTGCTGGTGGCTCCCAGCTGCGC

CTACCAGGTGTGCGGGCCGCCGCTGTACCAGCTCGGCGCTGCCACTCAGGCCCGGCCCCCGC

-continued

```
CACACGCTAGTGGACCCCGAAGGCGTCTGGGATGCGAACGGGCCTGGAACCATAGCGTCAGGG

AGGCCGGGGTCCCCCTGGGCCTGCCAGCCCCGGGTGCGAGGAGGCGCGGGGGCAGTGCCAG

CCGAAGTCTGCCGTTGCCCAAGAGGCCGAGGCGTGGCGCTGCCGCTGAGGCGGAGGGGAGGC

CCGTTGGGCAGGGGTCCTGGGCCCACCCGGGCAGGACGCGTGGACCGAGTGACCGTGGTTTCT

GTGTGGTGTCACCTGCCAGACCCGCCGAAGAAGCCACCTCTTTGGAGGGTGCGCTCTCTGGCAC

GCGCCACTCCCACCCATCCGTGGGCCGCCAGCACCACGCGGGCCCCCCATCCACATCGCGGCC

ACCACGTCCCTGGGACACGCCTTGTCCCCCGGTGTACGCCGAGACCAAGCACTTCCTCTACTCC

TCAGGCGACAAGGAGCAGCTGCGGCCCTCCTTCCTACTCAGCTCTCTGAGGCCCAGCCTGACTG

GCGCTCGGAGGCTCGTGGAGACCATCTTTCTGGGTTCCAGGCCCTGGATGCCAGGGACTCCCC

GCAGGTTGCCCCGCCTGCCCCAGGGCTACTGGCAAATGCGGCCGCTGTTTCTGGAGCTGCTTG

GGAACCACGCGCAGTGCCCCTACGGGGTGCTCCTCAAGACGCACTGCCCGCTGCGAGCTGCGG

TCACCCCAGCAGCCGGTGTCTGTGCCCGGGAGAAGCCCCAGGGCTCTGTGGCGGCCCCCGAG

GAGGAGGACACAGACCCCCGTCGCCTGGTGCAGCTGCTCCGCCAGCACAGCAGCCCCTGGCAG

GTGTAGGGCTTCGTGCGGGCCTGCCTGCGCCGGCTGGTGCCGCCAGGCCTCTGGGGCTCCAG

GCACAACGAACGCCGCTTCCTCAGGAACACCAAGAAGTTCATCTCCCTGGGGAAGCATGCCAAG

CTCTCGCTGCAGGAGCTGACGTGGAAGATGAGCGTGCGGGCTGCGCTTGGCTGCGCAGGAGC

CCAGGGGTTGGCTGTGTTCCGGCCGCAGAGCACCGTCTGCGTGAGGAGATCCTGGCCAAGTTC

CTGCACTGGCTGATGAGTGTGTACGTCGTCGAGCTGCTGAGGTCTTTCTTTTATGTCAGGGAGAG

CACGTTTCAAAAGAACAGGCTCTTTTTCTACCGGAAGAGTGTCTGGAGCAAGTTGCAAAGCATTG

GAATCAGACAGCACTTGAAGAGGGTGCAGCTGCGGGAGCTGTCGGAAGCAGAGGTCAGGCAGC

ATCGGGAAGCCAGGCCCGCCCTGCTGACGTCCAGACTCCGCTTCATCCCCAAGCCTGACGGGC

TGCGGCCGATTGTGAACATGGACTACGTCGTGGGAGCCAGAACGTTCCGCAGAGAAAAGAGGG

CCGAGCGTCTCACCTCCAGGGTGAAGGCACTGTTCAGCGTGCTCAACTACGAGCGGGCGCGGC

GCCCCGGCCTCCTGGGCGCCTCTGTGCTGGGCCTGGACGATATCCACAGGGCCTGGCGCACCT

TCGTGCTGCGTGTGCGGGCCCAGGACCCGCCGCCTGAGCTGTACTTTGTCAAGGTGGATGTGA

CGGGCGCGTACGACACCATCCCCCAGGACAGGCTCACGGAGGTCATCGCCAGCATCATCAAAC

CCCAGAACACGTACTGCGTGCGTCGGTATGCCGTGGTCCAGAAGGCCGCCCATGGGCACGTCC

GCAAGGCCTTCAAGAGCCACGTCTCTACCTTGACAGACCTCCAGCCGTACATGCGACAGTTCGT

GGCTCACCTGCAGGAGACCAGCCCGCTGAGGGATGCCGTCGTCATCGAGCAGAGCTCCTCCCT

GAATGAGGCCAGCAGTGGCCTCTTCGACGTCTTCCTACGCTTCATGTGCCACCACGCCGTGCGC

ATCAGGGGCAAGTCCTACGTCCAGTGCCAGGGGATCCCGCAGGGCTCCATCCTCTCCACGCTG

CTCTGCAGCCTGTGCTACGGCGACATGGAGAACAAGCTGTTTGCGGGGATTCGGCGGGACGGG

CTGCTCCTGCGTTTGGTGGATGATTTCTTGTTGGTGACACCTCACCTCACCCACGCGAAAACCTT

CCTCAGGACCCTGGTCCGAGGTGTCCCTGAGTATGGCTGCGTGGTGAACTTGCGGAAGACAGTG

GTGAACTTCCCTGTAGAAGAGGAGGCCCTGGGTGGCAGGGCTTTTGTTGAGATGCCGGCCCAGG

GCCTATTCCCCTGGTGCGGCCTGCTGCTGGATACCCGGACCCTGGAGGTGCAGAGCGACTACT

CCAGCTATGCCCGGACCTCCATCAGAGCCAGTCTCACCTTCAACCGCGGCTTCAAGGCTGGGAG

GAACATGCGTCGCAAACTCTTTGGGGTCTTGCGGCTGAAGTGTCACAGCCTGTTTCTGGATTTGC

AGGTGAAGAGCCTCCAGAGGGTGTGCACCAACATCTACAAGATCCTCCTGCTGCAGGCGTACAG

GTTTCACGCATGTGTGCTGCAGCTCCCATTTCATCAGCAAGTTTGGAAGAACCCCACATTTTTCCT

GCGCGTCATCTCTGACACGGCCTCCCTCTGCTACTCCATCCTGAAAGCCAAGAACGCAGGGATG
```

-continued

```
TCGCTGGGGGCCAAGGGCGCCGCCGGCCCTCTGCCCTCCGAGGCCGTGCAGTGGCTGTGCCA
CCAAGCATTCCTGCTCAAGCTGACTCGACACCGTGTCACCTACGTGCCACTCCTGGGGTCACTC
AGGACAGCCCAGACGCAGCTGAGTCGGAAGCTCCCGGGGACGACGCTGACTGCCCTGGAGGC
CGCAGCCAACCCGGCACTGCCCTCAGACTTCAAGACCATCCTGGACTGAGTCGAAACTCGCGGC
CGCATGCGTCGACGCGTATCGATGCATCTTAAGTAGATGTACCTTTAAGACCAATGACTTACAAG
GCAGCTGTAGATCTTAGCCACTTTTTAAAAGAAAAGGGGGGACTGGAAGGGCTAATTCACTCCCA
ACGAAGACAAGATCTGCTTTTTGCTTGTACTGGGTCTCTCTGGTTAGACCAGATCTGAGCCTGGG
AGCTCTCTGGCTAACTAGGGAACCCACTGCTTAAGCCTCAATAAAGCTTGCCTTGAGTGCTTCAA
GTAGTGTGTGCCCGTCTGTTGTGTGACTCTGGTAACTAGAGATCCCTCAGACCCTTTTAGTCAGT
GTGGAAAATCTCTAGCAGTAGTAGTTCATGTCATCTTATTATTCAGTATTTATAACTTGCAAAGAAA
TGAATATCAGAGAGTGAGAGGAACTTGTTTATTGCAGCTTATAATGGTTACAAATAAAGCAATAGC
ATCACAAATTTCACAAATAAAGCATTTTTTTCACTGCATTCTAGTTGTGGTTTGTCCAAACTCATCA
ATGTATCTTATCATGTCTGGCTCTAGCTATCCCGCCCCTAACTCCGCCCATCCCGCCCCTAACTC
CGCCCAGTTCCGCCCATTCTCCGCCCCATGGCTGACTAATTTTTTTATTTATGCAGAGGCCGAG
GCCGCCTCGGCCTCTGAGCTATTCCAGAAGTAGTGAGGAGGCTTTTTTGGAGGCCTAGGGACGT
ACCCAATTCGCCCTATAGTGAGTCGTATTACGCGCGCTCACTGGCCGTCGTTTTACAACGTCGTG
ACTGGGAAAACCCTGGCGTTACCCAACTTAATCGCCTTGCAGCACATCCCCCTTTCGCCAGCTGG
CGTAATAGCGAAGAGGCCCGCACCGATCGCCCTTCCCAACAGTTGCGCAGCCTGAATGGCGAAT
GGGACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTAC
GGCACCTCGACCCCAAAAAACTTGATTAGGGTGATGGTTCACGTAGTGGGCCATCGCCCTGATA
GACGGTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGGCCTAT
TGGTTAAAAAATGAGCTGATTTAACAAAAATTTAACGCGAATTTTAACAAAATATTAACGCTTACAA
TTTAGGTGGCACTTTTCGGGGAAATGTGCGCGGAACCCCTATTTGTTTATTTTTCTAAATACATTC
AAATATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGATAAC
ACTGCGGCCAACTTACTTCTGACAACGATCGGAGGACCGAAGGAGCTAACCGCTTTTTTGCACAA
CATGGGGGATCATGTAACTCGCCTTGATCGTTGGGAACCGGAGCTGAATGAAGCCATACCAAAC
GACGAGCGTGACACCACGATGCCTGTAGCAATGGCAACAACGTTGCGCAAACTATTAACTGGCG
AACTACTTACTCTAGCTTCCCGGCAACAATTAATAGACTGGATGGAGGCGGATAAAGTTGCAGGA
CCACTTCTGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGATTTAAAAC
```

-continued

```
TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGGGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT
```

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating an age-related disorder in a subject, the method comprising: administering to the subject a nucleic acid vector comprising a coding sequence for telomerase reverse transcriptase (TERT) to treat the subject for an age-related disorder selected from the group consisting of: reduced circulatory function, cardiovascular disease, loss of neuromuscular coordination, and combinations thereof.

2. The method of claim 1, wherein the vector further comprises a coding sequence for telomerase RNA (TR).

3. The method of claim 1, wherein the method is a gene therapy method.

4. The method of claim 1, wherein TERT is human TERT, or an active fragment or functional equivalent thereof.

5. The method of claim 4, wherein the functional equivalent is a nucleic acid having at least 80% or more sequence identity to human TERT.

6. The method of claim 1, wherein the nucleic acid sequence encoding TERT is operably linked to a regulatory sequence that drives expression of the coding sequence.

7. The method of claim 6, wherein the vector is a non-integrative vector.

8. The method of claim 6, wherein the vector is an adeno-associated virus-based vector.

9. The method of claim 6, wherein the vector is a lentivirus-based vector.

10. The method of claim 1, wherein the subject is a mammal.

11. The method of claim 10, wherein the subject is an adult mammal.

12. The method of claim 11, wherein the adult mammal is an aged adult mammal.

13. The method of claim 11, wherein the adult mammal is an adult human.

14. The method of claim 1, wherein the age-related disorder is a decrease in circulatory function.

15. The method of claim 1, wherein the age-related disorder is cardiovascular disease.

16. The method of claim 1, wherein the age-related disorder is a loss of neuromuscular coordination.

17. The method of claim 9, wherein the nucleic acid sequence encoding TERT is a ribonucleic acid (RNA) sequence.

18. The method of claim 17, wherein the nucleic acid sequence encoding TERT comprises multiple copies of the sequence encoding TERT.

19. The method of claim 18, wherein the lentivirus-based vector comprises nucleic acid sequences encoding regulatory sequences.

* * * * *

SEQUENCE LISTING

```
<160> NUMBER OF SEQ ID NOS: 3

<210> SEQ ID NO 1
<211> LENGTH: 38420
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (2450)..(2450)
<223> OTHER INFORMATION: n is a, c, g, or t
```

```
<400> SEQUENCE: 1
tcacagaacc ctagtattca acctgccacc tccctcccaa cacacagagt acacagtcct      60
ttctccccgg ctggccttaa aaagcatcat atcatgggta acagacatat tcttaggtgt     120
tatattccac acggtttcct gtcgagccaa acgctcatca agtgatatta ataaactccc     180
cgggcagctc acttaagttc atgtcgctgt ccagctgctg agccacaggc tgctgtccaa     240
cttgcggttg cttaacgggc ggcgaaggag aagtccacgc ctacatgggg ggagagtcat     300
aatcgtgcat caggataggg cggtggtgct gcagcagcgc gcgaataaac tgctgccgcc     360
gccgctccgt cctgcaggaa tacaacatgg cagtggtctc ctcagcgatg attcgcaccg     420
cccgcagcat aaggcgcttg tcctccgggc acagcagcgc accctgatct cacttaaatc     480
agcacagtaa ctgcagcaca gcaccacaat attgttcaaa atcccacagt gcaaggcgct     540
gtatccaaag ctcatggcgg ggaccacaga acccacgtgg ccatcatacc acaagcgcag     600
gtagattaag tggcgacccc tcataaacac gctggacata acattacct cttttggcat      660
gttgtaattc accacctccc ggtaccatat aaacctctga ttaaacatgg cgccatccac     720
caccatccta aaccagctgg ccaaaacctg ccccgccggg ntatacactg cagggaaccg     780
ggacttggac aatgacaagt gggagagccc aggactcgta accatggatc atcatgctcg     840
tcatgatatc aatgttggca caacacaggc acacgtgcat acacttcctc aggattacaa     900
gctcctcccg cgttagaacc atatcccagg gaacaaccca ttcctgaatc agcgtaaatc     960
ccacactgca gggaagacct cgcacgtaac tcacgttgtg cattgtcaaa gtgttacatt    1020
cgggcagcag cggatgatcc tccagtatgg tagcgcgggt ttctgtctca aaaggaggta    1080
gacgatccct actgtacgga gtgcgccgag acaaccgaga tcgtgttggt cgtagtgtca    1140
tgccaaatgg aacgccggac gtagtcatat ttcctgaagc aaaaccaggt gcgggcgtga    1200
caaacagatc tgcgtctccg gtctcgccgc ttagatcgct ctgtgtagta gttgtagtat    1260
atccactctc tcaaagcatc caggcgcccc ctggcttcgg gttctatgta aactccttca    1320
tgcgccgctg ccctgataac atccaccacc gcagaataag ccacacccag ccaacctaca    1380
cattcgttct gcgagtcaca cacggggagga gcgggaagag ctggaagaac catgttttt    1440
ttttattcc aaaagattat ccaaaacctc aaaatgaaga tctattaagt gaacgcgctc    1500
ccctccggtg gcgtggtcaa actctacagc caaagaacag ataatggcat ttgtaagatg    1560
ttgcacaatg gcttccaaaa ggcaaacggc cctcacgtcc aagtggacgt aaaggctaaa    1620
cccttcaggg tgaatctcct ctataaacat tccagcacct tcaaccatgc ccaaataatt    1680
ctcatctcgc caccttctca atatatctct aagcaaatcc gaatattta agtccgggcc    1740
attgtaaaaa atttggctcc agagcgccct ccaccttcag cctcaagcag cgaatcatga    1800
ttgcaaaaat tcaggttcct cacagacctg tataagattc aaaagcggaa cattaacaaa    1860
aataccgcga tcccgtaggt cccttcgcag ggccagctga acataatcgt gcaggtctgc    1920
acggaccagc gcggccactt ccccgccagg aaccatgaca aaagaaccca cactgattat    1980
gacacgcata ctcggagcta tgctaaccag cgtagccccg atgtaagctt gttgcatggg    2040
cggcgatata aaatgcaagg tgctgctcaa aaaatcaggc aaagcctcgc gcaaaaaaga    2100
aagcacatcg tagtcatgct catgcagata aaggcaggta agctccggaa ccaccacaga    2160
aaaagacacc attttctct caaacatgtc tgcgggtttc tgcataaaca caaaataaaa    2220
taacaaaaaa acatttaaac attagaagcc tgtcttacaa caggaaaaac aacccttata    2280
agcataagac ggactacggc catgccggcg tgaccgtaaa aaaactggtc accgtgatta    2340
```

```
aaaagcacca ccgacagctc ctcggtcagt ccggagtcat aatgtaagac tcggtaaaca    2400
catcaggttg attcacatcg gtcagtgtta aaaagcgacc gaaatagccn ggggaatac     2460 aatacccgca ggcgtagaga caacattaca gcccccatag gaggtataac aaaattaata    2520
ggagagaaaa acacataaac acctgaaaaa ccctcctgcc taggcaaaat agcaccctcc    2580
cgctccagaa caacatacag cgcttccaca gcggcagcca taacagtcag ccttaccagt    2640 aaaaagaaa acctattaaa aaacaccac tcgacacggc accagctcaa tcagtcacag      2700
tgtaaaaaag gccaagtgc agagcgagta tataggac taaaaaatga cggtaacggt       2760
taaagtccac aaaaaacacc cagaaaaccg cacgcgaacc tacgcccaga acgaaagcc     2820 aaaaaaccca caacttcctc aaatcgtcac ttccgttttc ccacgttacg tcacttccca    2880
ttttaagaaa actacaattc ccaacacata caagttactc cgccctaaaa cctacgtcac    2940 ccgcccgtt cccacgcccc cgccacgtc acaaactcca ccccctcatt atcatattgg      3000
cttcaatcca aaataaggta tattattgat gatgttaatt aacatgcatg gatccatatg    3060
cggtgtgaaa taccgcacag atgcgtaagg agaaaatacc gcatcaggcg ctcttccgct    3120
tcctcgctca ctgactcgct gcgctcggtc gttcggctgc ggcgagcggt atcagctcac    3180
tcaaaggcgg taatacggtt atccacagaa tcaggggata cgcaggaaa gaacatgtga    3240 gcaaaaggcc agcaaaggc caggaaccgt aaaaaggccg cgttgctggc gttttttccat    3300 aggctccgcc cccctgacga gcatcacaaa atcgacgct caagtcagag gtggcgaaac    3360
ccgacaggac tataaagata ccaggcgttt ccccctggaa gctccctcgt gcgctctcct    3420
gttccgaccc tgccgcttac cggatacctg tccgcctttc tcccttcggg aagcgtggcg    3480
ctttctcata gctcacgctg taggtatctc agttcggtgt aggtcgttcg ctccaagctg    3540
ggctgtgtgc acgaaccccc cgttcagccc gaccgctgcg ccttatccgg taactatcgt    3600
cttgagtcca acccggtaag acacgactta tcgccactgg cagcagccac tggtaacagg    3660
attagcagag cgaggtatgt aggcggtgct acagagttct tgaagtggtg cctaactac     3720 ggctacacta gaaggacagt atttggtatc tgcgctctgc tgaagccagt taccttcgga    3780
aaaagagttg gtagctcttg atccggcaaa caaaccaccg ctggtagcgg tggtttttt     3840 gtttgcaagc agcagattac gcgcagaaaa aaaggatctc aagaagatcc tttgatcttt    3900
tctacggggt ctgacgctca gtggaacgaa aactcacgtt aagggatttt ggtcatgaga    3960
ttatcaaaaa ggatcttcac ctagatcctt ttaaattaaa aatgaagttt taaatcaatc    4020
taaagtatat atgagtaaac ttggtctgac agttaccaat gcttaatcag tgaggcacct    4080
atctcagcga tctgtctatt tcgttcatcc atagttgcct gactccccgt cgtgtagata    4140
actacgatac gggagggctt accatctggc cccagtgctg caatgatacc gcgagaccca    4200
cgctcaccgg ctccagattt atcagcaata aaccagccag ccggaagggc cgagcgcaga    4260
agtggtcctg caactttatc cgcctccatc cagtctatta attgttgccg ggaagctaga    4320
gtaagtagtt cgccagttaa tagtttgcgc aacgttgttg ccattgctgc agccatgaga    4380
ttatcaaaaa ggatcttcac ctagatcctt ttcacgtaga aagccagtcc gcagaaacgg    4440
tgctgacccc ggatgaatgt cagctactgg gctatctgga caaggaaaaa cgcaagcgca    4500
aagagaaagc aggtagcttg cagtgggctt acatggcgat agctagactg gcggttttta    4560
tggacagcaa gcgaaccgga attgccagct ggggcgccct ctggtaaggt tgggaagccc    4620
tgcaaagtaa actggatggc tttcttgccg ccaaggatct gatggcgcag gggatcaagc    4680
tctgatcaag agacaggatg aggatcgttt cgcatgattg aacaagatgg attgcacgca    4740
```

```
ggttctccgg ccgcttgggt ggagaggcta ttcggctatg actgggcaca acagacaatc    4800
ggctgctctg atgccgccgt gttccggctg tcagcgcagg ggcgcccggt tcttttttgtc   4860 aagaccgacc tgtccggtgc cctgaatgaa ctgcaagacg aggcagcgcg gctatcgtgg    4920
ctggccacga cgggcgttcc ttgcgcagct gtgctcgacg ttgtcactga agcgggaagg    4980
gactggctgc tattgggcga agtgccgggg caggatctcc tgtcatctca ccttgctcct    5040
gccgagaaag tatccatcat ggctgatgca atgcggcggc tgcatacgct tgatccggct    5100
acctgcccat tcgaccacca agcgaaacat cgcatcgagc gagcacgtac tcggatggaa    5160
gccggtcttg tcgatcagga tgatctggac gaagagcatc aggggctcgc gccagccgaa    5220
ctgttcgcca ggctcaaggc gagcatgccc gacggcgagg atctcgtcgt gacccatggc    5280
gatgcctgct tgccgaatat catggtggaa aatggccgct tttctggatt catcgactgt    5340
ggccggctgg gtgtggcgga ccgctatcag gacatagcgt tggctacccg tgatattgct    5400
gaagagcttg gcggcgaatg ggctgaccgc ttcctcgtgc tttacggtat cgccgctccc    5460
gattcgcagc gcatcgcctt ctatcgcctt cttgacgagt tcttctgaat tttgttaaaa    5520
tttttgttaa atcagctcat tttttaacca ataggccgaa atcggcaaca tcccttataa    5580
atcaaaagaa tagaccgcga tagggttgag tgttgttcca gtttggaaca agagtccact    5640
attaaagaac gtggactcca acgtcaaagg gcgaaaaacc gtctatcagg gcgatggccc    5700
actacgtgaa ccatcaccca atcaagtttt ttgcggtcg aggtgccgta aagctctaaa    5760
tcggaaccct aaagggagcc ccgatttag agcttgacgg ggaaagccgg cgaacgtggc    5820
gagaaaggaa gggaagaaag cgaaaggagc gggcgctagg gcgctggcaa gtgtagcggt    5880
cacgctgcgc gtaaccacca cacccgcgcg cttaatgcgc cgctacaggg cgcgtccatt    5940
cgccattcag gatcgaatta attcttaatt aacatcatca ataatatacc ttattttgga    6000
ttgaagccaa tatgataatg agggggtgga gtttgtgacg tggcgcgggg cgtgggaacg    6060
gggcgggtga cgtagtagtg tggcggaagt gtgatgttgc aagtgtggcg gaacacatgt    6120
aagcgacgga tgtggcaaaa gtgacgtttt tggtgtgcgc cggtgtacac aggaagtgac    6180
aattttcgcg cggttttagg cggatgttgt agtaaatttg ggcgtaaccg agtaagattt    6240
ggccattttc gcgggaaaac tgaataagag gaagtgaaat ctgaataatt ttgtgttact    6300
catagcgcgt aatactggta ccgcggccgc ctcgagtcta gagatatcga attcaagctt    6360
aaggtgcacg gcccacgtgg ccactagtaa tttttctgca gaaaacgtac ccggggatcc    6420
tctaggatcc caccgaaagg ttgctcctta acacaggcta aggaccagct tctttgggag    6480
agaacagacg caggggcggg agggaaaaag ggagaggcag acgtcacttc cccttggcgg    6540
ctctggcagc agattggtcg gttgagtggc agaaaggcag acgggactg ggcaaggcac    6600 tgtcggtgac atcacggaca gggcgacttc tatgtagatg aggcagcgca gaggctgctg    6660
cttcgccact tgctgcttcg ccacgaagga gttcccgtgc cctgggagcg ggttcaggac    6720
cgcggatcgg aagtgagaat cccagctgtg tgtcagggct ggaaagggct cgggagtgcg    6780
cggggcaagt gaccgtgtgt gtaaagagtg aggcgtatga ggctgtgtcg gggcagagcc    6840
cgaagatccg ggttgcggag ggtgggcctg ggaggggtga tggccatttt ttgtctaacc    6900
ctaactgaga agggcgtagg cgccgtgctt ttgctccccg cgcgctgttt ttctcgctga    6960
cttttcagcg gggcgaaaagc ctcggcctgc cgccttccac cgttcattct agagcaaaca    7020
aaaaatgtca gctgctggcc cgttcgcccc tccgggggac ctgcggcggg tcgcctgccc    7080
agcccccgaa ccccgcctgg aggccgcggt cggcccgggg cttctccgga ggcacccact    7140
```

```
gccaccgcga agagttgggc tctgtcagcc gcgggtctct cggggggcgag ggcgaggttc    7200 aggcctttca ggccgcagga agaggaacgg agcgagtccc cgcgcgcggc gcgattccct    7260
gagctgtggg acgtgcaccc aggactcggc tcacacatgc agttcgcttt cctgttggtg    7320
gggggaacgc cgatccgtgcg catccgtcac ccctcgccgg caatgggggc ttgtgaaccc    7380
ccaaacctga ctgactgggc cagtgtgctg caaattggca ggagacgtga aggcacctcc    7440
aaagtcgact ttctggagtt tcaaaaacag accgtacgat gcattagtta ttaatagtaa    7500
tcaattacgg ggtcattagt tcatagccca tatatggagt tccgcgttac ataacttacg    7560
gtaaatggcc cgcctggctg accgcccaac gaccccgcc cattgacgtc aataatgacg    7620
tatgttccca tagtaacgcc aatagggact ttccattgac gtcaatgggt ggagtattta    7680
cggtaaactg cccacttggc agtacatcaa gtgtatcata tgccaagtac gccccctatt    7740
gacgtcaatg acggtaaatg gcccgcctgg cattatgccc agtacatgac cttatgggac    7800
tttcctactt ggcagtacat ctacgtatta gtcatcgcta ttaccatggt gatgcggttt    7860
tggcagtaca tcaatgggcg tggatagcgg tttgactcac ggggatttcc aagtctccac    7920
cccattgacg tcaatgggag tttgttttgg caccaaaatc aacgggactt tccaaaatgt    7980
cgtaacaact ccgccccatt gacgcaaatg ggcggtaggc gtgtacggtg ggaggtctat    8040
ataagcagag ctggtttagt gaaccgtcag atccgctagc ccaccatgc cgcgcgctcc    8100 ccgctgccga gccgtgcgct ccctgctgcg cagccactac cgcgaggtgc tgccgctggc    8160
cacgttcgtg cggcgcctgg ggccccaggg ctggcggctg gtgcagcgcg gggacccggc    8220
ggctttccgc gcgctggtgg cccagtgcct ggtgtgcgtg ccctgggacg cacggccgcc    8280
ccccgccgcc ccctccttcc gccaggtgtc ctgcctgaag gagctggtgg cccgagtgct    8340
gcagaggctg tgcgagcgcg gcgcgaagaa cgtgctggcc ttcggcttcg cgctgctgga    8400 cgggcccgc gggggccccc ccgaggcctt caccaccagc gtgcgcagct acctgcccaa    8460
cacggtgacc gacgcactgc gggggagcgg ggcgtggggg ctgctgttgc gccgcgtggg    8520
cgacgacgtg ctggttcacc tgctggcacg ctgcgcgctc tttgtgctgg tggctcccag    8580
ctgcgcctac caggtgtgcg ggccgccgct gtaccagctc ggcgctgcca tcaggcccg    8640 gccccgcca cacgctagtg gaccccgaag gcgtctggga tgcgaacggg cctggaacca    8700
tagcgtcagg gaggccgggg tccccctggg cctgccagcc ccgggtgcga ggaggcgcgg    8760
gggcagtgcc agccgaagtc tgccgttgcc caagaggccc aggcgtggcg ctgcccctga    8820 gccgagcgg acgcccgttg ggcaggggtc ctgggcccac ccgggcagga cgcgtggacc    8880
gagtgaccgt ggtttctgtg tggtgtcacc tgccagaccc gccgaagaag ccacctcttt    8940
ggagggtgcg ctctctggca cgcgccactc ccacccatcc gtgggccgcc agcaccacgc    9000
gggcccccca tccacatcgc ggccaccacg tccctgggac acgccttgtc ccccggtgta    9060
cgccgagacc aagcacttcc tctactcctc aggcgacaag gagcagctgc ggccctcctt    9120
cctactcagc tctctgaggc ccagcctgac tggcgctcgg aggctcgtgg agaccatctt    9180
tctgggttcc aggccctgga tgccaggac tccccgcagg ttgccccgcc tgccccagcg    9240
ctactggcaa atgcggcccc tgtttctgga gctgcttggg aaccacgcgc agtgccccta    9300
cggggtgctc ctcaagacgc actgcccgct gcgagctgcg gtcaccccag cagccggtgt    9360
ctgtgcccgg gagaagcccc agggctctgt ggcggccccc gaggaggagg acacagaccc    9420
ccgtcgcctg gtgcagctgc tccgccagca cagcagcccc tggcaggtgt acggcttcgt    9480
gcgggcctgc ctgcgccggc tggtgccccc aggcctctgg ggctccaggc acaacgaacg    9540
```

-continued

```
ccgcttcctc aggaacacca agaagttcat ctccctgggg aagcatgcca agctctcgct    9600
gcaggagctg acgtggaaga tgagcgtgcg gggctgcgct tggctgcgca ggagcccagg    9660
ggttggctgt gttccggccg cagagcaccg tctgcgtgag gagatcctgg ccaagttcct    9720
gcactggctg atgagtgtgt acgtcgtcga gctgctcagg tctttctttt atgtcacgga    9780
gaccacgttt caaaagaaca ggctcttttt ctaccggaag agtgtctgga gcaagttgca    9840
aagcattgga atcagacagc acttgaagag ggtgcagctg cgggagctgt cggaagcaga    9900
ggtcaggcag catcgggaag ccaggcccgc cctgctgacg tccagactcc gcttcatccc    9960
caagcctgac gggctgcggc cgattgtgaa catggactac gtcgtgggag ccagaacgtt   10020
ccgcagagaa aagagggccg agcgtctcac ctccagggtg aaggcactgt tcagcgtgct   10080
caactacgag cgggcgcggc gccccggcct cctgggcgcc tctgtgctgg gcctggacga   10140
tatccacagg gcctggcgca ccttcgtgct gcgtgtgcgg gcccaggacc cgccgcctga   10200
gctgtacttt gtcaaggtgg atgtgacggg cgcgtacgac accatccccc aggacaggct   10260
cacggaggtc atcgccagca tcatcaaacc ccagaacacg tactgcgtgc gtcggtatgc   10320
cgtggtccag aaggccgccc atgggcacgt ccgcaaggcc ttcaagagcc acgtctctac   10380
cttgacagac ctccagccgt acatgcgaca gttcgtggct cacctgcagg agaccagccc   10440
gctgagggat gccgtcgtca tcgagcagag ctcctccctg aatgaggcca gcagtggcct   10500
cttcgacgtc ttcctacgct tcatgtgcca ccacgccgtg cgcatcaggg gcaagtccta   10560
cgtccagtgc caggggatcc cgcagggctc catcctctcc acgctgctct gcagcctgtg   10620
ctacggcgac atgagaaaca agctgttgc ggggattcgg cgggacgggc tgctcctgcg   10680
tttggtggat gatttcttgt tggtgacacc tcacctcacc cacgcgaaaa ccttcctcag   10740
gaccctggtc cgaggtgtcc ctgagtatgg ctgcgtggtg aacttgcgga agacagtggt   10800
gaacttccct gtagaagacg aggccctggg tggcacggct tttgttcaga tgccggccca   10860
cggcctattc ccctggtgcg gcctgctgct ggatacccgg accctggagg tgcagagcga   10920
ctactccagc tatgcccgga cctccatcag agccagtctc accttcaacc gcggcttcaa   10980
ggctgggagg aacatgcgtc gcaaactctt tggggtcttg cggctgaagt gtcacagcct   11040
gtttctggat ttgcaggtga acagcctcca gacggtgtgc accaacatct acaagatcct   11100
cctgctgcag gcgtacaggt ttcacgcatg tgtgctgcag ctcccatttc atcagcaagt   11160
ttggaagaac cccacatttt tcctgcgcgt catctctgac acggcctccc tctgctactc   11220
catcctgaaa gccaagaacg cagggatgtc gctgggggcc aagggcgccg ccggccctct   11280
gccctccgag gccgtgcagt ggctgtgcca ccaagcattc ctgctcaagc tgactcgaca   11340
ccgtgtcacc tacgtgccac tcctgggagtc actcaggaca gcccagacgc agctgagtcg   11400
gaagctcccg gggacgacgc tgactgccct ggaggccgca gccaacccgg cactgccctc   11460
agacttcaag accatcctgg actgagtcga aactcgcggc cgccatatgc atcctaggcc   11520
tattaatatt ccggagtata cgtagccggc taacgttaac ttgtttattg cagcttataa   11580
tggttacaaa taaagcaata gcatcacaaa tttcacaaat aaagcatttt tttcactgca   11640
ttctagttgt ggtttgtcca aactcatcaa tgtatcttaa cgcggatctg ggcgtggtta   11700
agggtgggaa agaatatata aggtgggggt cttatgtagt tttgtatctg ttttgcagca   11760
gccgccgccg ccatgagcac caactcgttt gatggaagca ttgtgagctc atatttgaca   11820
acgcgcatgc cccatgggc cggggtgcgt cagaatgtga tgggctccag cattgatggt   11880
cgccccgtcc tgcccgcaaa ctctactacc ttgacctacg agaccgtgtc tggaacgccg   11940
```

```
ttggagactg cagcctccgc cgccgcttca gccgctgcag ccaccgcccg cgggattgtg   12000
actgactttg ctttcctgag cccgcttgca agcagtgcag cttcccgttc atccgcccgc   12060
gatgacaagt tgacggctct tttggcacaa ttggattctt tgacccggga acttaatgtc   12120
gtttctcagc agctgttgga tctgcgccag caggtttctg ccctgaaggc ttcctcccct   12180
cccaatgcgg tttaaaacat aaataaaaaa ccagactctg tttggatttg gatcaagcaa   12240
gtgtcttgct gtctttattt aggggttttg cgcgcgcgt aggcccggga ccagcggtct   12300
cggtcgttga gggtcctgtg tatttttcc aggacgtggt aaaggtgact ctggatgttc   12360
agatacatgg gcataagccc gtctctgggg tggaggtagc accactgcag agcttcatgc   12420
tgcggggtgg tgttgtagat gatccagtcg tagcaggagc gctgggcgtg gtgcctaaaa   12480
atgtctttca gtagcaagct gattgccagg ggcaggccct tggtgtaagt gtttacaaag   12540
cggttaagct gggatgggtg catacgtggg gatatgagat gcatcttgga ctgtatttt   12600 aggttggcta tgttcccagc catatccctc cggggattca tgttgtgcag aaccaccagc   12660
acagtgtatc cggtgcactt gggaaatttg tcatgtagct tagaaggaaa tgcgtggaag   12720
aacttggaga cgcccttgtg acctccaaga ttttccatgc attcgtccat aatgatggca   12780
atgggcccac gggcggcggc ctgggcgaag atatttctgg gatcactaac gtcatagttg   12840
tgttccagga tgagatcgtc ataggccatt tttacaaagc gcgggcggag ggtgccagac   12900
tgcggtataa tggttccatc cggcccaggg gcgtagttac cctcacagat ttgcatttcc   12960
cacgctttga gttcagatgg ggggatcatg tctacctgcg gggcgatgaa gaaaacggtt   13020 tccgggtag gggagatcag ctgggaagaa agcaggttcc tgagcagctg cgacttaccg   13080
cagccggtgg gcccgtaaat cacacctatt accgggtgca actggtagtt aagagagctg   13140
cagctgccgt catccctgag caggggggcc acttcgttaa gcatgtccct gactcgcatg   13200
ttttccctga ccaaatccgc cagaaggcgc tcgccgccca gcgatagcag ttcttgcaag   13260
gaagcaaagt ttttcaacgg tttgagaccg tccgccgtag gcatgctttt gagcgtttga   13320
ccaagcagtt ccaggcggtc ccacagctcg gtcacctgct ctacggcatc tcgatccagc   13380
atatctcctc gtttcgcggg ttggggcgg tttcgctgta cggcagtagt cggtgctcgt   13440
ccagacgggc cagggtcatg tctttccacg ggcgcagggt cctcgtcagc gtagtctggg   13500
tcacggtgaa ggggtgcgct ccgggctgcg cgctggccag ggtgcgcttg aggctggtcc   13560
tgctggtgct gaagcgctgc cggtcttcgc cctgcgcgtc ggccaggtag catttgacca   13620
tggtgtcata gtccagcccc tccgcggcgt ggcccttggc gcgcagcttg cccttggagg   13680
aggcgccgca cgaggggcag tgcagacttt tgagggcgta gagcttgggc gcgagaaata   13740
ccgattccgg ggagtaggca tccgcgccgc aggccccgca gacggtctcg cattccacga   13800
gccaggtgag ctctggccgt tcggggtcaa aaaccaggtt tccccatgc tttttgatgc   13860 gtttcttacc tctggtttcc atgagccggt gtccacgctc ggtgacgaaa aggctgtccg   13920
tgtccccgta tacagacttg agaggcctgt cctcgagcgg tgttccgcgg tcctcctcgt   13980
atagaaactc ggaccactct gagacaaagg ctcgcgtcca ggccagcacg aaggaggcta   14040
agtgggaggg gtagcggtcg ttgtccacta ggggtccac tcgctccagg gtgtgaagac   14100
acatgtcgcc ctcttcggca tcaaggaagg tgattggttt gtaggtgtag ccacgtgac   14160 cgggtgttcc tgaaggggg ctataaaagg gggtggggc gcgttcgtcc tcactctctt   14220
ccgcatcgct gtctgcgagg gccagctgtt ggggtgagta ctccctctga aaagcgggca   14280
tgacttctgc gctaagattg tcagtttcca aaaacgagga ggatttgata ttcacctggc   14340
```

```
ccgcggtgat gcctttgagg gtggccgcat ccatctggtc agaaaagaca atctttttgt    14400
tgtcaagctt ggtggcaaac gacccgtaga gggcgttgga cagcaacttg gcgatggagc    14460
gcagggtttg gttttttgtcg cgatcggcgc gctccttggc cgcgatgttt agctgcacgt   14520
attcgcgcgc aacgcaccgc cattcgggaa agacggtggt gcgctcgtcg ggcaccaggt    14580
gcacgcgcca accgcggttg tgcagggtga caaggtcaac gctggtggct acctctccgc    14640
gtaggcgctc gttggtccag cagaggcggc cgcccttgcg cgagcagaat ggcggtaggg    14700
ggtctagctg cgtctcgtcc gggggtctg cgtccacggt aaagaccccg ggcagcaggc     14760
gcgcgtcgaa gtagtctatc ttgcatcctt gcaagtctag cgcctgctgc catgcgcggg    14820
cggcaagcgc gcgctcgtat gggttgagtg ggggacccca tggcatgggg tgggtgagcg    14880
cggaggcgta catgccgcaa atgtcgtaaa cgtagagggg ctctctgagt attccaagat    14940 atgtaggta gcatcttcca ccgcggatgc tggcgcgcac gtaatcgtat agttcgtgcg     15000
agggagcgag gaggtcggga ccgaggttgc tacgggcggg ctgctctgct cggaagacta    15060
tctgcctgaa gatggcatgt gagttggatg atatggttgg acgctggaag acgttgaagc    15120
tggcgtctgt gagacctacc gcgtcacgca cgaaggaggc gtaggagtcg cgcagcttgt    15180
tgaccagctc ggcggtgacc tgcacgtcta gggcgcagta gtccagggtt tccttgatga    15240
tgtcatactt atcctgtccc ttttttttcc acagctcgcg gttgaggaca aactcttcgc    15300
ggtctttcca gtactcttgg atcggaaacc cgtcggcctc cgaacggtaa gagcctagca    15360
tgtagaactg gttgacggcc tggtaggcgc agcatccctt ttctacgggt agcgcgtatg    15420
cctgcgcggc cttccggagc gaggtgtggg tgagcgcaaa ggtgtccctg accatgactt    15480
tgaggtactg gtatttgaag tcagtgtcgt cgcatccgcc ctgctcccag agcaaaaagt    15540
ccgtgcgctt tttggaacgc ggatttggca gggcgaaggt gacatcgttg aagagtatct    15600
ttcccgcgcg aggcataaag ttgcgtgtga tgcggaaggg tcccggcacc tcggaacggt    15660
tgttaattac ctgggcggcg agcacgatct cgtcaaagcc gttgatgttg tggcccacaa    15720
tgtaaagttc caagaagcgc gggatgccct tgatggaagg caattttta agttcctcgt     15780 aggtgagctc ttcaggggag ctgagcccgt gctctgaaag ggcccagtct gcaagatgag    15840
ggttggaagc gacgaatgag ctccacaggt cacgggccat tagcatttgc aggtggtcgc    15900
gaaaggtcct aaactggcga cctatggcca tttttttctgg ggtgatgcag tagaaggtaa   15960
gcgggtcttg ttcccagcgg tcccatccaa ggttcgcggc taggtctcgc gcggcagtca    16020
ctagaggctc atcccgccg aacttcatga ccagcatgaa gggcacgagc tgcttcccaa     16080
aggcccccat ccaagtatag gtctctacat cgtaggtgac aaagagacgc tcggtgcgag    16140
gatgcgagcc gatcgggaag aactggatct cccgccacca attggaggag tggctattga    16200
tgtggtgaaa gtagaagtcc ctgcgacggg ccgaacactc gtgctggctt ttgtaaaaac    16260
gtgcgcagta ctggcagcgg tgcacgggct gtacatcctg cacgaggttg acctgacgac    16320
cgcgcacaag gaagcagagt gggaatttga gcccctcgcc tggcgggttt ggctggtggt    16380
cttctacttc ggctgcttgt ccttgaccgt ctggctgctc gagggagtt acggtggatc     16440 ggaccaccac gccgcgcgag cccaaagtcc agatgtccgc gcgcggcggt cggagcttga    16500
tgacaacatc gcgcagatgg gagctgtcca tggtctggag ctcccgcggc gtcaggtcag    16560
gcgggagctc ctgcaggttt acctcgcata gacgggtcag ggcgcgggct agatccaggt    16620
gatacctaat ttccaggggc tggttggtgg cggcgtcgat ggcttgcaag aggccgcatc    16680
cccgcggcgc gactacggta ccgcgcggcg ggcggtgggc cgcgggggtg tccttggatg    16740
```

```
atgcatctaa aagcggtgac gcgggcgagc ccccggaggt agggggggct ccggacccgc   16800
cgggagaggg ggcaggggca cgtcggcgcc gcgcgcgggc aggagctggt gctgcgcgcg   16860
taggttgctg gcgaacgcga cgacgcggcg gttgatctcc tgaatctggc gcctctgcgt   16920
gaagacgacg ggcccggtga gcttgagcct gaaagagagt tcgacagaat caatttcggt   16980
gtcgttgacg gcggcctggc gcaaaatctc ctgcacgtct cctgagttgt cttgataggc   17040
gatctcggcc atgaactgct cgatctcttc ctcctggaga tctccgcgtc cggctcgctc   17100
cacggtggcg gcgaggtcgt tggaaatgcg ggccatgagc tgcgagaagg cgttgaggcc   17160
tccctcgttc cagacgcggc tgtagaccac gcccccttcg gcatcgcggg cgcgcatgac   17220
cacctgcgcg agattgagct ccacgtgccg ggcgaagacg gcgtagtttc gcaggcgctg   17280
aaagaggtag ttgagggtgg tggcggtgtg ttctgccacg aagaagtaca taacccagcg   17340
tcgcaacgtg gattcgttga tatcccccaa ggcctcaagg cgctccatgg cctcgtagaa   17400
gtccacggcg aagttgaaaa actgggagtt gcgcgccgac acggttaact cctcctccag   17460
aagacggatg agctcggcga cagtgtcgcg cacctcgcgc tcaaaggcta caggggcctc   17520
ttcttcttct tcaatctcct cttccataag ggcctcccct tcttcttctt ctggcggcgg   17580
tgggggaggg gggacacggc ggcgacgacg gcgcaccggg aggcggtcga caaagcgctc   17640
gatcatctcc ccgcggcgac ggcgcatggt ctcggtgacg gcgcggccgt tctcgcgggg   17700
gcgcagttgg aagacgccgc ccgtcatgtc ccggttatgg gttggcgggg ggctgccatg   17760
cggcagggat acggcgctaa cgatgcatct caacaattgt tgtgtaggta ctccgccgcc   17820
gagggacctg agcgagtccg catcgaccgg atcggaaaac ctctcgagaa aggcgtctaa   17880
ccagtcacag tcgcaaggta ggctgagcac cgtggcgggc ggcagcgggc ggcggtcggg   17940
gttgtttctg gcgcgaggtgc tgctgatgat gtaattaaag taggcggtct tgagacggcg   18000
gatggtcgac agaagcacca tgtccttggg tccggcctgc tgaatgcgca ggcggtcggc   18060
catgccccag gcttcgtttt gacatcggcg caggtctttg tagtagtctt gcatgagcct   18120
ttctaccggc acttcttctt ctccttcctc ttgtcctgca tctcttgcat ctatcgctgc   18180
ggcggcggcg gagtttggcc gtaggtggcg ccctcttcct cccatgcgtg tgaccccgaa   18240
gcccctcatc ggctgaagca gggctaggtc ggcgacaacg cgctcggcta atatggcctg   18300
ctgcacctgc gtgagggtag actgaagtc atccatgtcc acaaagcggt ggtatgcgcc   18360
cgtgttgatg gtgtaagtgc agttggccat aacggaccag ttaacggtct ggtgacccgg   18420
ctgcgagagc tcggtgtacc tgagacgcga gtaagccctc gagtcaaata cgtagtcgtt   18480
gcaagtccgc accaggtact ggtatcccac caaaaagtgc ggcggcggct ggcggtagag   18540
gggccagcgt agggtggccg gggctccggg ggcgagatct tccaacataa ggcgatgata   18600
tccgtagatg tacctggaca tccaggtgat gccggcggcg gtggtggagg cgcgcggaaa   18660
gtcgcggacg cggttccaga tgttgcgcag cggcaaaaag tgctccatgg tcgggacgct   18720
ctggccggtc aggcgcgcgc aatcgttgac gctctaccgt gcaaaaggag agcctgtaag   18780
cgggcactct tccgtggtct ggtggataaa ttcgcaaggg tatcatggcg gacgaccggg   18840
gttcgagccc cgtatccggc cgtccgccgt gatccatgcg gttaccgccc gcgtgtcgaa   18900
cccaggtgtg cgacgtcaga caacggggga gtgctccttt tggcttcctt ccaggcgcgg   18960
cggctgctgc gctagctttt ttggccactg gccgcgcgca gcgtaagcgg ttaggctgga   19020
aagcgaaagc attaagtggc tcgctccctg tagccggagg gttattttcc aagggttgag   19080
tcgcgggacc cccggttcga gtctcggacc ggccggactg cggcgaacgg gggtttgcct   19140
```

```
cccgtcatg caagacccg cttgcaaatt cctccggaaa cagggacgag ccccttttt     19200
gcttttccca gatgcatccg gtgctgcggc agatgcgccc cctcctcag cagcggcaag   19260
agcaagagca gcggcagaca tgcagggcac cctcccctcc tcctaccgcg tcaggagggg  19320
cgacatccgc ggttgacgcg gcagcagatg gtgattacga accccgcgg cgccgggccc   19380
ggcactacct ggacttggag gagggcgagg gcctggcgcg gctaggagcg ccctctcctg  19440
agcggtaccc aagggtgcag ctgaagcgtg atacgcgtga ggcgtacgtg ccgcggcaga  19500
acctgtttcg cgaccgcgag ggagaggagc ccgaggagat gcgggatcga aagttccacg  19560
cagggcgcga gctgcggcat ggcctgaatc gcgagcggtt gctgcgcgag gaggactttg  19620
agcccgacgc gcgaaccggg attagtcccg cgcgcgcaca cgtggcggcc gccgacctgg  19680
taaccgcata cgagcagacg gtgaaccagg agattaactt tcaaaaaagc tttaacaacc  19740
acgtgcgtac gcttgtggcg cgcgaggagg tggctatagg actgatgcat ctgtgggact  19800
ttgtaagcgc gctggagcaa aacccaaata gcaagccgct catggcgcag ctgttcctta  19860
tagtgcagca cagcagggac aacgaggcat tcagggatgc gctgctaaac atagtagagc  19920
ccgagggccg ctggctgctc gatttgataa acatcctgca gagcatagtg gtgcaggagc  19980
gcagcttgag cctggctgac aaggtggccg ccatcaacta ttccatgctt agcctgggca  20040
agttttacgc ccgcaagata taccataccc cttacgttcc catagacaag gaggtaaaga  20100
tcgaggggtt ctacatgcgc atggcgctga aggtgcttac cttgagcgac gacctgggcg  20160
tttatcgcaa cgagcgcatc cacaaggccg tgagcgtgag ccggcggcgc gagctcagcg  20220
accgcgagct gatgcacagc ctgcaaaggg ccctggctgg cacgggcagc ggcgatagag  20280
aggccgagtc ctactttgac gcgggcgctg acctgcgctg gccccaagc cgacgcgccc   20340
tggaggcagc tggggccgga cctggctggg cgtggcacc cgcgcgcgct ggcaacgtcg   20400
gcggcgtgga ggaatatgac gaggacgatg agtacgagcc agaggacggc gagtactaag  20460
cggtgatgtt tctgatcaga tgatgcaaga cgcaacggac ccggcggtgc gggcggcgct  20520
gcagagccag ccgtccggcc ttaactccac ggacgactgg cgccaggtca tggaccgcat  20580
catgtcgctg actgcgcgca atcctgacgc gttccggcag cagccgcagg ccaaccggct  20640
ctccgcaatt ctggaagcgg tggtcccggc gcgcgcaaac cccacgcacg agaaggtgct  20700
ggcgatcgta aacgcgctgg ccgaaaacag ggccatccgg cccgacgagg ccggcctggt  20760
ctacgacgcg ctgcttcagc gcgtggctcg ttacaacagc ggcaacgtgc agaccaacct  20820
ggaccggctg gtgggggatg tgcgcgaggc cgtggcgcag cgtgagcgcg cgcagcagca  20880
gggcaacctg ggctccatgg ttgcactaaa cgccttcctg agtacacagc ccgccaacgt  20940
gccgcgggga caggaggact acaccaactt tgtgagcgca ctgcggctaa tggtgactga  21000
gacaccgcaa agtgaggtgt accagtctgg gccagactat ttttccaga ccagtagaca   21060
aggcctgcag accgtaaacc tgagccaggc tttcaaaaac ttgcaggggc tgtgggggt   21120
gcgggctccc acaggcgacc gcgcgaccgt gtctagcttg ctgacgccca actcgcgcct  21180
gttgctgctg ctaatagcgc ccttcacgga cagtggcagc gtgtcccggg acacatacct  21240
aggtcacttg ctgacactgt accgcgaggc cataggtcag gcgcatgtgg acgagcatac  21300
tttccaggag attacaagtg tcagccgcgc gctggggcag gaggacacgg gcagcctgga  21360
ggcaaccctca aactacctgc tgaccaaccg gcggcagaag atcccctcgt tgcacagttt  21420
aaacagcgag gaggagcgca ttttgcgcta cgtcagcag agcgtgagcc ttaacctgat  21480
gcgcgacggg gtaacgccca gcgtggcgct ggacatgacc gcgcgcaaca tggaaccggg  21540
```

```
catgtatgcc tcaaaccggc cgtttatcaa ccgcctaatg gactacttgc atcgcgcggc   21600
cgccgtgaac cccgagtatt tcaccaatgc catcttgaac ccgcactggc taccgccccc   21660
tggtttctac accgggggat tcgaggtgcc cgagggtaac gatggattcc tctgggacga   21720
catagacgac agcgtgtttt ccccgcaacc gcagaccctg ctagagttgc aacagcgcga   21780
gcaggcagag gcggcgctgc gaaaggaaag cttccgcagg ccaagcagct tgtccgatct   21840
aggcgctgcg gccccgcggt cagatgctag tagcccattt ccaagcttga tagggtctct   21900
taccagcact cgcaccaccc gcccgcgcct gctgggcgag gaggagtacc taaacaactc   21960
gctgctgcag ccgcagcgcg aaaaaaacct gcctccggca tttcccaaca acgggataga   22020
gagcctagtg gacaagatga gtagatggaa gacgtacgcg caggagcaca gggacgtgcc   22080
aggcccgcgc ccgcccaccc gtcgtcaaag gcacgaccgt cagcggggtc tggtgtggga   22140
ggacgatgac tcggcagacg acagcagcgt cctggatttg ggagggagtg gcaacccgtt   22200
tgcgcacctt cgccccaggc tggggagaat gttttaaaaa aaaaaagca tgatgcaaaa   22260 taaaaaactc accaaggcca tggcaccgag cgttggtttt cttgtattcc ccttagtatg   22320
cggcgcgcgg cgatgtatga ggaaggtcct cctccctcct acgagagtgt ggtgagcgcg   22380
gcgccagtgg cggcggcgct gggttctccc ttcgatgctc ccctggaccc gccgtttgtg   22440
cctccgcggt acctgcggcc taccgggggg agaaacagca tccgttactc tgagttggca   22500
cccctattcg acaccacccg tgtgtacctg gtggacaaca agtcaacgga tgtggcatcc   22560
ctgaactacc agaacgacca cagcaacttt ctgaccacgg tcattcaaaa caatgactac   22620
agcccggggg aggcaagcac acagaccatc aatcttgacg accggtcgca ctggggcggc   22680
gacctgaaaa ccatcctgca taccaacatg ccaaatgtga acgagttcat gtttaccaat   22740
aagtttaagg cgcgggtgat ggtgtcgcgc ttgcctacta aggacaatca ggtggagctg   22800
aaatacgagt gggtggagtt cacgctgccc gagggcaact actccgagac catgaccata   22860
gaccttatga acaacgcgat cgtggagcac tacttgaaag tgggcagaca gaacgggagtt   22920 ctggaaagcg acatcggggt aaagtttgac acccgcaact tcagactggg gtttgacccc   22980
gtcactggtc ttgtcatgcc tgggtatat acaaacgaag ccttccatcc agacatcatt   23040
ttgctgccag gatgcgggt ggacttcacc cacagccgcc tgagcaactt gttgggcatc   23100
cgcaagcggc aaccccttcca ggagggcttt aggatcacct acgatgatct ggagggtggt   23160
aacattcccg cactgttgga tgtggacgcc taccaggcga gcttgaaaga tgacaccgaa   23220
cagggcgggg gtggcgcagg cggcagcaac agcagtggca gcgcgcggaa agagaactcc   23280
aacgcggcag ccgcggcaat gcagccggtg gaggacatga acgatcatgc cattcgcggc   23340 gacaccttg ccacacgggc tgaggagaag cgcgctgagg ccgaagcagc ggccgaagct   23400
gccgcccccg ctgcgcaacc cgaggtcgag aagcctcaga gaaaccggt gatcaaaccc   23460 ctgacagagg acagcaagaa acgcagttac aacctaataa gcaatgacag cacccttcacc   23520 cagtaccgca gctggtaccct tgcatacaac tacggcgacc ctcagaccgg aatccgctca   23580
tggaccctgc tttgcactcc tgacgtaacc tgcggctcgg agcaggtcta ctggtcgttg   23640
ccagacatga tgcaagaccc cgtgacctttc cgctccacgc gccagatcag caactttccg   23700
gtggtgggcg ccgagctgtt gccgtgcac tccaagagct tctacaacga ccaggccgtc   23760
tactcccaac tcatccgcca gtttaccct ctgacccacg tgttcaatcg ctttcccgag   23820
aaccagattt tggcgcgccc gccagccccc accatcacca ccgtcagtga aaacgttcct   23880
gctctcacag atcacgggac gctaccgctg cgcaacagca tcggaggagt ccagcgagtg   23940
```

```
accattactg acgccagacg ccgcacctgc ccctacgttt acaaggccct gggcatagtc  24000
tcgccgcgcg tcctatcgag ccgcactttt tgagcaagca tgtccatcct tatatcgccc  24060
agcaataaca caggctgggg cctgcgcttc ccaagcaaga tgtttggcgg ggccaagaag  24120
cgctccgacc aacacccagt gcgcgtgcgc gggcactacc gcgcgccctg gggcgcgcac  24180
aaacgcggcc gcactgggcg caccaccgtc gatgacgcca tcgacgcggt ggtggaggag  24240
gcgcgcaact acacgccac gccgccacca gtgtccacag tggacgcggc cattcagacc  24300
gtggtgcgcg gagcccggcg ctatgctaaa atgaagagac ggcggaggcg cgtagcacgt  24360
cgccaccgcc gccgacccgg cactgccgcc aacgcgcgg cggcggccct gcttaaccgc  24420
gcacgtcgca ccggccgacg ggcggccatg cgggccgctc gaaggctggc cgcgggtatt  24480
gtcactgtgc cccccaggtc caggcgacga gcggccgccg cagcagccgc ggccattagt  24540
gctatgactc agggtcgcag gggcaacgtg tattgggtgc gcgactcggt tagcggcctg  24600
cgcgtgcccg tgcgcacccg ccccccgcgc aactagattg caagaaaaaa ctacttagac  24660
tcgtactgtt gtatgtatcc agcggcggcg gcgcgcaacg aagctatgtc caagcgcaaa  24720
atcaaagaag agatgctcca ggtcatcgcg ccggagatct atggcccccc gaagaaggaa  24780
gagcaggatt acaagccccg aaagctaaag cgggtcaaaa agaaaaagaa agatgatgat  24840
gatgaacttg acgacgaggt ggaactgctg cacgctaccg cgcccaggcg acgggtacag  24900
tggaaaggtc gacgcgtaaa acgtgttttg cgacccggca ccaccgtagt ctttacgccc  24960
ggtgagcgct ccacccgcac ctacaagcgc gtgtatgatg aggtgtacgg cgacgaggac  25020
ctgcttgagc aggccaacga gcgcctcggg gagtttgcct acggaaagcg gcataaggac  25080
atgctggcgt tgccgctgga cgagggcaac ccaacaccta gcctaaagcc cgtaacactg  25140
cagcaggtgc tgcccgcgct tgcaccgtcc gaagaaaagc gcggcctaaa gcgcgagtct  25200
ggtgacttgg cacccaccgt gcagctgatg gtacccaagc gccagcgact ggaagatgtc  25260
ttggaaaaaa tgaccgtgga acctgggctg agcccgagg tccgcgtgcg gccaatcaag  25320
caggtggcgc cgggactggg cgtgcagacc gtggacgttc agatacccac taccagtagc  25380
accagtattg ccaccgccac agagggcatg gagacacaaa cgtccccggt tgcctcagcg  25440
gtggcggatg ccgcggtgca ggcggtcgct gcggccgcgt ccaagacctc tacggaggtg  25500
caaacgacc cgtggatgtt tcgcgtttca gccccccggc gcccgcgcgg ttcgaggaag  25560
tacggcgccg ccagcgcgct actgcccgaa tatgccctac atccttccat tgcgcctacc  25620
cccggctatc gtggctacac ctaccgcccc agaagacgag caactacccg acgccgaacc  25680
accactggaa cccgccgccg ccgtcgccgt cgccagcccg tgctggcccc gatttccgtg  25740
cgcagggtgg ctcgcgaagg aggcaggacc ctggtgctgc aacagcgcg ctaccacccc  25800
agcatcgttt aaaagccggt cttttgtggtt cttgcagata tggccctcac ctgccgcctc  25860
cgtttcccgg tgccgggatt ccgaggaaga atgcaccgta ggaggggcat ggccggccac  25920
ggcctgacgg gcggcatgcg tcgtgcgcac caccggcggc ggcgcgcgtc gcaccgtcgc  25980
atgcgcggcg gtatcctgcc cctccttatt ccactgatcg ccgcggcgat tggcgccgtg  26040
cccggaattg catccgtggc cttgcaggcg cagagacact gattaaaaac aagttgcatg  26100
tggaaaaatc aaaataaaaa gtctggactc tcacgctcgc ttggtcctgt aactatttg  26160
tagaatggaa gacatcaact ttgcgtctct ggccccgcga cacggctcgc gcccgttcat  26220
gggaaactgg caagatatcg gcaccagcaa tatgagcggt ggcgccttca gctgggctc  26280
gctgtggagc ggcattaaaa atttcggttc caccgttaag aactatggca gcaaggcctg  26340
```

```
gaacagcagc acaggccaga tgctgaggga taagttgaaa gagcaaaatt tccaacaaaa    26400
ggtggtagat ggcctggcct ctggcattag cggggtggtg gacctggcca accaggcagt    26460
gcaaaataag attaacagta agcttgatcc ccgccctccc gtagaggagc ctccaccggc    26520
cgtggagaca gtgtctccag aggggcgtgg cgaaaagcgt ccgcgcccg  acagggaaga    26580 aactctggtg acgcaaatag acgagcctcc ctcgtacgag gaggcactaa agcaaggcct    26640
gcccaccacc cgtcccatcg cgcccatggc taccggagtg ctgggccagc acacacccgt    26700
aacgctggac ctgcctcccc ccgccgacac ccagcagaaa cctgtgctgc caggcccgac    26760
cgccgttgtt gtaacccgtc ctagccgcgc gtccctgcgc cgcgccgcca gcggtccgcg    26820
atcgttgcgg cccgtagcca gtggcaactg gcaaagcaca ctgaacagca tcgtgggtct    26880
gggggtgcaa tccctgaagc gccgacgatg cttctgaata gctaacgtgt cgtatgtgtg    26940
tcatgtatgc gtccatgtcg ccgccagagg agctgctgag ccgccgcgcg cccgctttcc    27000
aagatggcta ccccttcgat gatgccgcag tggtcttaca tgcacatctc gggccaggac    27060
gcctcggagt acctgagccc cgggctggtg cagtttgccc gcgccaccga gacgtacttc    27120
agcctgaata caagtttag  aaaccccacg gtggcgccta cgcacgacgt gaccacagac    27180
cggtcccagc gtttgacgct gcggttcatc cctgtggacc gtgaggatac tgcgtactcg    27240
tacaaggcgc ggttcaccct agctgtgggt gataaccgtg tgctggacat ggcttccacg    27300
tactttgaca tccgcggcgt gctggacagg ggccctactt ttaagcccta ctctggcact    27360
gcctacaacg ccctggctcc caagggtgcc ccaaatcctt gcgaatggga tgaagctgct    27420
actgctcttg aaataaacct agaagaagag gacgatgaca acgaagacga agtagacgag    27480
caagctgagc agcaaaaaac tcacgtattt gggcaggcgc cttattctgg tataaatatt    27540 acaaggagg  gtattcaaat aggtgtcgaa ggtcaaacac ctaaatatgc cgataaaaca    27600
tttcaacctg aacctcaaat aggagaatct cagtggtacg aaactgaaat taatcatgca    27660
gctgggagag tccttaaaaa gactacccca atgaaaccat gttacggttc atatgcaaaa    27720
cccacaaatg aaaatggagg gcaaggcatt cttgtaaagc aacaaaatgg aaagctagaa    27780
agtcaagtgg aaatgcaatt tttctcaact actgaggcga ccgcaggcaa tggtgataac    27840
ttgactccta aagtggtatt gtacagtgaa gatgtagata tagaaacccc agacactcat    27900
atttcttaca tgcccactat taaggaaggt aactcacgag aactaatggg ccaacaatct    27960
atgcccaaca ggcctaatta cattgctttt agggacaatt ttattggtct aatgtattac    28020
aacagcacgg gtaatatggg tgttctggcg ggccaagcat cgcagttgaa tgctgttgta    28080
gatttgcaag acagaaacac agagctttca taccagcttt tgcttgattc cattggtgat    28140
agaaccaggt acttttctat gtggaatcag gctgttgaca gctatgatcc agatgttaga    28200
attattgaaa tcatggaac  tgaagatgaa cttccaaatt actgctttcc actgggaggt    28260
gtgattaata cagagactct taccaaggta aaacctaaaa caggtcagga aaatggatgg    28320 gaaaagatg  ctacagaatt ttcagataaa aatgaaataa gagttggaaa taattttgcc    28380
atggaaatca atctaaatgc caacctgtgg agaaatttcc tgtactccaa catagcgctg    28440
tatttgcccg acaagctaaa gtacagtcct tccaacgtaa aaattctga  taacccaaac    28500 acctacgact acatgaacaa gcgagtggtg gctcccgggt tagtggactg ctacattaac    28560
cttggagcac gctggtccct tgactatatg gacaacgtca acccatttaa ccaccaccgc    28620 aatgctggc  tgcgctaccg ctcaatgttg ctggcaatg  tcgctatgt  gcccttccac    28680 atccaggtgc ctcagaagtt ctttgccatt aaaaacctcc ttctcctgcc gggctcatac    28740
```

```
acctacgagt ggaacttcag gaaggatgtt aacatggttc tgcagagctc cctaggaaat    28800
gacctaaggg ttgacggagc cagcattaag tttgatagca tttgccttta cgccaccttc    28860
ttccccatgg cccacaacac cgcctccacg cttgaggcca tgcttagaaa cgacaccaac    28920
gaccagtcct ttaacgacta tctctccgcc gccaacatgc tctacccat acccgccaac     28980 gctaccaacg tgcccatatc catcccctcc cgcaactggg cggctttccg cggctgggcc    29040
ttcacgcgcc ttaagactaa ggaaaccca tcactgggct cgggctacga cccttattac      29100
acctactctg gctctatacc ctacctagat ggaaccttt acctcaacca cacctttaag      29160
aaggtggcca ttacctttga ctcttctgtc agctggcctg gcaatgaccg cctgcttacc    29220
cccaacgagt ttgaaattaa gcgctcagtt gacggggagg gttacaacgt tgcccagtgt    29280
aacatgacca aagactggtt cctggtacaa atgctagcta actacaacat ggctaccag     29340 ggcttctata tcccagagag ctacaaggac cgcatgtact ccttctttag aaacttccag    29400
cccatgagcc gtcaggtggt ggatgatact aaatacaagg actaccaaca ggtgggcatc    29460
ctacaccaac acaacaactc tggatttgtt ggctaccttg ccccaccat gcgcgaagga     29520 caggcctacc ctgctaactt ccctatccg cttataggca agaccgcagt tgacagcatt      29580
acccagaaaa agtttctttg cgatcgcacc ctttggcgca tcccattctc cagtaacttt    29640
atgtccatgg gcgcactcac agacctgggc caaaaccttc tctacgccaa ctccgcccac    29700
gcgctagaca tgacttttga ggtggatccc atggacgagc ccaccttct ttatgttttg      29760 tttgaagtct ttgacgtggt ccgtgtgcac cggccgcacc gcggcgtcat cgaaaccgtg    29820
tacctgcgca cgcccttctc ggccggcaac gccacaacat aaagaagcaa gcaacatcaa    29880
caacagctgc cgccatgggc tccagtgagc aggaactgaa agccattgtc aaagatcttg    29940
gttgtgggcc atatttttg ggcacctatg acaagcgctt ccaggctttt gtttctccac     30000
acaagctcgc ctgcgccata gtcaatacgg ccggtcgcga gactgggggc gtacactgga    30060
tggcctttgc ctggaacccg cactcaaaaa catgctacct ctttgagccc tttggctttt    30120
ctgaccagcg actcaagcag gtttaccagt ttgagtacga gtcactcctg cgccgtagcg    30180
ccattgcttc ttcccccgac cgctgtataa cgctggaaaa gtccacccaa agcgtacagg    30240
ggcccaactc ggccgcctgt ggactattct gctgcatgtt tctccacgcc tttgccaact    30300
ggccccaaac tccatggat cacaaccca ccatgaacct tattaccggg gtacccaact       30360
ccatgctcaa cagtccccag gtacagccca ccctgcgtcg caaccaggaa cagctctaca    30420
gcttcctgga gcgccactcg ccctacttcc gcagccacag tgcgcagatt aggagcgcca    30480 cttcttttg tcacttgaaa aacatgtaaa aataatgtac tagagacact ttcaataaag      30540
gcaaatgctt ttatttgtac actctcgggt gattatttac ccccacctt gccgtctgcg      30600 ccgtttaaaa atcaaagggg ttctgccgcg catcgctatg cgccactggc agggacacgt    30660
tgcgatactg gtgtttagtg ctccacttaa actcaggcac aaccatccgc ggcagctcgg    30720
tgaagttttc actccacagg ctgcgcacca tcaccaacgc gtttagcagg tcgggcgccg    30780
atatcttgaa gtcgcagttg gggcctccgc cctgcgcgcg cgagttgcga tacacagggt    30840
tgcagcactg gaacactatc agcgccgggt ggtgcacgct ggccagcacg ctcttgtcgg    30900
agatcagatc cgcgtccagg tcctccgcgt tgctcagggc gaacggagtc aactttggta    30960
gctgccttcc caaaagggc gcgtgccag gctttgagtt gcactcgcac cgtagtggca     31020
tcaaaaggtg accgtgcccg gtctgggcgt taggatacag cgcctgcata aaagccttga    31080
tctgcttaaa agccacctga gcctttgcgc cttcagagaa gaacatgccg caagacttgc    31140
```

```
cggaaaactg attggccgga caggccgcgt cgtgcacgca gcaccttgcg tcggtgttgg    31200
agatctgcac cacatttcgg ccccaccggt tcttcacgat cttggccttg ctagactgct    31260
ccttcagcgc gcgctgcccg ttttcgctcg tcacatccat ttcaatcacg tgctccttat    31320
ttatcataat gcttccgtgt agacacttaa gctcgccttc gatctcagcg cagcggtgca    31380
gccacaacgc gcagcccgtg ggctcgtgat gcttgtaggt cacctctgca aacgactgca    31440
ggtacgcctg caggaatcgc cccatcatcg tcacaaaggt cttgttgctg gtgaaggtca    31500
gctgcaaccc gcggtgctcc tcgttcagcc aggtcttgca tacggccgcc agagcttcca    31560
cttggtcagg cagtagtttg aagttcgcct ttagatcgtt atccacgtgg tacttgtcca    31620
tcagcgcgcg cgcagcctcc atgcccttct cccacgcaga cacgatcggc acactcagcg    31680
ggttcatcac cgtaatttca ctttccgctt cgctgggctc ttcctcttcc tcttgcgtcc    31740
gcataccacg cgccactggg tcgtcttcat tcagccgccg cactgtgcgc ttacctcctt    31800
tgccatgctt gattagcacc ggtgggttgc tgaaacccac catttgtagc gccacatctt    31860
ctctttcttc ctcgctgtcc acgattacct ctggtgatgg cgggcgctcg ggcttgggag    31920
aagggcgctt cttttcttc ttgggcgcaa tggccaaatc cgccgccgag gtcgatggcc    31980
gcgggctggg tgtgcgcggc accagcgcgt cttgtgatga gtcttcctcg tcctcggact    32040
cgatacgccg cctcatccgc ttttttgggg gcgcccgggg aggcggcggc gacggggacg    32100
gggacgacac gtcctccatg gttggggac gtcgcgccgc accgcgtccg cgctcggggg    32160
tggtttcgcg ctgctcctct tcccgactgg ccatttcctt ctcctatagg cagaaaaaga    32220
tcatggagtc agtcgagaag aaggacagcc taaccgcccc ctctgagttc gccaccaccg    32280
cctccaccga tgccgccaac gcgcctacca ccttccccgt cgaggcaccc ccgcttgagg    32340
aggaggaagt gattatcgag caggacccag gttttgtaag cgaagacgac gaggaccgct    32400
cagtaccaac agaggataaa aagcaagacc aggacaacgc agaggcaaac gaggaacaag    32460
tcgggcgggg ggacgaaagg catggcgact acctagatgt gggagacgac gtgctgttga    32520
agcatctgca gcgccagtgc gccattatct gcgacgcgtt gcaagagcgc agcgatgtgc    32580
ccctcgccat agcggatgtc agccttgcct acgaacgcca cctattctca ccgcgcgtac    32640
cccccaaacg ccaagaaaac ggcacatgcg agcccaaccc gcgcctcaac ttctaccccg    32700
tatttgccgt gccagaggtg cttgccacct atcacatctt tttccaaaac tgcaagatac    32760
ccctatcctg ccgtgccaac cgcagccgag cggacaagca gctggccttg cggcagggcg    32820
ctgtcatacc tgatatcgcc tcgctcaacg aagtgccaaa aatctttgag ggtcttggac    32880
gcgacgagaa gcgcgcggca aacgctctgc aacaggaaaa cagcgaaaat gaaagtcact    32940
ctggagtgtt ggtggaactc gagggtgaca acgcgcgcct agccgtacta aaacgcagca    33000
tcgaggtcac ccactttgcc tacccggcac ttaacctacc cccaaggtc atgagcacag    33060 tcatgagtga gctgatcgtg cgccgtgcgc agccctgga gagggatgca aatttgcaag    33120
aacaaacaga ggagggccta cccgcagttg gcgacgagca gctagcgcgc tggcttcaaa    33180
cgcgcgagcc tgccgacttg gaggagcgac gcaaactaat gatggccgca gtgctcgtta    33240
ccgtggagct tgagtgcatg cagcggttct ttgctgaccc ggagatgcag cgcaagctag    33300
aggaaacatt gcactacacc tttcgacagg gctacgtacg ccaggcctgc aagatctcca    33360
acgtggagct ctgcaacctg gtctcctacc ttggaatttt gcacgaaaac cgccttgggc    33420
aaaacgtgct tcattccacg ctcaagggcg aggcgcgccg cgactacgtc cgcgactgcg    33480
tttacttatt tctatgctac acctggcaga cggccatggg cgtttggcag cagtgcttgg    33540
```

-continued

```
aggagtgcaa cctcaaggag ctgcagaaac tgctaaagca aaacttgaag gacctatgga    33600
cggccttcaa cgagcgctcc gtggccgcgc acctggcgga catcattttc cccgaacgcc    33660
tgcttaaaac cctgcaacag ggtctgccag acttcaccag tcaaagcatg ttgcagaact    33720
ttaggaactt tatcctagag cgctcaggaa tcttgcccgc cacctgctgt gcacttccta    33780
gcgactttgt gcccattaag taccgcgaat gccctccgcc gctttggggc cactgctacc    33840
ttctgcagct agccaactac cttgcctacc actctgacat aatggaagac gtgagcggtg    33900
acggtctact ggagtgtcac tgtcgctgca acctatgcac cccgcaccgc tccctggttt    33960
gcaattcgca gctgcttaac gaaagtcaaa ttatcggtac ctttgagctg cagggtccct    34020
cgcctgacga aaagtccgcg gctccggggt tgaaactcac tccggggctg tggacgtcgg    34080
cttaccttcg caaatttgta cctgaggact accacgccca cgagattagg ttctacgaag    34140
accaatcccg cccgccaaat gcggagctta ccgcctgcgt cattacccag ggccacattc    34200
ttggccaatt gcaagccatc aacaaagccc gccaagagtt tctgctacga agggacggg    34260 gggtttactt ggaccccag tccggcgagg agctcaaccc aatcccccg ccgccgcagc    34320 cctatcagca gcagccgcgg gcccttgctt ccaggatgg cacccaaaaa gaagctgcag    34380
ctgccgccgc cacccacgga cgaggaggaa tactgggaca gtcaggcaga ggaggttttg    34440
gacgaggagg aggaggacat gatggaagac tgggagagcc tagacaggga agcttccgag    34500
gtcgaagagg tgtcagacga acaccgtca ccctcggtcg cattccctc gccggcgccc    34560 cagaaatcgg caaccggttc cagcatggct acaacctccg ctcctcaggc gccgccggca    34620
ctgcccgttc gccgacccaa ccgtagatgg gacaccactg gaaccagggc cggtaagtcc    34680
aagcagccgc cgccgttagc ccaagagcaa caacagcgcc aaggctaccg ctcatggcgc    34740
gggcacaaga acgccatagt tgcttgcttg caagactgtg ggggcaacat ctccttcgcc    34800
cgccgctttc ttctctacca tcacggcgtg gccttcccc gtaacatcct gcattactac    34860
cgtcatctct acagcccata ctgcaccggc ggcagcggca gcggcagcaa cagcagcggc    34920
cacacagaag caaaggcgac cggatagcaa gactctgaca aagcccaaga aatccacagc    34980
ggcggcagca gcaggaggag gagcgctgcg tctggcgccc aacgaacccg tatcgacccg    35040
cgagcttaga aacaggattt ttcccactct gtatgctata tttcaacaga gcagggggca    35100
agaacaagag ctgaaaataa aaaacaggtc tctgcgatcc ctcacccgca gctgcctgta    35160
tcacaaaagc gaagatcagc ttcggcgcac gctggaagac gcggaggctc tcttcagtaa    35220
atactgcgcg ctgactctta aggactagtt tcgcgccctt tctcaaattt aagcgcgaaa    35280
actacgtcat ctccagcggc cacaccggc gccagcacct gtcgtcagcg ccattatgag    35340
caaggaaatt cccacgccct acatgtggag ttaccagcca caaatgggac ttgcggctgg    35400
agctgcccaa gactactcaa cccgaataaa ctacatgagc gcgggacccc acatgatatc    35460
ccgggtcaac ggaatccgcg cccaccgaaa ccgaattctc ttggaacagg cggctattac    35520
caccacacct cgtaataacc ttaatccccg tagttggccc gctgccctgg tgtaccagga    35580
aagtcccgct cccaccactg tggtacttcc cagagacgcc caggccgaag ttcagatgac    35640
taactcaggg gcgcagcttg cgggcggctt tcgtcacagg gtgcggtcgc ccgggcaggg    35700
tataactcac ctgacaatca gagggcgagg tattcagctc aacgacgagt cggtgagctc    35760
ctcgcttggt ctccgtccgg acgggacatt tcagatcggc ggcgccggcc gtccttcatt    35820
cacgcctcgt caggcaatcc taactctgca gacctcgtcc tctgagccgc gctctggagg    35880
cattggaact ctgcaattta ttgaggagtt tgtgccatcg gtctacttta acccttctc    35940
```

```
gggacctccc ggccactatc cggatcaatt tattcctaac tttgacgcgg taaaggactc    36000
ggcggacggc tacgactgaa tgttaagtgg agaggcagag caactgcgcc tgaaacacct    36060
ggtccactgt cgccgccaca agtgctttgc ccgcgactcc ggtgagtttt gctactttga    36120
attgcccgag gatcatatcg agggcccggc gcacggcgtc cggcttaccg cccagggaga    36180
gcttgcccgt agcctgattc gggagtttac ccagcgcccc ctgctagttg agcgggacag    36240
gggaccctgt gttctcactg tgatttgcaa ctgtcctaac cttggattac atcaagatcc    36300
tctagttata actagagtac ccggggatct tattccctt  aactaataaa aaaaaataat    36360
aaagcatcac ttacttaaaa tcagttagca aatttctgtc cagtttattc agcagcacct    36420
ccttgccctc ctcccagctc tggtattgca gcttcctcct ggctgcaaac tttctccaca    36480
atctaaatgg aatgtcagtt tcctcctgtt cctgtccatc cgcacccact atcttcatgt    36540
tgttgcagat gaagcgcgca agaccgtctg aagatacctt caaccccgtg tatccatatg    36600
acacggaaac cggtcctcca actgtgcctt ttcttactcc tccctttgta tcccccaatg    36660
ggtttcaaga gagtcccct  ggggtactct ctttgcgcct atccgaacct ctagttacct    36720
ccaatggcat gcttgcgctc aaaatgggca acggcctctc tctggacgag gccggcaacc    36780
ttacctccca aaatgtaacc actgtgagcc cacctctcaa aaaaaccaag tcaaacataa    36840
acctggaaat atctgcaccc ctcacagtta cctcagaagc cctaactgtg gctgccgccg    36900
cacctctaat ggtcgcgggc aacacactca ccatgcaatc acaggccccg ctaaccgtgc    36960
acgactccaa acttagcatt gccacccaag gaccoctcac agtgtcagaa ggaaagctag    37020
ccctgcaaac atcaggcccc ctcaccacca ccgatagcag tacccttact atcactgcct    37080 cacccctct  aactactgcc actggtagct tgggcattga cttgaaagag cccatttata    37140
cacaaaatgg aaaactagga ctaaagtacg gggctccttt gcatgtaaca gacgacctaa    37200
acactttgac cgtagcaact ggtccaggtg tgactattaa taatacttcc ttgcaaacta    37260
aagttactgg agccttgggt tttgattcac aaggcaatat gcaacttaat gtagcaggag    37320
gactaaggat tgattctcaa aacagacgcc ttatacttga tgttagttat ccgtttgatg    37380
ctcaaaacca actaaatcta agactaggac agggccctct ttttataaac tcagcccaca    37440
acttggatat taactacaac aaaggccttt acttgtttac agcttcaaac aattccaaaa    37500
agcttgaggt taacctaagc actgccaagg ggttgatgtt tgacgctaca gccatagcca    37560
ttaatgcagg agatgggctt gaatttggtt cacctaatgc accaaacaca aatcccctca    37620
aaacaaaaat tggccatggc ctagaatttg attcaaacaa ggctatggtt cctaaactag    37680
gaactggcct tagttttgac agcacaggtg ccattacagt aggaaacaaa aataatgata    37740
agctaacttt gtggaccaca ccagctccat ctcctaactg tagactaaat gcagagaaag    37800
atgctaaact cactttggtc ttaacaaaat gtggcagtca aatacttgct acagtttcag    37860
ttttggctgt taaaggcagt ttggctccaa tatctggaac agttcaaagt gctcatctta    37920
ttataagatt tgacgaaaat ggagtgctac taaacaattc cttcctggac ccagaatatt    37980
ggaactttag aaatggagat cttactgaag gcacagccta tacaaacgct gttggattta    38040
tgcctaacct atcagcttat ccaaaatctc acggtaaaac tgccaaaagt aacattgtca    38100
gtcaagttta cttaaacgga gacaaaacta aacctgtaac actaaccatt acactaaacg    38160
gtacacagga aacaggagac acaactccaa gtgcatactc tatgtcattt tcatgggact    38220
ggtctggcca caactacatt aatgaaatat ttgccacatc tcttacact  ttttcataca    38280 ttgcccaaga ataaagaatc gtttgtgtta tgtttcaacg tgtttatttt tcaattgcag    38340
```

```
aaaatttcaa gtcattttc attcagtagt atagccccac caccacatag cttatacaga    38400
tcaccgtacc ttaatcaaac                                                38420

<210> SEQ ID NO 2
<211> LENGTH: 12741
<212> TYPE: DNA
<213> ORGANISM: Artificial Sequence
<220> FEATURE:
<223> OTHER INFORMATION: Synthetic polynucleotide

<400> SEQUENCE: 2
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa agacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgatt    1800
gggcccgaga tctcgcgcgc gaggcctgcc atgggcatgc ctgcaggtcg atgcgtggcc    1860
ggcctaggat ccatatggta ccggtaaatg gcccgcctgg ctgaccgccc aacgacccc     1920 gcccattgac gtcaataatg acgtatgttc ccatagtaac gccaataggg actttccatt    1980
```

```
gacgtcaatg ggtggagtat ttacggtaaa ctgcccactt ggcagtacat caagtgtatc    2040
atatgccaag tacgcccct attgacgtca atgacggtaa atggcccgcc tggcattatg     2100
cccagtacat gaccttatgg gactttccta cttggcagta catctagtat tagtcatcgc    2160
tattaccatg gtgatgcggt tttggcagta catcaatggg cgtggatagc ggtttgactc    2220
acggggattt ccaagtctcc accccattga cgtcaatggg agtttgtttt ggcaccaaaa    2280
tcaacgggac tttccaaaat gtcgtaacaa ctccgcccca ttgacgcaaa tgggcggtag    2340
gcgtgtacgg tgggaggtct atataagcag agctcgttta gtgaaccgtc agatcgcctg    2400
gagacgccat ccacgctgtt ttgacctcca tagaagacac cgggaccgat ccagcctccg    2460
cggccgggaa cggtgcattg gaacgcggat tccccgtgcc aagagtgacg taagtaccgc    2520
ctatagactc tataggcaca ccctttggc tcttatgcat gaattaatac gactcactat     2580
agggagacag actgttcctt tcctgggtct tttctgcagg ctagccccac catgccgcgc    2640 gctcccccgct gccgagccgt gcgctccctg ctgcgcagcc actaccgcga ggtgctgccg    2700
ctggccacgt tcgtgcggcg cctggggccc cagggctggg gctggtgca gcgcggggac     2760 ccggcggctt tccgcgcgct ggtggcccag tgcctggtgt gcgtgccctg ggacgcacgg    2820
ccgccccccg ccgcccctc cttccgccag gtgtcctgcc tgaaggagct ggtggcccga     2880
gtgctgcaga ggctgtgcga gcgcggcgcg aagaacgtgc tggccttcgg cttcgcgctg    2940
ctggacgggg cccgcggggg cccccccgag gccttcacca ccagcgtgcg cagctacctg    3000
cccaacacgg tgaccgacgc actgcggggg agcggggcgt gggggctgct gttgcgccgc    3060
gtgggcgacg acgtgctggt tcacctgctg gcacgctgcg cgctctttgt gctggtggct    3120
cccagctgcg cctaccaggt gtgcgggccg ccgctgtacc agctcggcgc tgccactcag    3180
gcccggcccc cgccacacgc tagtggaccc cgaaggcgtc tgggatgcga acgggcctgg    3240
aaccatagcg tcagggaggc cggggtcccc ctgggcctgc cagccccggg tgcgaggagg    3300 cgcggggca gtgccagccg aagtctgccg ttgcccaaga ggcccaggcg tggcgctgcc     3360
cctgagccgg agcggacgcc cgttgggcag gggtcctggg cccacccggg caggacgcgt    3420
ggaccgagtg accgtggttt ctgtgtggtg tcacctgcca gacccgccga agaagccacc    3480
tctttggagg gtgcgctctc tggcacgcgc cactcccacc catccgtggg ccgccagcac    3540
cacgcgggcc cccatccac atcgcggcca ccagtccct gggacacgcc ttgtcccccg      3600
gtgtacgccg agaccaagca cttcctctac tcctcaggcg acaaggagca gctgcggccc    3660
tccttcctac tcagctctct gaggcccagc ctgactggcg ctcggaggct cgtggagacc    3720
atctttctgg gttccaggcc ctggatgcca gggactcccc gcaggttgcc ccgcctgccc    3780
cagcgctact ggcaaatgcg gcccctgttt ctggagctgc ttgggaacca cgcgcagtgc    3840
ccctacgggg tgctcctcaa gacgcactgc ccgctgcgag ctgcggtcac cccagcagcc    3900
ggtgtctgtg cccgggagaa gccccagggc tctgtggcgg cccccgagga ggaggacaca    3960 gaccccgtc gcctggtgca gctgctccgc cagcacagca gccctggca ggtgtacggc      4020 ttcgtgcggg cctgcctgcg ccggctggtg cccccaggcc tctgggctc caggcacaac    4080 gaacgccgct tcctcaggaa caccaagaag ttcatctccc tggggaagca tgccaagctc    4140
tcgctgcagg agctgacgtg gaagatgagc gtgcggggct gcgcttggct gcgcaggagc    4200
caaggggttg gctgtgttcc ggccgcagag caccgtctgc gtgaggagat cctggccaag    4260
ttcctgcact ggctgatgag tgtgtacgtc gtcgagctgc tcaggtcttt cttttatgtc    4320
acggagacca cgtttcaaaa gaacaggctc tttttctacc ggaagagtgt ctggagcaag    4380
```

```
-continued ttgcaaagca ttggaatcag acagcacttg aagagggtgc agctgcggga gctgtcggaa    4440
gcagaggtca ggcagcatcg ggaagccagg cccgccctgc tgacgtccag actccgcttc    4500
atccccaagc ctgacgggct gcggccgatt gtgaacatgg actacgtcgt gggagccaga    4560
acgttccgca gagaaaagag ggccgagcgt ctcacctcca gggtgaaggc actgttcagc    4620
gtgctcaact acgagcgggc gcggcgcccc ggcctcctgg gcgcctctgt gctgggcctg    4680
gacgatatcc acagggcctg gcgcaccttc gtgctgcgtg tgcgggccca ggacccgccg    4740
cctgagctgt actttgtcaa ggtggatgtg acgggcgcgt acgacaccat ccccaggac    4800 aggctcacgg aggtcatcgc cagcatcatc aaaccccaga acacgtactg cgtgcgtcgg    4860
tatgccgtgg tccagaaggc cgcccatggg cacgtccgca aggccttcaa gagccacgtc    4920
tctaccttga cagacctcca gccgtacatg cgacagttcg tggctcacct gcaggagacc    4980
agcccgctga gggatgccgt cgtcatcgag cagagctcct ccctgaatga ggccagcagt    5040
ggcctcttcg acgtcttcct acgcttcatg tgccaccacg ccgtgcgcat caggggcaag    5100
tcctacgtcc agtgccaggg gatcccgcag ggctccatcc tctccacgct gctctgcagc    5160
ctgtgctacg gcgacatgga gaacaagctg tttgcgggga ttcggcggga cgggctgctc    5220
ctgcgtttgg tggatgattt cttgttggtg acacctcacc tcacccacgc gaaaaccttc    5280
ctcaggaccc tggtccgagg tgtccctgag tatggctgcg tggtgaactt gcggaagaca    5340
gtggtgaact ccctgtagag agacgaggcc ctgggtggca cggcttttgt tcagatgccg    5400
gcccacggcc tattcccctg gtgcggcctg ctgctggata cccggaccct ggaggtgcag    5460
agcgactact ccagctatgc ccggacctcc atcagagcca gtctcacctt caaccgcggc    5520
ttcaaggctg ggaggaacat gcgtcgcaaa ctctttgggg tcttgcggct gaagtgtcac    5580
agcctgtttc tggatttgca ggtgaacagc ctccagacgg tgtgcaccaa catctacaag    5640
atcctcctgc tgcaggcgta caggtttcac gcatgtgtgc tgcagctccc atttcatcag    5700
caagtttgga agaaccccac attttttcctg cgcgtcatct ctgacacggc ctccctctgc    5760
tactccatcc tgaaagccaa gaacgcaggg atgtcgctgg gggccaaggg cgccgccggc    5820
cctctgccct ccgaggccgt gcagtggctg tgccaccaag cattcctgct caagctgact    5880
cgacaccgtg tcacctacgt gccactcctg gggtcactca ggacagccca gacgcagctg    5940
agtcggaagc tcccggggac gacgctgact gccctggagg ccgcagccaa cccggcactg    6000
ccctcagact tcaagaccat cctggactga gtcgaaactc gaggatccgg ctgtggaatg    6060
tgtgtcagtt agggtgtgga aagtccccag gctcccagc aggcagaagt atgcaaagca    6120
tgcatctcaa ttagtcagca accaggtgtg gaaagtcccc aggctcccca gcaggcagaa    6180
gtatgcaaag catgcatctc aattagtcag caaccatagt cccgcccta actccgccca    6240 tcccgcccct aactccgccc agttccgccc attctccgcc ccatggctga ctaatttttt    6300
ttatttatgc agaggccgag gccgcctcgg cctctgagct attccagaag tagtgaggag    6360
gcttttttgg aggcctcgg ccgccacgac cgtgccgcc accatcccct gacccacgcc    6420
cctgacccct cacaaggaga cgaccttcca tgaccgagta caagcccacg gtgcgcctcg    6480
ccacccgcga cgacgtcccc cgggccgtac gcacccgcc cgccgcgttc gccgactacc    6540
ctgcaacacg ccatacagtg accctgacc gccacatcga gcgggtcacc gagctgcaag    6600
aactcttcct cacgcgcgtc gggctcgaca tcggcaaggt gtgggtcgcg gacgacggcg    6660
ccgcggtggc ggtctggacc acgccggaga gcgtcgaagc gggggcggtg ttcgccgaga    6720
tcggcccgcg catggccgag ttgagcggtt cccggctggc cgcgcagcaa cagatggaag    6780
```

-continued

```
gcctcctggc gccgcaccgg cccaaggagc ccgcgtggtt cctggccacc gtcggcgtct    6840
cgcccgacca ccagggcaag ggtctgggca gcgccgtcgt gctccccgga gtggaggcgg    6900
ccgagcgcgc cggggtgccc gccttcctgg agacctccgc gccccgcaac ctccccttct    6960
acgagcggct cggcttcacc gtcaccgccg acgtcgaggt gcccgaagga ccgcgcacct    7020
ggtgcatgac ccgcaagccc ggtgcctgac gcccgcccca cgacccgcag cgcccgaccg    7080
aaaggagcgc acgaccccat gcatcgataa aataaaagat tttatttagt ctccagaaaa    7140
agggggaat gaaagacccc acctgtaggt ttggcaagct aggcctatta atattccgga    7200
gtatacgtag ccggctaacg ttaacaaccg gtacgatgca ttagttatta atagtaatca    7260
attacgggt cattagttca tagcccatat atggagttcc gcgttacata acttacggta    7320
aatggcccgc ctggctgacc gcccaacgac ccccgcccat tgacgtcaat aatgacgtat    7380
gttcccatag taacgccaat agggactttc cattgacgtc aatgggtgga gtatttacgg    7440
taaactgccc acttggcagt acatcaagtg tatcatatgc caagtacgcc ccctattgac    7500
gtcaatgacg gtaaatggcc cgcctggcat tatgcccagt acatgacctt atgggacttt    7560
cctacttggc agtacatcta cgtattagtc atcgctatta ccatggtgat gcggttttgg    7620
cagtacatca atgggcgtgg atagcggttt gactcacggg gatttccaag tctccacccc    7680
attgacgtca atgggagttt gttttggcac caaaatcaac gggactttcc aaaatgtcgt    7740
aacaactccg ccccattgac gcaaatgggc ggtaggcgtg tacggtggga ggtctatata    7800
agcagagctg gtttagtgaa ccgtcagatc cgctagcgct accggactca gatctcgagc    7860
tcaagcttcg aattctgcag tcgacccacc atggctcttt caaacaagtt tatcggagat    7920
gacatgaaaa tgacctacca tatggatggc tgtgtcaatg gcattactt taccgtcaaa    7980
ggtgaaggca gcggaagcc atacgaaggg acgcagacct cgacttttaa agtcaccatg    8040
gccaacggtg ggccccttgc attctccttt gacatactat ctacagtgtt catgtatgga    8100
aatcgatgct ttactgcgta tcctaccagt atgcccgact atttcaaaca gcatttcct    8160
gacggaatgt catatgaaag gacttttacc tatgaagatg gaggagttgc tacagccagt    8220
tgggaaataa gccttaaagg caactgcttt gagcacaaat ccacgtttca tggagtgaac    8280
tttcctgctg atggacctgt gatggcgaag atgacaactg gttgggaccc atcttttgag    8340
aaaatgactg tctgcgatgg aatattgaag ggtgatgtca ccgcgttcct catgctgcaa    8400
ggaggtggca attacagatg ccaattccac acttcttaca agacaaaaaa accggtgacg    8460
atgccaccaa accatgcggt ggaacatcgc attgcgagga ccgaccttga caaaggtggc    8520
aacagtgttc agctgacgga gcacgctgtt gcacatataa cctctgttgt ccctttctag    8580
cggccgcgat aatcaacctc tggattacaa aatttgtgaa agattgactg gtattcttaa    8640
ctatgttgct ccttttacgc tatgtggata cgctgcttta atgcctttgt atcatgctat    8700
tgcttcccgt atggctttca ttttctcctc cttgtataaa tcctggttgc tgtctcttta    8760
tgaggagttg tggcccgttg tcaggcaacg tggcgtggtg tgcactgtgt ttgctgacgc    8820
aaccccact ggttggggca ttgccaccac ctgtcagctc ctttccggga ctttcgcttt    8880
cccctccct attgccacgg cggaactcat cgccgcctgc cttgcccgct gctgacagg    8940
ggctcggctg ttgggcactg acaattccgt ggtgttgtcg gggaagctga cgtcctttcc    9000
atggctgctc gcctgtgttg ccacctggat tctgcgcggg acgtccttct gctacgtccc    9060
ttcggccctc aatccagcgg accttccttc ccgcggcctg ctgccggctc tgcggcctct    9120
tccgcgtctt cgccttcgcc ctcagacgag tcggatctcc cttgggccg cctccccgca    9180
```

```
tcggacgcgt ggtacctta agaccaatga cttacaaggc agctgtagat cttagccact    9240
ttttaaaaga aaggggggga ctggaagggc taattcactc ccaacgaaga caagatctgc    9300
tttttgcttg tactgggtct ctctggttag accagatctg agcctgggag ctctctggct    9360
aactagggaa cccactgctt aagcctcaat aaagcttgcc ttgagtgctt caagtagtgt    9420
gtgcccgtct gttgtgtgac tctggtaact agagatccct cagaccctt tagtcagtgt     9480
ggaaaatctc tagcagtagt agttcatgtc atcttattat tcagtattta aacttgcaa     9540
agaaatgaat atcagagagt gagaggaact tgtttattgc agcttataat ggttacaaat    9600
aaagcaatag catcacaaat tcacaaata aagcattttt ttcactgcat tctagttgtg     9660
gtttgtccaa actcatcaat gtatcttatc atgtctggct ctagctatcc cgcccctaac    9720
tccgcccatc ccgcccctaa ctccgcccag ttccgcccat tctccgcccc atggctgact    9780
aatttttttt atttatgcag aggccgaggc cgcctcggcc tctgagctat tccagaagta    9840
gtgaggaggc ttttttggag gcctaggac gtacccaatt cgccctatag tgagtcgtat    9900
tacgcgcgct cactggccgt cgttttacaa cgtcgtgact gggaaaaccc tggcgttacc    9960
caacttaatc gccttgcagc acatccccct ttcgccagct ggcgtaatag cgaagaggcc    10020
cgcaccgatc gcccttccca acagttgcgc agcctgaatg gcgaatggga cgcgccctgt    10080
agcggcgcat taagcgcggc gggtgtggtg gttacgcgca gcgtgaccgc tacacttgcc    10140
agcgccctag cgcccgctcc tttcgctttc ttcccttcct ttctcgccac gttcgccggc    10200
tttccccgtc aagctctaaa tcggggggctc cctttagggt tccgatttag tgctttacgg    10260
cacctcgacc ccaaaaaact tgattagggt gatggttcac gtagtgggcc atcgccctga    10320
tagacggttt ttcgcccttt gacgttggag tccacgttct ttaatagtgg actcttgttc    10380
caaactggaa caacactcaa ccctatctcg gtctattctt ttgatttata agggattttg    10440
ccgatttcgg cctattggtt aaaaaatgag ctgatttaac aaaaatttaa cgcgaatttt    10500
aacaaaatat taacgcttac aatttaggtg cacttttcg gggaaatgtg cgcggaaccc    10560
ctatttgttt atttttctaa atacattcaa atatgtatcc gctcatgaga caataaccct    10620
gataaatgct tcaataatat tgaaaaagga agagtatgag tattcaacat ttccgtgtcg    10680
cccttattcc cttttttgcg gcattttgcc ttcctgtttt tgctcaccca gaaacgctgg    10740
tgaaagtaaa agatgctgaa gatcagttgg gtgcacgagt gggttacatc gaactggatc    10800
tcaacagcgg taagatcctt gagagttttc gccccgaaga acgttttcca atgatgagca    10860
cttttaaagt tctgctatgt ggcgcggtat tatcccgtat tgacgccggg caagagcaac    10920
tcggtcgccg catacactat tctcagaatg acttggttga gtactcacca gtcacagaaa    10980
agcatcttac ggatggcatg acagtaagag aattatgcag tgctgccata accatgagtg    11040
ataacactgc ggccaactta cttctgacaa cgatcggagg accgaaggag ctaaccgctt    11100
ttttgcacaa catggggggat catgtaactc gccttgatcg ttgggaaccg gagctgaatg    11160
aagccatacc aaacgacgag cgtgacacca cgatgcctgt agcaatggca acaacgttgc    11220
gcaaactatt aactggcgaa ctacttactc tagcttcccg gcaacaatta atagactgga    11280
tggaggcgga taaagttgca ggaccacttc tgcgctcggc ccttccggct ggctggttta    11340
ttgctgataa atctggagcc ggtgagcgtg ggtctcgcgg tatcattgca gcactggggc    11400
cagatggtaa gccctcccgt atcgtagtta tctacacgac ggggagtcag gcaactatgg    11460
atgaacgaaa tagacagatc gctgagatag gtgcctcact gattaagcat tggtaactgt    11520
cagaccaagt ttactcatat atactttaga ttgatttaaa acttcatttt taatttaaaa    11580
```

```
ggatctaggt gaagatcctt tttgataatc tcatgaccaa atcccttaa cgtgagtttt    11640 cgttccactg agcgtcagac cccgtagaaa agatcaaagg atcttcttga gatcctttt    11700 ttctgcgcgt aatctgctgc ttgcaaacaa aaaaccacc gctaccagcg gtggtttgtt    11760
tgccggatca agagctacca actcttttc cgaaggtaac tggcttcagc agagcgcaga    11820
taccaaatac tgttcttcta gtgtagccgt agttaggcca ccacttcaag aactctgtag    11880
caccgcctac atacctcgct ctgctaatcc tgttaccagt ggctgctgcc agtggcgata    11940
agtcgtgtct taccgggttg gactcaagac gatagttacc ggataaggcg cagcggtcgg    12000
gctgaacggg gggttcgtgc acacagccca gcttggagcg aacgacctac accgaactga    12060
gatacctaca gcgtgagcta tgagaaagcg ccacgcttcc cgaagggaga aaggcggaca    12120
ggtatccggt aagcggcagg gtcggaacag gagagcgcac gagggagctt ccaggggggaa    12180 acgcctggta tctttatagt cctgtcgggt ttcgccacct ctgacttgag cgtcgatttt    12240
tgtgatgctc gtcagggggg cggagcctat ggaaaaacgc cagcaacgcg gcctttttac    12300
ggttcctggc cttttgctgg ccttttgctc acatgttctt tcctgcgtta tcccctgatt    12360
ctgtggataa ccgtattacc gcctttgagt gagctgatac cgctcgccgc agccgaacga    12420
ccgagcgcag cgagtcagtg agcgaggaag cggaagagcg cccaatacgc aaaccgcctc    12480
tccccgcgcg ttggccgatt cattaatgca gctggcacga caggtttccc gactggaaag    12540
cgggcagtga gcgcaacgca attaatgtga gttagctcac tcattaggca ccccaggctt    12600
tacactttat gcttccggct cgtatgttgt gtggaattgt gagcggataa caatttcaca    12660
caggaaacag ctatgaccat gattacgcca agcgcgcaat taaccctcac taaagggaac    12720
aaaagctgga gctgcaagct t                                              12741
```

<210> SEQ ID NO 3
<211> LENGTH: 11626
<212> TYPE: DNA
<213> ORGANISM: Artificial Sequence
<220> FEATURE:
<223> OTHER INFORMATION: Synthetic polynucleotide

<400> SEQUENCE: 3

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaga    600 attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
```

```
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgata   1800
ctagtaattt ttctgcagaa aacgtacccg gggatcctct aggatcccac cgaaaggttg   1860
ctccttaaca caggctaagg accagcttct ttgggagaga acagacgcag gggcgggagg   1920
gaaaaaggga gaggcagacg tcacttcccc ttggcggctc tggcagcaga ttggtcggtt   1980
gagtggcaga aaggcagacg gggactgggc aaggcactgt cggtgacatc acggacaggg   2040
cgacttctat gtagatgagg cagcgcagag gctgctgctt cgccacttgc tgcttcgcca   2100
cgaaggagtt cccgtgccct gggagcgggt tcaggaccgc ggatcggaag tgagaatccc   2160
agctgtgtgt cagggctgga aagggctcgg gagtgcgcgg ggcaagtgac cgtgtgtgta   2220
aagagtgagg cgtatgaggc tgtgtcgggg cagagcccga agatccgggt tgcggagggt   2280
gggcctggga ggggtggtgg ccatttttttg tctaacccta actgagaagg gcgtaggcgc   2340
cgtgcttttg ctccccgcgc gctgtttttc tcgctgactt tcagcgggcg aaaagcctc   2400 ggcctgccgc cttccaccgt tcattctaga gcaaacaaaa aatgtcagct gctggcccgt   2460
tcgcccctcc cggggacctg cggcgggtcg cctgcccagc ccccgaaccc cgcctggagg   2520
ccgcggtcgg cccggggctt ctccggaggc acccactgcc accgcgaaga gttgggctct   2580
gtcagccgcg ggtctctcgg gggcgagggc gaggttcagg cctttcaggc cgcaggaaga   2640
ggaacggagc gagtccccgc gcgcggcgcg attccctgag ctgtgggacg tgcacccagg   2700
actcggctca cacatgcagt tcgctttcct gttggtgggg ggaacgccga tcgtgcgcat   2760
ccgtcacccc tcgccggcaa tgggggcttg tgaaccccca aacctgactg actgggccag   2820
tgtgctgcaa attggcagga gacgtgaagg cactccaaa gtcgactttc tggagtttca   2880
aaaacagacc gtacatgtcc gcggtcgcga cgtacctacc gggtagggga ggcgcttttc   2940
ccaaggcagt ctggagcatg cgctttagca gccccgctgg gcacttggcg ctacacaagt   3000
ggcctctggc ctcgcacaca ttccacatcc accggtaggc gccaaccggc tccgttcttt   3060
ggtggcccct tcgcgccacc ttctactcct cccctagtca ggaagttccc ccccgccccg   3120
cagctcgcgt cgtgcaggac gtgacaaatg gaagtagcac gtctcactag tctcgtgcag   3180
atggacagca ccgctgagca atggaagcgg gtaggccttt ggggcagcgg ccaatagcag   3240
ctttgctcct tcgctttctg ggctcagagg ctgggaaggg gtgggtccgg gggcgggctc   3300
```

```
aggggcgggc tcaggggcgg ggcgggcgcc cgaagtcctc cggaggcccg gcattctgca    3360
cgcttcaaaa gcgcacgtct gccgcgctgt tctcctcttc ctcatctccg ggcctttcga    3420
ctctagacac gtgttgacaa ttaatcatcg gcatagtata tcggcatagt ataatacgac    3480
aaggtgagga actaaaccat ggccaagcct ttgtctcaag aagaatccac cctcattgaa    3540
agagcaacgg ctacaatcaa cagcatcccc atctctgaag actacagcgt cgccagcgca    3600
gctctctcta cgcacggccg catcttcact ggtgtcaatg tatatcattt tactggggga    3660
ccttgtgcag aactcgtggt gctgggcact gctgctgctg cggcagctgg caacctgact    3720
tgtatcgtcg cgatcggaaa tgagaacagg ggcatcttga cccctgcgg acggtgccga     3780 caggtgcttc tcgatctgca tcctgggatc aaagccatag tgaaggacag tgatggacag    3840
ccgacggcag ttgggattcg tgaattgctg ccctctggtt atgtgtggga gggctaagca    3900
caattcgagc tcggtacgcg tatcgatggc gccagctgca ggcggccgcc atatgcatcc    3960
taggcctatt aatattccgg agtatacgta gccggctaac gttaacaacc ggtacgatgc    4020
attagttatt aatagtaatc aattacgggg tcattagttc atagcccata tatggagttc    4080
cgcgttacat aacttacggt aaatggcccg cctggctgac cgcccaacga cccccgccca    4140
ttgacgtcaa taatgacgta tgttcccata gtaacgccaa tagggacttt ccattgacgt    4200
caatgggtgg agtatttacg gtaaactgcc cacttggcag tacatcaagt gtatcatatg    4260
ccaagtacgc cccctattga cgtcaatgac ggtaaatggc ccgcctggca ttatgcccag    4320
tacatgacct tatgggactt tcctacttgg cagtacatct acgtattagt catcgctatt    4380
accatggtga tgcggttttg gcagtacatc aatgggcgtg gatagcggtt tgactcacgg    4440
ggatttccaa gtctccaccc cattgacgtc aatgggagtt tgttttggca ccaaaatcaa    4500
cgggactttc caaaatgtcg taacaactcc gccccattga cgcaaatggg cggtaggcgt    4560
gtacggtggg aggtctatat aagcagagct ggtttagtga accgtcagat ccgctagccc    4620
caccatgccg cgcgctcccc gctgccgagc cgtgcgctcc ctgctgcgca gccactaccg    4680
cgaggtgctg ccgctggcca cgttcgtgcg gcgcctgggg cccagggct ggcggctggt      4740 gcagcgcggg gacccggcgg ctttccgcgc gctggtggcc cagtgcctgg tgtgcgtgcc    4800
ctgggacgca cggccgcccc ccgccgcccc ctccttccgc caggtgtcct gcctgaagga    4860
gctggtggcc cgagtgctgc agaggctgtg cgagcgcggc gcgaagaacg tgctggcctt    4920
cggcttcgcg ctgctggacg ggcccgcgg gggccccccc gaggccttca ccaccagcgt    4980
gcgcagctac ctgcccaaca cggtgaccga cgcactgcgg gggagcgggg cgtgggggct    5040
gctgttgcgc cgcgtgggcg acgacgtgct ggttcacctg ctggcacgct gcgcgctctt    5100
tgtgctggtg gctcccagct gcgcctacca ggtgtgcggg ccgccgctgt accagctcgg    5160
cgctgccact caggcccggc ccccgccaca cgctagtgga ccccgaaggc gtctgggatg    5220
cgaacgggcc tggaaccata gcgtcaggga ggcggggtc cccctgggcc tgccagcccc     5280
gggtgcgagg aggcgcgggg gcagtgccag ccgaagtctg ccgttcccca agaggcccag    5340
gcgtggcgct gccctgagc cggagcggac gcccgttggg cagggtcct gggcccaccc      5400 gggcaggacg cgtggaccga gtgaccgtgg tttctgtgtg gtgtcacctg ccagacccgc    5460
cgaagaagcc acctctttgg agggtgcgct ctctggcacg cgccactccc acccatccgt    5520
gggccgccag caccacgcgg gcccccatc cacatcgcgg ccaccacgtc ctgggacac      5580 gccttgtccc ccggtgtacg ccgagaccaa gcacttcctc tactcctcag gcgacaagga    5640
gcagctgcgg ccctccttcc tactcagctc tctgaggccc agcctgactg gcgctcggag    5700
```

```
gctcgtggag accatctttc tgggttccag gccctggatg ccagggactc cccgcaggtt    5760
gccccgcctg cccagcgct actggcaaat gcggcccctg tttctggagc tgcttgggaa     5820
ccacgcgcag tgccctacg gggtgctcct caagacgcac tgcccgctgc gagctgcggt     5880
caccccagca gccggtgtct gtgcccggga aagccccag ggctctgtgg cggccccga      5940
ggaggaggac acagaccccc gtcgcctggt gcagctgctc cgccagcaca gcagcccctg   6000
gcaggtgtac ggcttcgtgc gggcctgcct gcgccggctg gtgccccag gcctctgggg    6060
ctccaggcac aacgaacgcc gcttcctcag gaacaccaag aagttcatct ccctggggaa   6120
gcatgccaag ctctcgctgc aggagctgac gtggaagatg agcgtgcggg gctgcgcttg  6180
gctgcgcagg agcccagggg ttggctgtgt tccggccgca gagcaccgtc tgcgtgagga   6240
gatcctggcc aagttcctgc actggctgat gagtgtgtac gtcgtcgagc tgctcaggtc   6300
tttcttttat gtcacggaga ccacgtttca aaagaacagg ctcttttct accggaagag    6360
tgtctggagc aagttgcaaa gcattggaat cagacagcac ttgaagaggg tgcagctgcg  6420
ggagctgtcg gaagcagagg tcaggcagca tcggaagcc aggcccgccc tgctgacgtc   6480
cagactccgc ttcatcccca agcctgacgg gctgcggccg attgtgaaca tggactacgt   6540
cgtgggagcc agaacgttcc gcagagaaaa gagggccgag cgtctcacct ccagggtgaa   6600
ggcactgttc agcgtgctca actacgagcg ggcgcggcgc cccggcctcc tgggcgcctc   6660
tgtgctgggc ctggacgata tccacagggc ctggcgcacc ttcgtgctgc gtgtgcgggc   6720
ccaggacccg ccgcctgagc tgtactttgt caaggtggat gtgacgggcg cgtacgacac   6780
catccccag acaggctca cggaggtcat cgccagcatc atcaaacccc agaacacgta     6840
ctgcgtgcgt cggtatgccg tggtccagaa ggccgcccat gggcacgtcc gcaaggcctt   6900
caagagccac gtctctacct tgacagacct ccagccgtac atgcgacagt tcgtggctca   6960
cctgcaggag accagcccgc tgagggatgc cgtcgtcatc gagcagagct cctccctgaa  7020
tgaggccagc agtggcctct tcgacgtctt cctacgcttc atgtgccacc acgccgtgcg  7080
catcagggc aagtcctacg tccagtgcca ggggatcccg cagggctcca tcctctccac    7140
gctgctctgc agcctgtgct acggcgacat ggagaacaag ctgtttgcgg ggattcggcg   7200
gacgggctg ctcctgcgtt tggtggatga tttcttgttg gtgacacctc acctcacccca   7260
cgcgaaaacc ttcctcagga ccctggtccg aggtgtccct gagtatggct gcgtggtgaa  7320
cttgcggaag acagtggtga acttccctgt agaagacgag gccctgggtg gcacggcttt  7380
tgttcagatg ccggcccacg gcctattccc ctggtgcggc ctgctgctgg ataccccggac 7440
cctggaggtg cagagcgact actccagcta tgcccggacc tccatcagag ccagtctcac  7500
cttcaaccgc ggcttcaagg ctgggaggaa catgcgtcgc aaactctttg ggtcttgcg   7560
gctgaagtgt cacagcctgt ttctggattt gcaggtgaac agcctccaga cggtgtgcac  7620
caacatctac aagatcctcc tgctgcaggc gtacaggttt cacgcatgtg tgctgcagct  7680
cccatttcat cagcaagttt ggaagaaccc cacattttc ctgcgcgtca tctctgacac   7740
ggcctccctc tgctactcca tcctgaaagc caagaacgca gggatgtcgc tgggggccaa  7800
gggcgccgcc ggccctctgc cctccgaggc cgtgcagtgg ctgtgccacc aagcattcct  7860
gctcaagctg actcgacacc gtgtcaccta cgtgccactc ctgggtcac tcaggacagc   7920
ccagacgcag ctgagtcgga agctcccggg gacgacgctg actgccctgg aggccgcagc  7980
caaccccggca ctgccctcag acttcaagac catcctggac tgagtcgaaa ctcgcggccg  8040
catcgcgtcga cgcgtatcga tgcatcttaa gtagatgtac ctttaagacc aatgacttac  8100
```

-continued

```
aaggcagctg tagatcttag ccactttta aaagaaaagg ggggactgga agggctaatt      8160
cactcccaac gaagacaaga tctgctttt gcttgtactg ggtctctctg gttagaccag      8220
atctgagcct gggagctctc tggctaacta gggaacccac tgcttaagcc tcaataaagc     8280
ttgccttgag tgcttcaagt agtgtgtgcc cgtctgttgt gtgactctgg taactagaga    8340
tccctcagac ccttttagtc agtgtggaaa atctctagca gtagtagttc atgtcatctt    8400
attattcagt atttataact tgcaaagaaa tgaatatcag agagtgagag gaacttgttt     8460
attgcagctt ataatggtta caaataaagc aatagcatca caaatttcac aaataaagca    8520
ttttttcac tgcattctag ttgtggtttg tccaaactca tcaatgtatc ttatcatgtc     8580
tggctctagc tatcccgccc ctaactccgc ccatcccgcc cctaactccg cccagttccg    8640
cccattctcc gccccatggc tgactaattt tttttattta tgcagaggcc gaggccgcct    8700
cggcctctga gctattccag aagtagtgag gaggctttt tggaggccta gggacgtacc    8760
caattcgccc tatagtgagt cgtattacgc gcgctcactg gccgtcgttt tacaacgtcg    8820
tgactgggaa aaccctggcg ttacccaact taatcgcctt gcagcacatc cccctttcgc    8880
cagctggcgt aatagcgaag aggcccgcac cgatcgccct tcccaacagt tgcgcagcct    8940
gaatggcgaa tgggacgcgc cctgtagcgg cgcattaagc gcggcgggtg tggtggttac    9000
gcgcagcgtg accgctacac ttgccagcgc cctagcgccc gctcctttcg ctttcttccc    9060
ttcctttctc gccacgttcg ccggcttcc ccgtcaagct ctaaatcggg gctcccttt     9120
agggttccga tttagtgctt tacggcacct cgaccccaaa aaacttgatt agggtgatgg    9180
ttcacgtagt gggccatcgc cctgatagac ggttttcgc cctttgacgt tggagtccac    9240
gttctttaat agtggactct tgttccaaac tggaacaaca ctcaaccta tctcggtcta    9300
ttcttttgat ttataaggga ttttgccgat ttcggcctat tggttaaaaa atgagctgat    9360
ttaacaaaaa tttaacgcga attttaacaa atattaacg cttacaattt aggtggcact    9420
tttcggggaa atgtgcgcgg aaccctatt tgttattt tctaaataca ttcaaatatg     9480
tatccgctca tgagacaata accctgataa atgcttcaat aatattgaaa aaggaagagt    9540
atgagtattc aacatttccg tgtcgccctt attccctttt ttgcggcatt ttgccttcct    9600
gtttttgctc acccagaaac gctggtgaaa gtaaaagatg ctgaagatca gttgggtgca    9660
cgagtgggtt acatcgaact ggatctcaac agcggtaaga tccttgagag ttttcgcccc    9720
gaagaacgtt ttccaatgat gagcactttt aaagttctgc tatgtggcgc ggtattatcc    9780
cgtattgacg ccgggcaaga gcaactcggt cgccgcatac actattctca gaatgacttg    9840
gttgagtact caccagtcac agaaaagcat cttacggatg gcatgacagt aagagaatta    9900
tgcagtgctg ccataaccat gagtgataac actgcggcca acttacttct gacaacgatc    9960
ggaggaccga aggagctaac cgcttttttg cacaacatgg gggatcatgt aactcgcctt    10020
gatcgttggg aaccggagct gaatgaagcc ataccaaacg acgagcgtga ccacacgatg    10080
cctgtagcaa tggcaacaac gttgcgcaaa ctattaactg gcgaactact tactctagct    10140
tcccggcaac aattaataga ctggatggag gcggataaag ttgcaggacc acttctgcgc    10200
tcggcccttc cggctggctg gtttattgct gataaatctg gagccggtga gcgtgggtct    10260
cgcggtatca ttgcagcact ggggccagat ggtaagccct cccgtatcgt agttatctac    10320
acgacgggga gtcaggcaac tatggatgaa cgaaatagac agatcgctga gataggtgcc    10380
tcactgatta gcattggta actgtcagac caagttacat catatatact ttagattgat    10440
ttaaaacttc attttaatt taaaaggatc taggtgaaga tccttttga taatctcatg    10500
```

-continued

```
accaaaatcc cttaacgtga gttttcgttc cactgagcgt cagacccgt agaaaagatc    10560 aaaggatctt cttgagatcc ttttttttctg cgcgtaatct gctgcttgca aacaaaaaaa  10620
ccaccgctac cagcggtggt ttgtttgccg gatcaagagc taccaactct ttttccgaag   10680
gtaactggct tcagcagagc gcagatacca aatactgttc ttctagtgta gccgtagtta   10740
ggccaccact tcaagaactc tgtagcaccg cctacatacc tcgctctgct aatcctgtta   10800
ccagtggctg ctgccagtgg cgataagtcg tgtcttaccg ggttggactc aagacgatag   10860
ttaccggata aggcgcagcg gtcgggctga acgggggggtt cgtgcacaca gcccagcttg   10920
gagcgaacga cctacaccga actgagatac ctacagcgtg agctatgaga aagcgccacg   10980
cttcccgaag ggagaaaggc ggacaggtat ccggtaagcg gcagggtcgg aacaggagag   11040
cgcacgaggg agcttccagg gggaaacgcc tggtatcttt atagtcctgt cgggtttcgc   11100
cacctctgac ttgagcgtcg attttttgtga tgctcgtcag gggggcggag cctatggaaa  11160
aacgccagca acgcggcctt tttacggttc ctggcctttt gctggccttt tgctcacatg   11220
ttctttcctg cgttatcccc tgattctgtg gataaccgta ttaccgcctt tgagtgagct   11280
gataccgctc gccgcagccg aacgaccgag cgcagcgagt cagtgagcga ggaagcggaa   11340
gagcgcccaa tacgcaaacc gcctctcccc gcgcgttggc cgattcatta atgcagctgg   11400
cacgacaggt ttcccgactg gaaagcgggc agtgagcgca acgcaattaa tgtgagttag   11460
ctcactcatt aggcacccca ggctttacac tttatgcttc cggctcgtat gttgtgtgga   11520
attgtgagcg gataacaatt tcacacagga aacagctatg accatgatta cgccaagcgc   11580
gcaattaacc ctcactaaag ggaacaaaag ctggagctgc aagctt                  11626
```